US010456443B2

(12) United States Patent
Pei et al.

(10) Patent No.: US 10,456,443 B2
(45) Date of Patent: Oct. 29, 2019

(54) PEPTIDYL CALCINEURIN INHIBITORS

(71) Applicant: OHIO STATE INNOVATION FOUNDATION, Columbus, OH (US)

(72) Inventors: Dehua Pei, Columbus, OH (US); Ziqing Qian, Columbus, OH (US); John W Christman, Columbus, OH (US); Manjula Karpurapu, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 15/506,877

(22) PCT Filed: Aug. 27, 2015

(86) PCT No.: PCT/US2015/047267

§ 371 (c)(1), (2) Date: Feb. 27, 2017

(87) PCT Pub. No.: WO2016/033368

PCT Pub. Date: Mar. 3, 2016

(65) Prior Publication Data

US 2017/0281723 A1 Oct. 5, 2017

Related U.S. Application Data

(60) Provisional application No. 62/042,715, filed on Aug. 27, 2014.

(51) Int. Cl.

| | |
|---|---|
| ***A61K 38/13*** | (2006.01) |
| ***A61K 38/17*** | (2006.01) |
| ***A61K 47/64*** | (2017.01) |
| ***A61P 11/00*** | (2006.01) |

(52) U.S. Cl.

CPC .......... *A61K 38/13* (2013.01); *A61K 38/1709* (2013.01); *A61K 47/645* (2017.08); *A61P 11/00* (2018.01)

(58) Field of Classification Search

None

See application file for complete search history.

(56) References Cited

U.S. PATENT DOCUMENTS

| | | | |
|---|---|---|---|
| 5,965,536 | A | 10/1999 | Cohen et al. |
| 6,110,889 | A | 8/2000 | Miller et al. |
| 6,251,854 | B1 | 6/2001 | Montal et al. |
| 6,355,619 | B1 | 3/2002 | Miller et al. |
| 6,593,292 | B1 | 7/2003 | Rothbard et al. |
| 6,605,115 | B1 | 8/2003 | Cooke et al. |
| 6,649,587 | B1 | 11/2003 | Frydman et al. |
| 6,669,951 | B2 | 12/2003 | Rothbard et al. |
| 6,730,293 | B1 | 5/2004 | Rothbard et al. |
| 6,759,387 | B2 | 7/2004 | Rothbard et al. |
| 6,794,545 | B1 | 9/2004 | Frydman et al. |
| 6,809,176 | B2 | 10/2004 | Blokhin et al. |
| 6,960,648 | B2 | 11/2005 | Bonny |
| 6,982,351 | B2 | 1/2006 | Frydman et al. |
| 7,026,347 | B2 | 4/2006 | Frydman et al. |
| 7,084,241 | B2 | 8/2006 | Hogan et al. |
| 7,169,814 | B2 | 1/2007 | Rothbard et al. |
| 7,186,825 | B2 | 3/2007 | Frydman et al. |
| 7,229,961 | B2 | 6/2007 | Rothbard et al. |
| 7,253,207 | B2 | 8/2007 | Blokhin et al. |
| 7,279,502 | B2 | 10/2007 | Clifford et al. |
| 7,312,244 | B2 | 12/2007 | Clifford et al. |
| 7,585,834 | B2 | 9/2009 | Wender et al. |
| 7,816,490 | B2 | 10/2010 | Hogan et al. |
| 8,614,290 | B2 | 12/2013 | Wester et al. |
| 8,628,750 | B2 | 1/2014 | Wester et al. |
| 8,629,112 | B2 | 1/2014 | Gombert et al. |
| 9,169,290 | B2 | 10/2015 | O'Neil |
| 2002/0009491 | A1 | 1/2002 | Rothbard et al. |
| 2002/0035243 | A1 | 3/2002 | Imfeld et al. |
| 2002/0120100 | A1 | 8/2002 | Bonny |
| 2002/0127198 | A1 | 9/2002 | Rothbard et al. |
| 2003/0022831 | A1 | 1/2003 | Rothbard et al. |
| 2003/0032593 | A1 | 2/2003 | Wender et al. |
| 2003/0032594 | A1 | 2/2003 | Bonny |
| 2003/0072715 | A1 | 4/2003 | Frydman et al. |
| 2003/0130356 | A1 | 7/2003 | Frydman et al. |
| 2003/0167129 | A1 | 9/2003 | Nestor et al. |
| 2004/0002117 | A1 * | 1/2004 | Hogan .................. C07K 5/101 435/7.1 |
| 2004/0152687 | A1 | 8/2004 | Frydman et al. |
| 2004/0192665 | A1 | 9/2004 | Frydman et al. |
| 2004/0248783 | A1 | 12/2004 | Kawabe et al. |
| 2005/0192210 | A1 | 9/2005 | Rothbard et al. |
| 2006/0128614 | A1 | 6/2006 | Cheng et al. |
| 2006/0141514 | A1 | 6/2006 | Rozzelle et al. |
| 2007/0093427 | A1 | 4/2007 | Matsui et al. |
| 2012/0045393 | A1 | 2/2012 | Linder et al. |
| 2014/0303071 | A1 | 10/2014 | O'Neil |
| 2015/0038671 | A1 | 2/2015 | Parang et al. |
| 2016/0031941 | A1 | 2/2016 | Eckert et al. |
| 2017/0112896 | A1 | 4/2017 | Briesewitz |
| 2017/0190743 | A1 | 7/2017 | Pei et al. |
| 2017/0304383 | A1 | 10/2017 | Briesewitz et al. |

FOREIGN PATENT DOCUMENTS

| | | |
|---|---|---|
| CA | 2417064 | 2/2002 |
| CA | 2455951 | 2/2003 |
| CN | 105440105 | 3/2016 |
| EP | 1185493 | 7/2005 |
| EP | 1574507 | 9/2005 |
| JP | 3791981 | 6/2006 |
| JP | 2016065018 | 4/2016 |
| WO | 1999021877 | 5/1999 |
| WO | 2000011022 | 3/2000 |
| WO | 2001013957 | 3/2001 |
| WO | 2002057313 | 7/2002 |

(Continued)

OTHER PUBLICATIONS

Bold et al. (J. Med. Chem. 1998, 41, 3387-3401) (Year: 1998).*

(Continued)

*Primary Examiner* — Sergio Coffa
(74) *Attorney, Agent, or Firm* — Meunier Carlin & Curfman LLC

(57) ABSTRACT

Improved calcineurin inhibitors and methods of using these improved calcineurin inhibitors to inhibit calcineurin-NFAT signaling in cells and in subjects are disclosed.

9 Claims, 18 Drawing Sheets

Specification includes a Sequence Listing.

(56) References Cited

FOREIGN PATENT DOCUMENTS

| | | |
|---|---|---|
| WO | 2002064091 | 8/2002 |
| WO | 2002067917 | 9/2002 |
| WO | 2002090503 | 11/2002 |
| WO | 2003059942 | 7/2003 |
| WO | 03/070755 | 8/2003 |
| WO | 2003092631 | 11/2003 |
| WO | 2003092632 | 11/2003 |
| WO | 2004050685 | 6/2004 |
| WO | 2006041805 | 4/2006 |
| WO | 2006058436 | 6/2006 |
| WO | 2006086773 | 8/2006 |
| WO | 2007040535 | 4/2007 |
| WO | 2007055578 | 5/2007 |
| WO | 2007070372 | 6/2007 |
| WO | 2007072037 | 6/2007 |
| WO | 2007096662 | 8/2007 |
| WO | 2007106554 | 9/2007 |
| WO | 2007108749 | 9/2007 |
| WO | 2007111993 | 10/2007 |
| WO | 2008077194 | 7/2008 |
| WO | 2009027706 | 3/2009 |
| WO | 2009092062 | 7/2009 |
| WO | 2010045335 | 4/2010 |
| WO | 2010107832 | 9/2010 |
| WO | 2011095218 | 8/2011 |
| WO | 2011095607 | 8/2011 |
| WO | 2013142184 | 9/2013 |
| WO | 2014053629 | 4/2014 |
| WO | WO 2015/179691 | * 11/2015 |
| WO | 2016033368 | 3/2016 |
| WO | 2016044683 | 3/2016 |

OTHER PUBLICATIONS

International Search Report and Written Opinion issued in International Application No. PCT/US2015/47267, dated Dec. 7, 2015.

International Preliminary Report on Patentability issued in issued in International Application No. PCT/US2015/47267, dated Mar. 9, 2017.

Aramburu, J.; et al., "Selective inhibition of NFAT activation by a peptide spanning the calcineurin targeting site of NFAT." Mol. Cell 1998, 1, 627-637.

Aramburu, J.; et al., "Affinity-driven peptide selection of an NFAT inhibitor more selective than cyclosporine a." Science 1999, 285, 2129-2133.

Bold, G.; et al., "New aza-dipeptide analogues as potent and orally absorbed HIV-1 protease inhibitors: candidates for clinical development." J. Med. Chem. 1998, 41, 3387-3401. abstract.

Chapman, J. R. "Chronic calcineurin inhibitor nephrotoxicity-lest we forget." Am. J. Transplant 2011, 11, 693-697.

Chierici, S.; et al., "A case study of 2,2-dimethylthiazolidine as locked cis proline amide bond: synthesis, NMR and molecular modeling studies of a δ-conotoxin EVIA peptide analog." Org. Biomol. Chem. 2004, 2, 2436-2441.

Crabtree, G. R. "Generic signals and specific outcomes: signaling through $Ca^{2+}$, calcineurin, and NF-AT." Cell 1999, 96, 611-614.

Davies, S. J.; et al., "Structure-activity relationships of the peptide deformylase inhibitor BB-3497: modification of the P2' and P3' side chains." Bioorg. Med. Chem. Lett. 2003, 13, 2715-2718.

DePaul, A. J.; et al., "Equilibrium conformational dynamics in an RNA tetraloop from massively parallel molecular dynamics." Nucleic Acids Res. 2010, 38, 4856-4867.

Dumy, P.; et al., "Pseudo-prolines as a molecular hinge: reversible induction of cis amide bonds into peptide backbones." J. Am. Chem. Soc. 1997, 119, 918-925.

Grigoriu, S.; et al., "The molecular mechanism of substrate engagement and immunosuppressant inhibition of calcineurin." PLoS Biol. 2013, 11, e1001492.

Gwack, Y.; et al., "A genome-wide *Drosophila* RNAi screen identifies DYRK-family kinases as regulators of NFAT." Nature 2006, 441, 646-650.

Hojo, M.; et al., "Cyclosporine induces cancer progression by a cell-autonomous mechanism." Nature 1999, 397, 530-534.

Humphrey, W.; et al., "VMD: visual molecular dynamics." J. Mol. Graphics 1996, 14, 33-38.

Jórárt, B.; et al., "Performance of the general amber force field in modeling aqueous POPC membrane bilayers." J. Comput. Chem. 2007, 28, 2051-2058.

Jorgensen, W. L.; et al., "Solvation and Conformation of Methanol in Water." J. Am. Chem. Soc. 1983, 105, 1407-1413.

Kaduk, C.; et al., "Synthesis of Fmoc-amino acid fluorides via DAST, an alternative fluoridation agent." Lett. Pep. Sci. 1995, 2, 285-288.

Kang, S.; et al., "Inhibition of the calcineurin-NFAT interaction by small organic molecules reflects binding at an allosteric site." J. Biol. Chem. 2005, 280, 37698-37706.

Kiani, A.; et al., "Manipulating immune responses with immunosuppressive agents the target NFAT." Immunity 2000, 12, 359-372.

Li, H.; et al., "Interaction of calcineurin with substrates and targeting proteins." Trends Cell Biol. 2011, 21, 91-103.

Li, H.; et al., "Structural delineation of the calcineurin-NFAT interaction and its parallels to PP1 targeting interactions." J. Mol. Biol. 2004, 342, 1659-1674.

Li, H.; et al., "Structure of calcineurin in complex with PVIVIT peptide: portrait of a low-affinity signaling interaction." J. Mol. Biol. 2007, 369, 1296-1306.

Liu, J.; et al., "Calcineurin is a common target of cyclophilin-cyclosporine A and FKBP-FK506 complexes." Cell 1991, 66, 807-815.

Llinas-Brunet, M.; et al., "A systematic approach to the optimization of substrate-based inhibitors of the hepatitis C virus NS3 protease: discovery of potent and specific tripeptide inhibitors." J. Med. Chem. 2004, 47, 6584-6594.

Luechapanichkul, R.; et al., "Specificity profiling of dual specificity phosphatase vaccinia VH1-related (VHR) reveals two distinct substrate binding modes." J. Biol. Chem. 2013, 288, 6498-6510.

Nguyen, L. T.; et al., "Serum stabilities of short tryptophan- and arginine-rich antimicrobial peptide analogs." PLoS One 2010, 5, e12684.

Noguchi, H.; et al., "A new cell-permeable peptide allows successful allogeneic islet transplantation in mice." Nat. Med. 2004, 10, 305-309.

Perni, R. B.; et al., "Preclinical profile of VX-950, a potent, selective, and orally bioavailable inhibitor of hepatitis C Virus NS3-4A serine protease." Antimicrob. Agents Chemother. 2006, 50, 899-909.

Pettersen, E. F.; et al., "UCSF Chimera—a visualization system for exploratory research and analysis." J. Comput. Chem. 2004, 13, 1605-1612.

Platz, K. P.; et al., "Nephrotoxicity following orthotopic liver transplantation. A comparison between cyclosporine and FK506." Transplantation 1994, 58, 170-178.

Qian et al., "Structure-Based Optimization of a Peptidyl Inhibitor against Calcineurin-Nuclear Factor of Activated T Cell (NFAT) Interaction." J. Med. Chem. 2014, 57, 7792-7797.

Rao, A.; et al., "Transcription factors of the NFAT family: regulation and function." Annu. Rev. Immunol. 1997, 15, 707-747.

Roy, J.; et al., "Cracking the phosphatase code: Docking interactions determine substrate specificity." Sci. Signal. 2009, 2, re9, 1-7.

Sieber, M.; et al., "Novel inhibitors of the calcineurin/NFATc hub—alternatives to CsA and FK506?" Cell Commun. Signal. 2009, 7, 25.

Sigal, N. H.; et al., "Is cyclophilin involved in the immunosuppressive and nephrotoxic mechanism of action of cyclosporine A?" J. Exp. Med. 1991, 173, 619-628.

Sigman, M. S.; et al., "Schiff base catalysts for the asymmetric Strecker reaction identified and optimized from parallel synthetic libraries." J. Am. Chem. Soc. 1998, 120, 4901-4902.

Sorin, E. J.; et al., "Exploring the helix-coil transition via all-atom equilibrium ensemble simulations." Biophys. J. 2005, 88, 2472-2493.

Sousa da Silva, A. W.; et al., "ACPYPE—AnteChamberPYthon Parser interfacE." BMC Res. Notes 2012, 5, 367.

(56) References Cited

OTHER PUBLICATIONS

Takeuchi, K.; et al., "Structure of the calcineurin-NFAT complex: defining a T cell activation switch using solution NMR and crystal coordinates." Structure 2007, 15, 587-597.
Wang, J.; et al., "Automatic atom type and bond type perception in molecular mechanical calculations." J. Mol. Graphic. Model. 2006, 25, 247-260.
Wang, J.; et al., "Development and testing of a general AMBER force field." J. Comput. Chem. 2004, 25, 1157-1174.
Wedemeyer, W. J.; et al., "Proline cis-trans isomerization and protein folding." Biochemistry 2002, 41, 14637-14644.
Wohr, T.; et al., "Pseudo-prolines as a solubilizing, structure-disrupting protection technique in peptide synthesis." J. Am. Chem. Soc. 1996, 118, 9218-9227.
Yu, H., "Therapeutic potential of VIVIT, a selective peptide inhibitor of nuclear factor of activated T cells, in cardiovascular disorders." Cardiovasc Drug Rev. 2007 Summer;25(2):175-87.
Alonso, A et al., Protein tyrosine phosphatases in the human genome, Cell, Jun. 2004, 117(6):699-711.
Andaloussi, S. E. L. et al., "Design of a peptide-based vector, PepFect6, for efficient delivery of siRNA in cell culture and systemically in vivo," Nucleic Acids Research, May 2011, 39(9):3972-3987.
Anderl, J. et al., "Chemical modification allows phallotoxins and amatoxins to be used as tools in cell biology," Beilstein Journal of Organic Chemistry, 2012, 8(233):2072-2084.
Appelbaum, J. S. et al., "Arginine Topology Controls Escape of Minimally Cationic Proteins from Early Endosomes to the Cytoplasm," Chemistry & Biology, Jul. 2012, 19:819-830.
Birts, C. N. et al., "A cyclic peptide inhibitor of C-terminal binding protein dimerization links metabolism with mitotic fidelity in breast cancer cells," Chem. Sci. 2013, 4, 3046-3057.
Bolte, S. et al., "A guided tour into subcellular colocalization analysis in light microscopy," J. Microsc., Dec. 2006, 224(Pt. 3), 213-232.
Burke, T.R. Jr. et al., "Potent Inhibition of Insulin Receptor Dephosphorylation by a Hexamer Peptide Containing the Phosphotyrosyl Mimetic F2Pmp," Biochem. Biophys. Res. Commun., Oct. 1994, 204(1):129-134.
Carpenter, A E. et al., "CellProfiler: image analysis software for identifying and quantifying cell phenotypes," Genome Biology, 2006, 7:R100, 11 pages.
Cascales, L. et al., "Identification and Characterization of a New Family of Cell-Penetrating Peptides," J. Biol. Chem., Oct. 2011, 286(42):36932-36943.
Chatterjee, J. et al., "N-Methylation of Peptides: A New Perspective in Medicinal Chemistry," Acc. Chem. Res., 2008, 41(10):1331-1342.
Chen, X. et al., "On-Bead Screening of Combinatorial Libraries: Reduction of Nonspecific Binding by Decreasing Surface Ligand Density," J. Comb. Chem. 2009, 11(4):604-611.
Cheng, S. H. et al., "Defective intracellular transport and processing of CFTR is the molecular basis of most cystic fibrosis," Cell, Nov. 1990, 63(4):827-834.
Cooley, C. B. et al., "Oligocarbonate Molecular Transporters: Oligomerization-Based Syntheses and Cell-Penetrating Studies," J. Am. Chem. Soc., 2009, 131(45):16401-16403.
Cushing, P. R. et al., "The Relative Binding Affinities of PDZ Partners for CFTR: A Biochemical Basis for Efficient Endocytic Recycling," Biochemistry, 2008, 47(38): 10084-10098.
Cushing, P. R. et al., "A Stabilizing Influence: CAL PDZ Inhibition Extends the Half-Life of L1F508-CFTR," Angew. Chem. Int. Ed., Dec. 2010, 49(51):9907-9911.
Deshayes, S. et al., "Cell-penetrating peptides: tools for intracellular delivery of therapeutics," Cell. Mol. Life Sci., Aug. 2005, 62(16):1839-1849.
Dewan, V. et al., "Cyclic Peptide Inhibitors of HIV-1 Capsid-Human Lysyl-tRNA Synthetase Interaction," ACS Chem. Biol., 2012, 7(4):761-769.
Doyle, D. A et al., "Crystal Structures of a Complexed and Peptide-Free Membrane Protein-Binding Domain: Molecular Basis of Peptide Recognition by PDZ," Cell, Jun. 1996, 85(7):1067-1076.
Driggers, E. M. et al., "The exploration of macrocycles for drug discovery—an underexploited structural class," Nat. Rev. Drug Discov., Jul. 2008, 7:608-624.
Duchardt, F. et al., "A Comprehensive Model for the Cellular Uptake of Cationic Cell-penetrating Peptides," Traffic, Jul. 2007, 8(7):848-866.
Duchardt, F. et al., "A Cell-penetrating Peptide Derived from Human Lactoferrin with Conformation-dependent Uptake Efficiency," J. Biol. Chem., Dec. 2009, 284(52):36099-36108.
Eguchi, A. et al., "Protein Transduction Domain of HIV-1 Tat Protein Promotes Efficient Delivery of DNA into Mammalian Cells," J. Biol. Chem., Jul. 2001, 276:26204-26210.
Eichler, J. et al., "Novel a-glucosidase inhibitors identified using multiple cyclic peptide combinatorial libraries," Molecular Diversity, Aug. 1996, 1(4):233-240.
Elchelby, M. et al., "Increased insulin sensitivity and obesity resistance in mice lacking the protein tyrosine phosphatase-18 gene," Science, Mar. 1999, 283(5407):1544-1548.
El-Sayed, A et al., "Delivery of Macromolecules Using Arginine-Rich Cell-Penetrating Peptides: Ways to Overcome Endosomal Entrapment," The AAPS Journal, Mar. 2009, 11(1):13-22.
Fernandez-Lopez, S. et al., "Antibacterial agents based on the cyclic D,L-alpha-peptide architecture," Nature, Jul. 2001, 412:452-455 and Correction page, Nature, Nov. 2001, 414:329.
Ferrari, A. et al., "Caveolae-Mediated Internalization of Extracellular HIV-1 Tat Fusion Proteins Visualized in Real Time," Molecular Therapy, 2003, 8:284-294.
Fittipaldi, A. et al., "Cell Membrane Lipid Rafts Mediate Caveolar Endocytosis of HIV-1 Tat Fusion Proteins," J. Biol. Chem., Sep. 2003, 278:34141-34149.
Frackenpohl, J. et al., "The Outstanding Biological Stability of – and y-Peptides toward Proteolytic Enzymes: An In Vitro Investigation with Fifteen Peptidases," Chembiochem, Jun. 2001, 2(6):445-455.
Frankel, A D. et al., "Cellular uptake of the tat protein from human immunodeficiency virus," Cell, Dec. 1988, 55(6):1189-1193.
Frost, J. R. et al., "Macrocyclization of Organo-Peptide Hybrids through a Dual Bio-orthogonal Ligation: Insights from Structure-Reactivity Studies," ChemBioChem, Jan. 2013, 14(1):147-160.
Futaki, S., "Membrane-permeable arginine-rich peptides and the translocation mechanisms," Advanced Drug Delivery Reviews, Feb. 2005, 57(4): 547-558.
Futaki, S. et al., "Arginine-rich peptides. An abundant source of membrane-permeable peptides having potential as carriers for intracellular protein delivery." The Journal of Biological Chemistry, 2001, 276(8):5836-5840.
Giebel, L. B. et al., "Screening of cyclic peptide phage libraries identifies ligands that bind streptavidin with high affinities," Biochemistry, 1995, 34(47):15430-15435.
Gobbo, M. et al, "Synthesis and biological activity of some linear and cyclic kinin analogues," International Journal of Peptide & Protein Research, Jul. 1994, 44(1):1-9.
Goncalves, E. et al., "Binding of Oligoarginine to Membrane Lipids and Heparan Sulfate: Structural and Thermodynamic Characterization of a Cell-Penetrating Peptide," Biochemistry, 2005, 44(7):2692-2702.
Goun, E. A et al., "Molecular Transporters: Synthesis of Oligoguanidinium Transporters and Their Application to Drug Delivery and Real-Time Imaging," ChemBioChem, Oct. 2006, 7(10):1497-1515.
Green, M. et al., "Autonomous functional domains of chemically synthesized human immunodeficiency virus Tat trans-activator protein," Cell, Dec. 1988, 55(6): 1179-1188.
Gupta, B. et al., "Intracellular delivery of large molecules and small particles by cell-penetrating proteins and peptides," Advanced Drug Delivery Reviews, Feb. 2005, 57(4):637-651.
Hamill, K. M. et al., "Polymyxins facilitate entry into mammalian cells" Chem. Sci., 2016, 7:5059-5068.

(56) References Cited

OTHER PUBLICATIONS

Hariton-Gazal, E. et al., "Functional Analysis of Backbone Cyclic Peptides Bearing the Arm Domain of the HIV-1 Rev Protein: Characterization of the Karyophilic Properties and Inhibition of Rev-Induced Gene Expression," Biochemistry, 2005, 44(34): 11555-11566.
He, R et al., "Recent Advances in PTP1B Inhibitor Development for the Treatment of Type 2 Diabetes and Obesity," Chapter 6 In: New Therapeutic Strategies for Type 2 Diabetes: Small Molecule Approaches, Jones, R. M. (ed.), RSC Drug Discovery Series No. 27, The Royal Society of Chemistry, 2012, pp. 142-176.
Heinis, C. et al., "Phage-encoded combinatorial chemical libraries based on bicyclic peptides," Nat. Chem. Biol., 2009, 5:502-507.
Herce, H. D. et al., "Molecular dynamics simulations suggest a mechanism for translocation of the HIV-1 TAT peptide across lipid membranes," Proc. Natl. Acad. Sci. U. S. A., Dec. 2007, 104(52):20805-20810.
Herce, H. D. et al., "Arginine-Rich Peptides Destabilize the Plasma Membrane, Consistent with a Pore Formation Translocation Mechanism of Cell-Penetrating Peptides," Biophys. J., Oct. 2009, 97(7): 1917-1925.
Hili R. et al., "Macrocyclization of Linear Peptides Enabled by Amphoteric Molecules," J. Am. Chem. Soc., 2010, 132(9):2889-2891.
Hirose, H. et al., "Transient Focal Membrane Deformation Induced by Arginine-rich Peptides Leads to Their Direct Penetration into Cells," Mol. Ther., 2012, 20(5):984-993.
Holub, J. M. et al., "Improved assays for determining the cytosolic access of peptides, proteins, and their mimetics," Biochemistry, Dec. 2013, 52(50):9036-9046.
Horn, M. et al., "Tuning the properties of a novel short cell-penetrating peptide by intramolecular cyclization with a triazole bridge," Chem. Commun. 2016, 52:2261-2264.
Hoyer, J. et al., "Peptide Vectors for the Nonviral Delivery of Nucleic Acids," Acc. Chem. Res., 2012, 45(7): 1048-1056.
Illsley, N. P. et al., "Membrane chloride transport measured using a chloride-sensitive fluorescent probe," Biochemistry, 1987, 26(5):1215-1219.
Jang, S. et al., "Cell-Penetrating, Dimeric a-Helical Peptides: Nanomolar Inhibitors of HIV-1 Transcription", Angew. Chem. Int. Ed. 2014, 53, 10086-10089.
Jeong, J. H. et al., "siRNA Conjugate Delivery Systems," Bioconjugate Chem., 2009, 20(1):5-14.
Jha, D. et al., "CyLoP-1: A Novel Cysteine-Rich Cell-Penetrating Peptide for Cytosolic Delivery of Cargoes," Bioconj. Chem., 2011, 22(3) :319-328.
Jiang, B. et al., "A Selective, Cell-Permeable Nonphosphorylated Bicyclic Peptidyl Inhibitor against Peptidyl-Prolyl lsomerase Pin1," J. Med. Chem., 58:6306-6312 (2015). Published Online: Jul. 21, 2015.
Joo, S. H. et al., "High-Throughput Sequence Determination of Cyclic Peptide Library Members by Partial Edman Degradation/ Mass Spectrometry," J. Am. Chem. Soc., 2006, 128(39):13000-13009.
Josephson, L. et al., "High-Efficiency Intracellular Magnetic Labeling with Novel Superparamagnetic-Tat Peptide Conjugates," Bioconjugate Chem., 1999, 10(2):186-191.
Junkes, C. et al., "Cyclic antimicrobial R-, W-rich peptides: the role of peptide structure and *E. coli* outer and inner membranes in activity and the mode of action," European Biophysics Journal, 2011, 40(4):515-528.
Kaplan, I. M. et al., "Cationic TAT peptide transduction domain enters cells by macropinocytosis," Journal of Controlled Release, Jan. 2005, 102(1):247-253.
Kawakami, T. et al., "In Vitro Selection of Multiple Libraries Created by Genetic Code Reprogramming to Discover Macrocyclic Peptides That Antagonize VEGFR2 Activity in Living Cells," ACS Chem. Biol., Apr. 2013, 8(6):1205-1214.
Kerem, B. et al., "Identification of the cystic fibrosis gene: genetic analysis," Science, Sep. 1989, 245(4922):1073-1080.
Kohli, R. M. et al., "Biomimetic synthesis and optimization of cyclic peptide antibiotics," Nature, Aug. 2002, 418:658-661.
Kritzer, J. A. et al., "Rapid selection of cyclic peptides that reduce a-synuclein toxicity in yeast and animal models," Nature Chemical Biology, Sep. 2009, 5(9):655-663.
Kundu, R. et al., "Hybrid Organic-Inorganic Inhibitors of a PDZ Interaction that Regulates the Endocytic Fate of CFTR," Angew. Chem. Int. Ed., Jul. 2012, 51(29):7217-7220.
Kwon, Y-U et al., "Quantitative Comparison of the Relative Cell Permeability of Cyclic and Linear Peptides," Chemistry & Biology, Jun. 2007, 14(6):671-677.
Lalonde, M.S. et al., "Inhibition of Both HIV-1 Reverse Transcription and Gene Expression by a Cyclic Peptide that Binds the Tat-Transactivating Response Element (TAR) RNA", PLoS Pathogenes May 2011, 7(5) e1002038.
LaMontagne, K. R. Jr. et al., "Protein tyrosine phosphatase PTP1B suppresses p210 bcr-abl-induced transformation of Rat-1 fibroblasts and promotes differentiation of K562 cells," Proc. Natl. Acad. Sci. U. S. A., Nov. 1998, 95(24):14094-14099.
LaRochelle, J. R. et al., "Fluorescence Correlation Spectroscopy Reveals Highly Efficient Cytosolic Delivery of Certain Penta-Arg Proteins and Stapled Peptides," Journal of the American Chemical Society, 2015, 137:2536-2541.
Lattig-Tunnemann, G. et al., "Backbone rigidity and static presentation of guanidinium groups increases cellular uptake of arginine-rich cell-penetrating peptides," Nature Communications, 2011, 2:453. 6 pages.
Leduc, A-M et al., "Helix-stabilized cyclic peptides as selective inhibitors of steroid receptor-coactivator interactions," Proc. Natl. Acad. Sci. U.S.A., Sep. 2003, 100(20): 11273-11278.
Lee, H. J. et al., "PDZ domains and their binding partners: structure, specificity, and modification," Cell Communication and Signaling, 2010, 8:8, 18 pages.
Lee, J. et al., "Using marine natural products to discover a protease that catalyzes peptide macrocyclization of diverse substrates," J. Am. Chem. Soc., Feb. 2009, 131(6):2122-2124.
Lessard, L. et al., "The two faces of PTP1B in cancer," Biochim. Biophys. Acta, Mar. 2010, 1804(3):613- 619.
Li, S. et al, "Photolithographic synthesis of cyclic peptide arrays using a differential deprotection strategy," Chem. Commun., 2005, 5:581-583.
Li, S. et al., "Fluoride enhances the activity of fungicides that destabilize cell membranes," Bioorganic & Medicinal Chemistry Letters, 2012, 22(9):3317-3322.
Lian, W. et al., "Cell-permeable bicyclic peptide inhibitors against intracellular proteins," J. Am. Chem. Soc., Jul. 2014, 136(28):9830-9833.
Lian, W. et al., "Screening Bicyclic Peptide Libraries for Protein-Protein Interaction Inhibitors: Discovery of a Tumor Necrosis Factor-a Antagonist," J. Am. Chem. Soc., 2013, 135(32): 11990-11995.
Lin, K-J, et al., "QSAR studies of antimicrobial alpha, beta-polypeptides," Pharmaceutical Biotechnology, 2003, 10(5):299-303 (with English Abstract).
Lindgren M. et al., "Classes and Prediction of Cell-Penetrating Peptides," Chapter 1 In: Cell-Penetrating Peptides: Methods and Protocols, Methods in Molecular Biology, vol. 683, pp. 3-19, Springer Science+Business Media, LLC 2011.
Liu, J. et al., "Nanostructured Materials Designed for Cell Binding and Transduction," Biomacromolecules, 2001, 2(2):362-368.
Liu, R. et al., "A Novel Peptide-Based Encoding System for "One-Bead One-Compound" Peptidomimetic and Small Molecule Combinatorial Libraries," J. Am. Chem. Soc., 2002, 124(26):7678-7680.
Liu, T. et al., "High-Throughput Screening of One-Bead-One-Compound Libraries: Identification of Cyclic Peptidyl Inhibitors against Calcineurin/NFAT Interaction," ACS Comb. Sci., 2011, 13(5):537-546.
Liu, T. et al., "Membrane Permeable Cyclic Peptidyl Inhibitors against Human Peptidylprolyl lsomerase Pin1," J. Med. Chem., 2010, 53(6):2494-2501.

(56) References Cited

OTHER PUBLICATIONS

Liu, Y. et al., "Multifunctional Tandem Peptide Modified Paclitaxel-Loaded Liposomes for the Treatment of Vasculogenic Mimicry and Cancer Stem Cells in Malignant Glioma," ACS Applied Materials & Interfaces, 2015, 7(30):16792-16801.
Lu, K. P. et al., "The prolyl isomerase PIN1: a pivotal new twist in phosphorylation signalling and disease," Nat. Rev. Mol. Cell Biol., Nov. 2007, 8:904-916.
Magzoub, M. et al., "Conformational states of the cell-penetrating peptide penetratin when interacting with phospholipid vesicles: effects of surface charge and peptide concentration," Biochim. Biophys. Acta, Jun. 2002, 1563(1-2):53-63.
Maiolo, J. R. et al., "Effects of cargo molecules on the cellular uptake of arginine-rich cell-penetrating peptides," Biochim. Biophys. Acta., Jul. 2005, 1712(2): 161-172.
Maly, D. J. et al., "Combinatorial Strategies for Targeting Protein Families: Application to the Proteases," Chembiochem, Jan. 2002, 3(1):16-37.
Maly, D. J. et al., "Expedient Solid-Phase Synthesis of Fluorogenic Protease Substrates Using the 7-Amino-4-carbamoylmethylcoumarin (ACC) Fluorophore," J. Org. Chem., 2002, 67(3):910-915.
Mandal, D. et al., "Cell-Penetrating Homochiral Cyclic Peptides as Nuclear-Targeting Molecular Transporters," Angew. Chem. Int. Ed., 2011, 50:9633-9637.
Marsault, E. et al., "Macrocycles Are Great Cycles: Applications, Opportunities, and Challenges of Synthetic Macrocycles in Drug Discovery," J. Med. Chem., 2011, 54(7): 1961-2004.
Meutermans, W. D. F. et al., "Synthesis of Difficult Cyclic Peptides by Inclusion of a Novel Photolabile Auxiliary in a Ring Contraction Strategy," J. Am. Chem. Soc., 1999, 121(42):9790-9796. Published Online: Oct. 8, 1999.
Millward, S. W. et al., "A General Route for Post-Translational Cyclization of mRNA Display Libraries," J. Am. Chem. Soc., 2005, 127(41):14142-14143. Published Online: Sep. 27, 2005.
Millward, S. W. et al., "Design of Cyclic Peptides That Bind Protein Surfaces with Antibody-Like Affinity," ACS Chem Biol., 2007, 2(9):625-634. Published Online: Sep. 21, 2007.
Ming, Z. et al., "Synthesis of RGD containing peptides and their vasodilation effect," Preparative Biochemistry 8 Biotechnology, 2000, 30(3):247-256.
Miranda, E. et al., "A Cyclic Peptide Inhibitor of HIF-1 Heterodimerization That Inhibits Hypoxia Signaling in Cancer Cells," Journal of the American Chemical Society, 2013, 135(28): 10418-10425.
Miskolzie, M. et al., "An NMR conformational analysis of cyclic bradykinin mimics. Evidence for a-turn," Journal of Biomolecular Structure & Dynamics, 2000, 17(6):947-955.
Mitra, S. et al., "Highly sensitive peptide-based probes for protein tyrosine phosphatase activity utilizing a fluorogenic mimic of phosphotyrosine," Bioorg. Med. Chem. Lett., Dec. 2005, 15(23):5142-5145.
Moore, J. D. et al., "Pin1 inhibitors: Pitfalls, progress and cellular pharmacology," Bioorg. Med. Chem. Lett., Aug. 2013, 23(15):4283-4291.
Morais Cabral, J. H. et al., "Crystal structure of a PDZ domain," Nature, Aug. 1996, 382:649-652.
Mosmann, T., "Rapid colorimetric assay for cellular growth and survival: Application to proliferation and cytotoxicity assays," J. lmmunol. Methods, Dec. 1983, 65(1-2):55-63.
Mueller, J. et al., "Comparison of Cellular Uptake Using 22 CPPs in 4 Different Cell Lines," Bioconjugate Chem., 2008, 19(12):2363-2374.
Muratovska, A. et al., "Conjugate for efficient delivery of short interfering RNA (siRNA) into mammalian cells," FEBS Lett., Jan. 2004, 558(1-3):63-68.
Nakase, I. et al., "Efficient Intracellular Delivery of Nucleic Acid Pharmaceuticals Using Cell-Penetrating Peptides," Acc. Chem. Res., 2012, 45(7):1132-1139.
Nakase, I. et al., "Interaction of arginine-rich peptides with membrane-associated proteoglycans is crucial for induction of actin organization and macropinocytosis," Biochemistry, 2007, 46:492-501.
Ngu-Schwemlein, M. et al., "In vitro synergy between some cationic amphipathic cyclooctapeptides and antibiotics," Australian Journal of Chemistry, 2015, 68(2):218-223.
Nischan, N. et al., "Covalent Attachment of Cyclic TAT Peptides to GFP Results in Protein Delivery into Live Cells with Immediate Bioavailability," Angew. Chem. Int. Ed., 2015, 54:1950-1953, with Supporting Information pp. S1-S26.
Nori, A. et al., "Tat-conjugated synthetic macromolecules facilitate cytoplasmic drug delivery to human ovarian carcinoma cells," Bioconjugate Chem., Jan.-Feb. 2003, 14(1):44-50.
Ocampo-Garcia, B. E. et al., "Design and biological evaluation of 99mTc-N2S2-Tat(49-57)-c(RGDyK): A hybrid radiopharmaceutical for tumors expressing a(v)(3) integrins," Nuclear Medicine and Biology (2013), 40(4):481-487.
Oh, D. et al., "Enhanced Cellular Uptake of Short Polyarginine Peptides through Fatty Acylation and Cyclization," Molecular Pharmaceutics, 2014, 11(8):2845-2854.
Oh, D. et al., "Amphiphilic Bicyclic Peptides as Cellular Delivery Agents," ChemMedChem, 2014, 9(11):2449-2453.
Oh, D. et al., "Antibacterial activities of amphiphilic cyclic cell-penetrating peptides against multidrug-resistant pathogens," Molecular Pharmaceutics, 2014, 11(10):3528-3536.
Okamoto, H. et al., "Conformational transitions of cyclic D,L-Peptides," Journal of Computational Chemistry, 2009, 30(6):962-973.
Palm-Apergi, C. et al., "The membrane repair response masks membrane disturbances caused by cell- penetrating peptide uptake," FASEB J., Jan. 2009, 23(1):214-223.
Pawson, T. et al., "Assembly of Cell Regulatory Systems Through Protein Interaction Domains," Science, Apr. 2003, 300(5618) :445-452.
Pham, W. et al., "Enhancing Membrane Permeability by Fatty Acylation of Oligoarginine Peptides," Chembiochem, Aug. 2004, 5(8): 1148-1151.
Pomilio, A B. et al., "Naturally-Occurring Cyclopeptides: Structures and Bioactivity," Current Organic Chemistry, Nov. 2006, 10(16):2075-2121.
Pooga, M. et al., "Cellular translocation of proteins by transportation," FASEB J., 2001, 15(8):1451-1453.
Pritz, S. et al., "Synthesis of Biologically Active Peptide Nucleic Acid-Peptide Conjugates by Sortase-Mediated Ligation," Journal of Organic Chemistry, 2007, 72(10):3909-3912.
Qian, Z. et al., "Discovery and Mechanism of Highly Efficient Cyclic Cell-Penetrating Peptides," Biochemistry, 2016, 55:2601-2612.
Qian, Z. et al., "Early endosomal escape of a cyclic cell-penetrating peptide allows effective cytosolic cargo delivery," Biochemistry, 2014, 53:4034-4046.
Qian, Z. et al., "Efficient delivery of cyclic peptides into mammalian cells with short sequence motifs," ACS Chem. Biol., 2013, 8:423-431.
Qian, Z. et al., "Intracellular Delivery of Peptidyl Ligands by Reversible Cyclization: Discovery of a PDZ Domain Inhibitor that Rescues CFTR Activity," Angew. Chem. Int. Ed., 2015, 54:5874-5878.
Qian, Z. et al., "Monitoring the cytosolic entry of cell-penetrating peptides using a pH-sensitive fluorophore," Chem. Commun., 2015, 51:2162-2165.
Qin, C. et al., "Optimization of Antibacterial Cyclic Decapeptides," J. Comb. Chem., 2004, 6(3):398-406.
Ren, L. et al., "Substrate Specificity of Protein Tyrosine Phosphatases 18, RPTPa, SHP-1, and SHP-2," Biochemistry, 2011, 50(12):2339-2356.
Rezai, T. et al., "Conformational Flexibility, Internal Hydrogen Bonding, and Passive Membrane Permeability: Successful in Silico Prediction of the Relative Permeabilities of Cyclic Peptides," J. Am. Chem. Soc., 2006, 128(43): 14073-14080.
Rezai, T. et al., "Testing the Conformational Hypothesis of Passive Membrane Permeability Using Synthetic Cyclic Peptide Diastereomers," J. Am. Chem. Soc., 2006, 128(8):2510-2511.
Richard, J. P. et al., "Cellular uptake of unconjugated TAT peptide involves clathrin-dependent endocytosis and heparan sulfate receptors," J. Biol. Chem., 2005, 280:15300-15306.

(56) References Cited

OTHER PUBLICATIONS

Ricouart, A et al., "Design of potent protein kinases inhibitors using the bisubstrate approach," Journal of Medicinal Chemistry, 1991, 34(1):73-78.
Riedl, S. J. et al., "Molecular mechanisms of caspase regulation during apoptosis," Nat. Rev. Mol. Cell Biol., Nov. 2004, 5:897-907.
Roberts, K. D. et al., "Efficient synthesis of thioether-based cyclic peptide libraries," Tetrahedron Letters, Nov. 1998, 39(45):8357-8360.
Roberts, K. E. et al., "Computational Design of a PDZ Domain Peptide Inhibitor that Rescues CFTR Activity," Plos Computational Biology, Apr. 2012, 8(4): e1002477,12 pages.
Rothbard, J. B. et al., "Conjugation of arginine oligomers to cyclosporin A facilitates topical delivery and inhibition of inflammation," Nature Medicine, 2000, 6(11):1253-1257.
Rotstein, B. H. et al., "Solvatochromic Reagents for Multicomponent Reactions and their Utility in the Development of Cell-Permeable Macrocyclic Peptide Vectors," 2011, Chem. Eur. J., 17:12257-12261.
Rueping, M. et al., "Cellular Uptake Studies with beta-Peptides," ChemBioChem, Mar. 2002, 3(2-3):257-259.
Rusnati, M. et al., "Multiple Interactions of HIV-I Tat Protein with Size-defined Heparin Oligosaccharides," J. Biol. Chem., Oct. 1999, 274(40):28198-28205.
Saar, K. et al., "Cell-penetrating peptides: A comparative membrane toxicity study," Anal. Biochem., 2005, 345:55-65.
Sako, Y. et al., "Ribosomal synthesis of bicyclic peptides via two orthogonal inter-side-chain reactions," J. Am. Chem. Soc., Jun. 2008, 130(23):7232-7234.
Salvado, I. et al., "Membrane-disrupting iridium(111) oligocationic organometallopeptides," Chemical Communications, 2016, 52(73): 11008-11011.
Schafmeister, C. E. et al., "An All-Hydrocarbon Cross-Linking System for Enhancing the Helicity and Metabolic Stability of Peptides," J. Am. Chem. Soc., 2000, 122(24):5891-5892.
Schmidt, N. et al., "Arginine-rich cell-penetrating peptides," FEBS Lett., 2010, 584: 1806-1813.
Schwarze, S. R. et al., "In vivo protein transduction: delivery of a biologically active protein into the mouse," Science, Sep. 1999, 285(5433):1569-1572.
Scott, C. P. et al., "Production of cyclic peptides and proteins in vivo," Proc. Natl. Acad. Sci. U. S. A., Nov. 1999, 96(24):13638-13643.
Shirazi, A. N. et al, "Cysteine and arginine-rich peptides as molecular carriers," Bioorg. Med. Chem. Lett., 2016, 26:656-661.
Shirazi, A. N. et al., "Cyclic Peptide-Capped Gold Nanoparticles as Drug Delivery Systems," Molecular Pharmaceutics, 2013, 11:500-511.
Shirazi, A. N. et al., "Design and Biological Evaluation of Cell-Penetrating Peptide-Doxorubicin Conjugates as Prodrugs," Molecular Pharmaceutics, 2013, 10:488-499.
Shirazi, A. N. et al, "Cyclic peptides containing tryptophan and arginine as Src kinase inhibitors", Bioorganic & Medicinal Chemistry Letters 23 (2013) 3230-3234.
Slee, E. A. et al., "Benzyloxycarbonyl-Val-Ala-Asp (OMe) fluoromethylketone (Z-VAD.FMK) inhibits apoptosis by blocking the processing of CPP32," Biochemical Journal, Apr. 1996, 315(1):21-24.
Songyang, Z. et al., "Recognition of Unique Carboxyl-Terminal Motifs by Distinct PDZ Domains," Science, Jan. 1997, 275(5296):73-77.
Stanford, S. M. et al., "High-throughput screen using a single-cell tyrosine phosphatase assay reveals biologically active inhibitors of tyrosine phosphatase CD45," Proc. Natl. Acad. Sci. U. S. A., Aug. 2012, 109(35):13972-13977.
Stewart, J. M. et al., "Bradykinin antagonists: Anti-cancer drugs for the new millennium?" Peptides for the New Millennium, Proceedings of the American Peptide Symposium, 16th, Minneapolis, MN, United States, Jun. 26-Jul. 1, 1999 (2000), Meeting Date 1999, 219-221. Fields, G. B. et al., (eds.), Kluwer Academic Publishers, Dordrecht, Neth.
Stewart, K. M. et al., "Cell-penetrating peptides as delivery vehicles for biology and medicine," Org. Biomol. Chem., Jul. 2008, 6(13):2242-2255.
Suhorutsenko, J. et al., "Cell-penetrating peptides, PepFects, show no evidence of toxicity and immunogenicity in vitro and in vivo," Bioconjugate Chem., Nov. 2011, 22(11):2255-2262.
Sun, Y. et al., "A thioester ligation approach to amphipathic bicyclic peptide library," Org. Lett., May 2001, 3(11):1681-1684.
Tam, J. P. et al., "Disulfide bond formation in peptides by dimethyl sulfoxide. Scope and applications," J. Am. Chem. Soc., 1991, 113(17):6657-6662.
Tavassoli, A. et al., "Inhibition of HIV Budding by a Genetically Selected Cyclic Peptide Targeting the Gag-TSG101 Interaction," ACS Chemical Biology, 2008, 3(12):757-764.
Thakkar, A. et al., "Traceless Capping Agent for Peptide Sequencing by Partial Edman Degradation and Mass Spectrometry," Anal. Chem., 2006, 78(16):5935-5939.
Thornberry, N. A. et al., "A Combinatorial Approach Defines Specificities of Members of the Caspase Family and Granzyme B. Functional Relationships Established for Key Mediators of Apoptosis," J. Biol. Chem., Jul. 1997, 272(29):17907-17911.
Traboulsi, H. et al., "Macrocyclic Cell Penetrating Peptides: A Study of Structure-Penetration Properties," Bioconjugate Chemistry, 2015, 26:405-411.
Trinh, T. B. et al., "Discovery of a Direct Ras Inhibitor by Screening a Combinatorial Library of Cell-Permeable Bicyclic Peptides," ACS Comb Sci., 2016, 18:75-85. Published Online: Dec. 8, 2015.
Tse, B. N. et al., "Translation of DNA into a Library of 13 000 Synthetic Small-Molecule Macrocycles Suitable for in Vitro Selection," J. Am. Chem. Soc., 2008, 130(46):15611-15626.
Turner, R. A. et al., "Click chemistry as a macrocyclization tool in the solid-phase synthesis of small cyclic peptides," Org. Lett., Nov. 2007, 9(24): 50115014. Epub Oct. 23, 2007.
Tyagi, M. et al., "Internalization of HIV-1 Tat requires cell surface heparan sulfate proteoglycans," J. Biol. Chem., Feb. 2001, 276(5):3254-3261. Epub Oct. 6, 2000.
Upadhyaya, P. et al., "Inhibition of Ras signaling by blocking Ras-effector interactions with cyclic peptide," Angew. Chem. Int. Ed., May 2015, 54:7602-7606. Published Online: May 7, 2015.
Van Goor, F. et al., "Correction of the F508del-CFTR protein processing defect in vitro by the investigational drug VX-809," Proc. Natl. Acad. Sci. U. S. A., Nov. 2011, 108(46):18843-18848.
Varkouhi, A. K. et al., "Endosomal escape pathways for delivery of biologicals," J. Controlled Release, May 2011, 151(3):220-228. Epub Nov. 13, 2010.
Wadia, J. S. et al., "Transmembrane delivery of protein and peptide drugs by TAT-mediated transduction in the treatment of cancer," Advanced Drug Delivery Reviews, Feb. 2005, 57(4):579-596. Epub Dec. 19, 2004.
Wallbrecher, R. et al., "Exploration of the Design Principles of a Cell-Penetrating Bicylic Peptide Scaffold," Bioconjugate Chemistry, 2014, 25(5):955-964. Published Online: Apr. 3, 2014.
Wang, C-W. et al., "Increased potency of a novel D-beta-naphthylalanine-substituted antimicrobial peptide against fluconazole-resistant fungal pathogens," FEMS Yeast Research, 2009, 9(6):967-970.
Wender, P. A. et al., "The design, synthesis, and evaluation of molecules that enable or enhance cellular uptake: Peptoid molecular transporters," Proc. Natl. Acad. Sci. U. S. A., Nov. 2000, 97(24):13003-13008.
White, T. R. et al., "On-resin N-methylation of cyclic peptides for discovery of orally bioavailable scaffolds," Nat. Chem. Biol., Sep. 2011, 7(11): 810-817.
Wolde, M. et al., "Targeting CAL as a negative regulator of DeltaF508-CFTR cell-surface expression: an RNA interference and structure-based mutagenetic approach," J. Biol. Chem., Mar. 2007, 282(11):8099-8109. Epub Dec. 11, 2006.

(56) References Cited

OTHER PUBLICATIONS

Wu, G. et al., "Structural basis of IAP recognition by Smac/DIABLO," Nature, Dec. 2000, 408(6815):1008-1012.
Wu, X. et al., "Inhibition of Ras-effector interactions by cyclic peptides," Med. Chem. Commun., 2013, 4:378-382. Published Online: Nov. 27, 2012.
Xie, L. et al., "Cellular Effects of Small Molecule PTP1B Inhibitors on Insulin Signaling," Biochemistry, 2003, 42(44):12792-12804.
Yin, J. et al., "Genetically encoded short peptide tag for versatile protein labeling by Sfp phosphopantetheinyl transferase," Proc. Natl. Acad. Sci. U. S. A., Nov. 2005, 102(44): 15815-15820.
Zabolotny, J. M. et al., "PTP1B regulates leptin signal transduction in vivo," Dev. Cell, Apr. 2002, 2(4):489-495.
Zhao, K. et al., "Enhanced activity of cyclic transporter sequences driven by phase behavior of peptide-liquid complexes," Soft Matter, 2012, 8(24): 6430-6433.
Ziegler, A. et al., "Interaction of the protein transduction domain of HIV-1 TAT with heparan sulfate: binding mechanism and thermodynamic parameters," Biophys. J., Jan. 2004, 86(1):254-263.
Ziegler, A., "Thermodynamic studies and binding mechanisms of cell-penetrating peptides with lipids and glycosaminoglycans," Advanced Drug Delivery Reviews, Mar. 2008, 60(4-5):580-597. Epub Oct. 22, 2007.
International Search Report and Written Opinion for International Application No. PCT/US2015/032043, dated Jan. 14, 2016, 11 pages.
International Preliminary Report on Patentability for International Application No. PCT/US2015/032043, dated Nov. 22, 2016, 8 pages.
Extended European Search Report issued for Application No. 15796259.8, dated Jan. 22, 2018, 6 pages.
Extend European Search Report issued for Application No. 15835788.9, dated Jun. 1, 2018.
Choi et al. "Cell permeable NFAT inhibitory peptide Sim-2-VIVIT inhibits sT-cell activation and alleviates allergic airways inflammation and hyper-responsiveness", Immunology Letters 143:2 pp. 170-176.
Karpurapu, et al., "Inhibition of nuclear factor of activated T cells (NFAT) c3 activation attenuates acute lung injury and pulmonary edema in murine models of sepsis", Oncotarget 9(12), pp. 10606-10620.
Liao et al., Cell-premeable bicyclic peptidyl inhibitors against T-cell protein tyrosine phosphates from a combinatorial library, Organic & Biomolecular Chemistry, vol. 15, pp. 9595-9598, 2017.
Majer et al., Structure-based subsite specificity mapping of human cathespin D using statine-based inhibitors, Protein Science, vol. 6, pp. 1458-1466, 1997.

* cited by examiner

CP9-ZIZIT

CP9-VAVAA

CP9-ZIZIT-Biotin

CP9-VAVAA-Biotin

SEQUENCE LISTING

```
<160> NUMBER OF SEQ ID NOS: 47

<210> SEQ ID NO 1
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: Pro or a Pro analogue

<400> SEQUENCE: 1

Xaa Ile Xaa Ile Thr Xaa Xaa
1               5


<210> SEQ ID NO 2
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an
      S-alkylated derivative of L-penicillamine
```

<220> FEATURE:
<221> NAME/KEY: MISC_FEATURE
<222> LOCATION: (7)..(7)
<223> OTHER INFORMATION: Pro or a Pro analogue

<400> SEQUENCE: 2

Xaa Ile Xaa Ile Thr Gly Xaa
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: tert-leucine
<220> FEATURE:
<221> NAME/KEY: MISC_FEATURE
<222> LOCATION: (7)..(7)
<223> OTHER INFORMATION: tert-leucine

<400> SEQUENCE: 3

Gly Pro His Pro Xaa Ile Xaa Ile Thr Gly Pro His Glu Glu
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: tert-leucine
<220> FEATURE:
<221> NAME/KEY: MISC_FEATURE
<222> LOCATION: (7)..(7)
<223> OTHER INFORMATION: tert-leucine
<220> FEATURE:
<221> NAME/KEY: MISC_FEATURE
<222> LOCATION: (11)..(11)
<223> OTHER INFORMATION: dimethylthiazolidine-4-carboxylic acid

<400> SEQUENCE: 4

Gly Pro His Pro Xaa Ile Xaa Ile Thr Gly Xaa His Glu Glu
1               5                   10

<210> SEQ ID NO 5
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: any amino acid
<220> FEATURE:
<221> NAME/KEY: MISC_FEATURE
<222> LOCATION: (4)..(4)
<223> OTHER INFORMATION: any amino acid

<400> SEQUENCE: 5

Pro Xaa Ile Xaa Ile Thr
1               5

```
<210> SEQ ID NO 6
<211> LENGTH: 14
<212> TYPE: PRT
<213> ORGANISM: Artificial Sequence
<220> FEATURE:
<223> OTHER INFORMATION: Synthetic construct

<400> SEQUENCE: 6

Gly Pro His Ala Val Ala Val Ala Ala Gly Pro His Glu Glu
1               5                   10


<210> SEQ ID NO 7
<211> LENGTH: 12
<212> TYPE: PRT
<213> ORGANISM: Artificial Sequence
<220> FEATURE:
<223> OTHER INFORMATION: Synthetic construct

<400> SEQUENCE: 7

Arg Arg Arg Arg Arg Arg Arg Arg Arg Arg Arg Cys
1               5                   10


<210> SEQ ID NO 8
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 8

Phe Xaa Arg Arg Arg Gln
1               5


<210> SEQ ID NO 9
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 9

Phe Xaa Arg Arg Arg Cys
1               5


<210> SEQ ID NO 10
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine
<220> FEATURE:
<221> NAME/KEY: MISC_FEATURE
<222> LOCATION: (6)..(6)
<223> OTHER INFORMATION: selenocysteine

<400> SEQUENCE: 10

Phe Xaa Arg Arg Arg Xaa
1               5
```

<210> SEQ ID NO 11
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (4)..(4)
<223> OTHER INFORMATION: L-naphthylalanine

<400> SEQUENCE: 11

Arg Arg Arg Xaa Phe Gln
1               5

<210> SEQ ID NO 12
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: L-naphthylalanine

<400> SEQUENCE: 12

Arg Arg Arg Arg Xaa Phe
1               5

<210> SEQ ID NO 13
<211> LENGTH: 6
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 13

Phe Xaa Arg Arg Arg Arg
1               5

<210> SEQ ID NO 14
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: D-naphthylalanine

<400> SEQUENCE: 14

Phe Xaa Arg Arg Arg Arg Gln
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: D-naphthylalanine -continued

<400> SEQUENCE: 15

Phe Xaa Arg Arg Arg Arg Gln
1 5

<210> SEQ ID NO 16
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 16

Phe Xaa Arg Arg Arg Arg Gln
1 5

<210> SEQ ID NO 17
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: L-naphthylalanine

<400> SEQUENCE: 17

Xaa Xaa Arg Arg Arg Arg Gln
1 5

<210> SEQ ID NO 18
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: L-naphthylalanine

<400> SEQUENCE: 18

Arg Arg Phe Arg Xaa Arg Gln
1 5

<210> SEQ ID NO 19
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: L-naphthylalanine

<400> SEQUENCE: 19

Phe Arg Arg Arg Arg Xaa Gln
1 5

-continued

<210> SEQ ID NO 20
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: L-naphthylalanine

<400> SEQUENCE: 20

Arg Arg Phe Arg Xaa Arg Gln
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-naphthylalanine

<400> SEQUENCE: 21

Arg Arg Xaa Phe Arg Arg Gln
1               5

<210> SEQ ID NO 22
<211> LENGTH: 8
<212> TYPE: PRT
<213> ORGANISM: Artificial Sequence
<220> FEATURE:
<223> OTHER INFORMATION: Synthetic construct

<400> SEQUENCE: 22

Cys Arg Arg Arg Arg Phe Trp Gln
1               5

<210> SEQ ID NO 23
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: D-phenylalanine
<220> FEATURE:
<221> NAME/KEY: MISC_FEATURE
<222> LOCATION: (3)..(3)
<223> OTHER INFORMATION: L-naphthylalanine

<400> SEQUENCE: 23

Phe Xaa Xaa Arg Arg Arg Arg Gln
1               5

<210> SEQ ID NO 24
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (3)..(3)
<223> OTHER INFORMATION: L-naphthylalanine -continued

<400> SEQUENCE: 24

Phe Phe Xaa Arg Arg Arg Arg Gln
1               5

<210> SEQ ID NO 25
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (6)..(6)
<223> OTHER INFORMATION: L-naphthylalanine

<400> SEQUENCE: 25

Arg Phe Arg Phe Arg Xaa Arg Gln
1               5

<210> SEQ ID NO 26
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: selenocysteine

<400> SEQUENCE: 26

Xaa Arg Arg Arg Arg Phe Trp Gln
1               5

<210> SEQ ID NO 27
<211> LENGTH: 8
<212> TYPE: PRT
<213> ORGANISM: Artificial Sequence
<220> FEATURE:
<223> OTHER INFORMATION: Synthetic construct

<400> SEQUENCE: 27

Cys Arg Arg Arg Arg Phe Trp Gln
1               5

<210> SEQ ID NO 28
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 28

Phe Xaa Arg Arg Arg Arg Gln Lys
1               5

<210> SEQ ID NO 29
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 29

Phe Xaa Arg Arg Arg Arg Gln Cys
1               5

<210> SEQ ID NO 30
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: D-phenylalanine
<220> FEATURE:
<221> NAME/KEY: MISC_FEATURE
<222> LOCATION: (2)..(2)
<223> OTHER INFORMATION: L-naphthylalanine

<400> SEQUENCE: 30

Xaa Xaa Arg Arg Arg Arg Arg Gln
1               5

<210> SEQ ID NO 31
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: L-naphthylalanine

<400> SEQUENCE: 31

Phe Xaa Arg Arg Arg Arg Arg Gln
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (5)..(5)
<223> OTHER INFORMATION: L-naphthylalanine
<220> FEATURE:
<221> NAME/KEY: MISC_FEATURE
<222> LOCATION: (8)..(8)
<223> OTHER INFORMATION: L-norleucine

<400> SEQUENCE: 32

Arg Arg Arg Arg Xaa Phe Asp Xaa Cys
1               5

<210> SEQ ID NO 33
<211> LENGTH: 8
<212> TYPE: PRT
<213> ORGANISM: Artificial Sequence
<220> FEATURE:
<223> OTHER INFORMATION: Synthetic construct

```
<220> FEATURE:
<221> NAME/KEY: MISC_FEATURE
<222> LOCATION: (2)..(2)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: Pro or a Pro analogue

<400> SEQUENCE: 33

Pro Xaa Ile Xaa Ile Thr Xaa Xaa
1               5


<210> SEQ ID NO 34
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: Pro or a Pro analogue

<400> SEQUENCE: 34

Xaa Ile Xaa Ile Thr Xaa Xaa His
1               5


<210> SEQ ID NO 35
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (7)..(7)
<223> OTHER INFORMATION: any amino acid
```

<220> FEATURE:
<221> NAME/KEY: MISC_FEATURE
<222> LOCATION: (8)..(8)
<223> OTHER INFORMATION: Pro or a Pro analogue

<400> SEQUENCE: 35

Pro Xaa Ile Xaa Ile Thr Xaa Xaa His
1 5

<210> SEQ ID NO 36
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: Pro or a Pro analogue

<400> SEQUENCE: 36

Xaa Ile Xaa Ile Thr Xaa Xaa His Glu
1 5

<210> SEQ ID NO 37
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: Pro or a Pro analogue

<400> SEQUENCE: 37

Pro Xaa Ile Xaa Ile Thr Xaa Xaa His Glu
1 5 10

<210> SEQ ID NO 38
<211> LENGTH: 10
<212> TYPE: PRT
<213> ORGANISM: Artificial Sequence
<220> FEATURE:
<223> OTHER INFORMATION: Synthetic construct -continued
<220> FEATURE:
<221> NAME/KEY: MISC_FEATURE
<222> LOCATION: (1)..(1)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: Pro or a Pro analogue

<400> SEQUENCE: 38

Xaa Ile Xaa Ile Thr Xaa Xaa His Glu Glu
1 5 10

<210> SEQ ID NO 39
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: Pro or a Pro analogue

<400> SEQUENCE: 39

Pro Xaa Ile Xaa Ile Thr Xaa Xaa His Glu Glu
1 5 10

<210> SEQ ID NO 40
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (7)..(7)
<223> OTHER INFORMATION: any amino acid -continued
<220> FEATURE:
<221> NAME/KEY: MISC_FEATURE
<222> LOCATION: (8)..(8)
<223> OTHER INFORMATION: dimethylthiazolidine-4-carboxylic acid

<400> SEQUENCE: 40

Pro Xaa Ile Xaa Ile Thr Xaa Xaa
1 5

<210> SEQ ID NO 41
<211> LENGTH: 8
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: dimethylthiazolidine-4-carboxylic acid

<400> SEQUENCE: 41

Xaa Ile Xaa Ile Thr Xaa Xaa His
1 5

<210> SEQ ID NO 42
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an S-alkylated derivative of L-penicillamine
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: dimethylthiazolidine-4-carboxylic acid

<400> SEQUENCE: 42

Pro Xaa Ile Xaa Ile Thr Xaa Xaa His
1 5

<210> SEQ ID NO 43
<211> LENGTH: 9
<212> TYPE: PRT
<213> ORGANISM: Artificial Sequence
<220> FEATURE:
<223> OTHER INFORMATION: Synthetic construct -continued
<220> FEATURE:
<221> NAME/KEY: MISC_FEATURE
<222> LOCATION: (1)..(1)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (6)..(6)
<223> OTHER INFORMATION: any amino acid
<220> FEATURE:
<221> NAME/KEY: MISC_FEATURE
<222> LOCATION: (7)..(7)
<223> OTHER INFORMATION: dimethylthiazolidine-4-carboxylic acid

<400> SEQUENCE: 43

Xaa Ile Xaa Ile Thr Xaa Xaa His Glu
1 5

<210> SEQ ID NO 44
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: dimethylthiazolidine-4-carboxylic acid

<400> SEQUENCE: 44

Pro Xaa Ile Xaa Ile Thr Xaa Xaa His Glu
1 5 10

<210> SEQ ID NO 45
<211> LENGTH: 10
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (1)..(1)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (3)..(3)
<223> OTHER INFORMATION: tert-leucine, L-penicillamine, or an
S-alkylated derivative of L-penicillamine
<220> FEATURE:
<221> NAME/KEY: MISC_FEATURE
<222> LOCATION: (6)..(6)
<223> OTHER INFORMATION: any amino acid -continued

```
<220> FEATURE:
<221> NAME/KEY: MISC_FEATURE
<222> LOCATION: (7)..(7)
<223> OTHER INFORMATION: dimethylthiazolidine-4-carboxylic acid

<400> SEQUENCE: 45

Xaa Ile Xaa Ile Thr Xaa Xaa His Glu Glu
1               5                   10


<210> SEQ ID NO 46
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: MISC_FEATURE
<222> LOCATION: (2)..(2)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (4)..(4)
<223> OTHER INFORMATION: tert-leucine, L-penicillamine, or an
      S-alkylated derivative of L-penicillamine
<220> FEATURE:
<221> NAME/KEY: MISC_FEATURE
<222> LOCATION: (7)..(7)
<223> OTHER INFORMATION: any amino acid
<220> FEATURE:
<221> NAME/KEY: MISC_FEATURE
<222> LOCATION: (8)..(8)
<223> OTHER INFORMATION: dimethylthiazolidine-4-carboxylic acid

<400> SEQUENCE: 46

Pro Xaa Ile Xaa Ile Thr Xaa Xaa His Glu Glu
1               5                   10


<210> SEQ ID NO 47
<211> LENGTH: 14
<212> TYPE: PRT
<213> ORGANISM: Artificial Sequence
<220> FEATURE:
<223> OTHER INFORMATION: Synthetic construct

<400> SEQUENCE: 47

Gly Pro His Pro Val Ile Val Ile Thr Gly Pro His Glu Glu
1               5                   10
```

PEPTIDYL CALCINEURIN INHIBITORS

CROSS-REFERENCE TO RELATED APPLICATIONS

This application is a national stage application field under 35 U.S.C. § 371 of PCT/US2015/047267 filed Aug. 27, 2015, which claims benefit of U.S. Provisional Application No. 62/042,715, filed Aug. 27, 2014, which is hereby incorporated herein by reference in its entirety.

STATEMENT REGARDING FEDERALLY SPONSORED RESEARCH OR DEVELOPMENT

This invention was made with Government Support under Grant Nos. GM062820 and CA132855 awarded by the National Institutes of Health. The Government has certain rights in the invention.

BACKGROUND

The cyclosporins comprise a class of structurally distinctive, cyclic, poly-N-methylated undecapeptides, commonly possessing pharmacological, in particular immunosuppressive, anti-inflammatory and antiparasitic activity. The first of the cyclosporins to be isolated was the naturally occurring fungal metabolite Ciclosporin or Cyclosporin, also known as cyclosporin A. Cyclosporine A has found wide use since its introduction in the fields of organ transplantation and immunomodulation, and has brought about a significant increase in the success rate for transplantation procedures. However, side effects with systemic cyclosporin A include increase in diastolic blood pressure, decrease in renal function, hepatic dysfunction, hypertrichosis, tremor, gingival hyperplasis and paraesthsia. The systemic toxicity of cyclosporin A limits its use for the treatment of certain diseases. Accordingly, a need exists for compounds which exhibit immunosuppressive activity while not producing systemic toxicity.

SUMMARY

In accordance with the purposes of the disclosed subject matter, as embodied and broadly described herein, this disclosure, in one aspect, relates to improved calcineurin inhibitors and methods of using these improved calcineurin inhibitors to inhibit calcineurin-NFAT signaling in cells and in subjects.

DESCRIPTION OF DRAWINGS

FIG. 2A is a plot of fluorescence anisotropy of FITC-labeled peptides (100 nM) as a function of CN concentration. FIG. 2B is a plot of FA of FITC-labeled ZIZIT (100 nM) in the presence of CN (150 nM) and unlabeled peptides VIVIT, ZIZIT, or ZIZIT-cisPro (0-20 μM) as a function of the competing peptide concentration. Data reported were the mean±SD from three independent experiments. The FA values in FIG. 2B were relative to that in the absence of competing peptide.

Figure 5A:
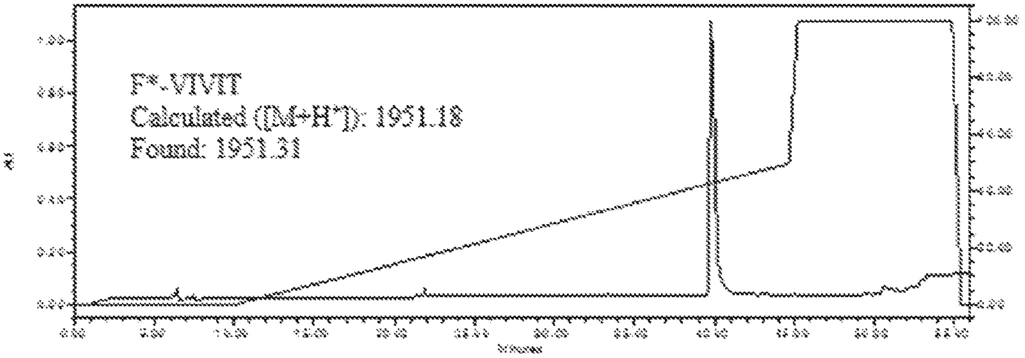
FIGS. 5A to 5C show HPLC and MS analysis of peptides (SEQ ID NO: 47
F*-GPHPVIVITGPHEE-$NH_2$ ("F*-VIVIT")
Figure 5B:
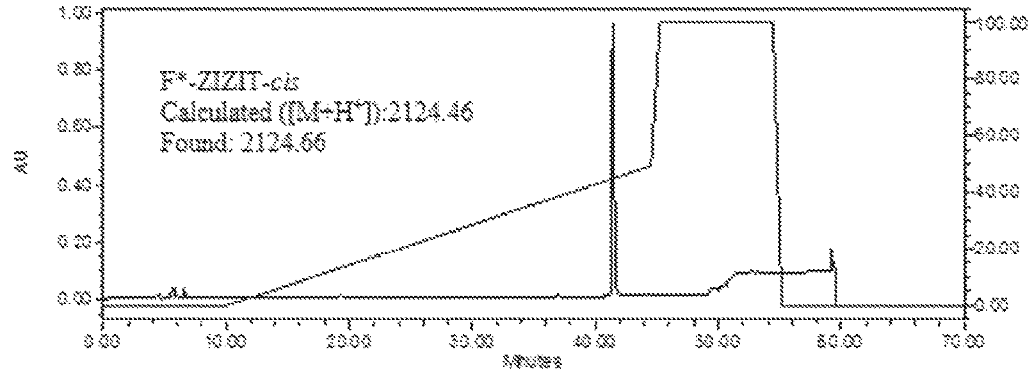
Figure 5C:
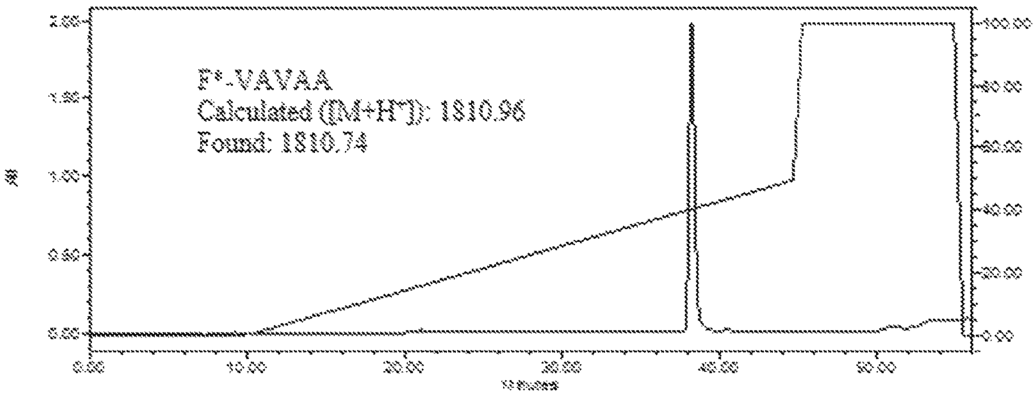
Figure 5D:
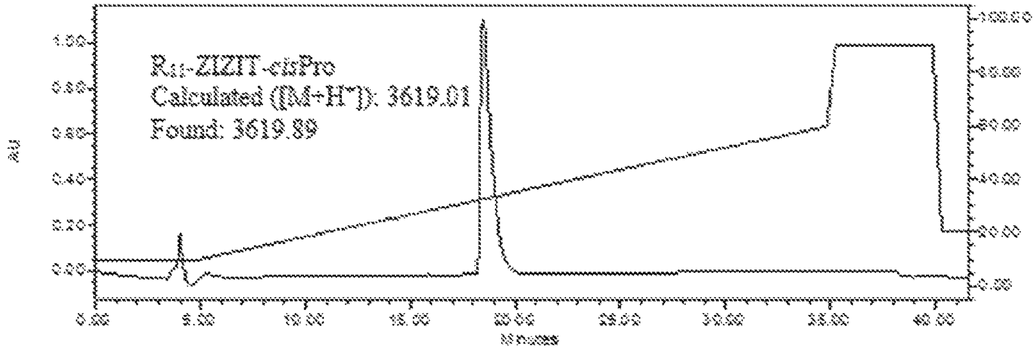
Figure 5E:
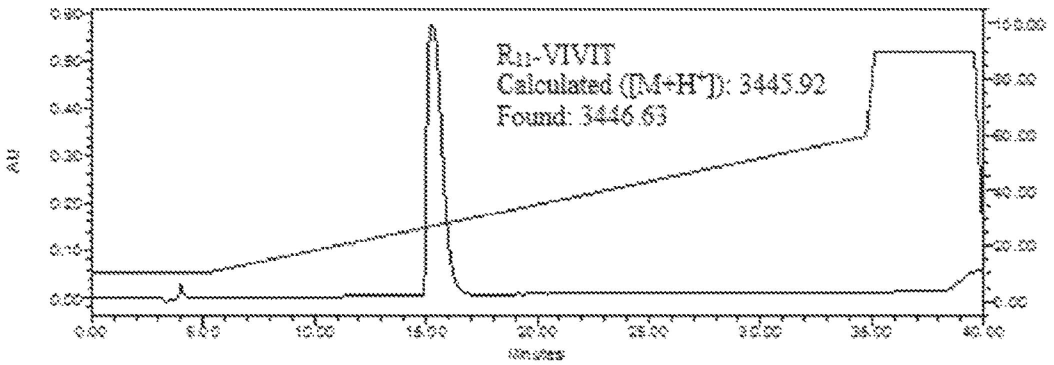
Figure 5F:
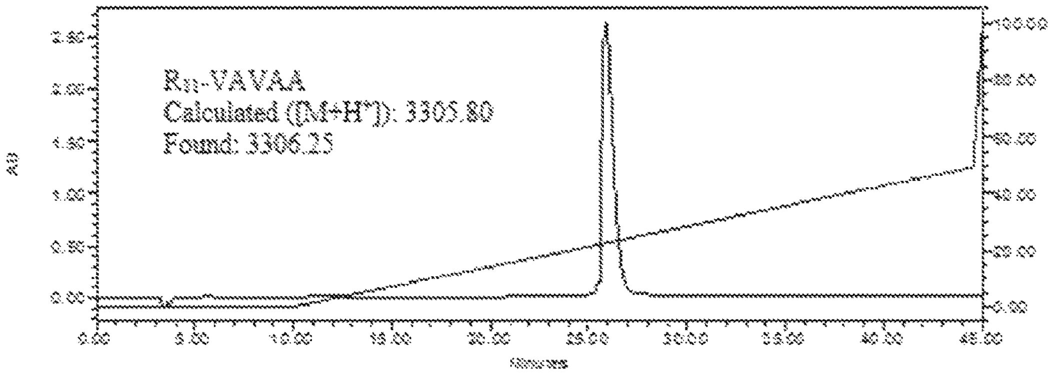
Figure 6A:
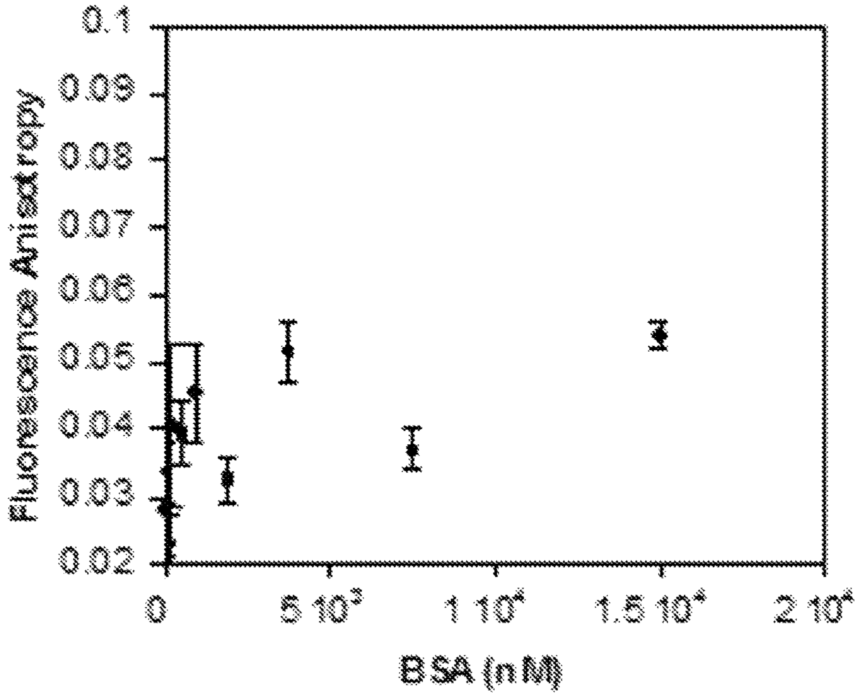
Figure 6B:
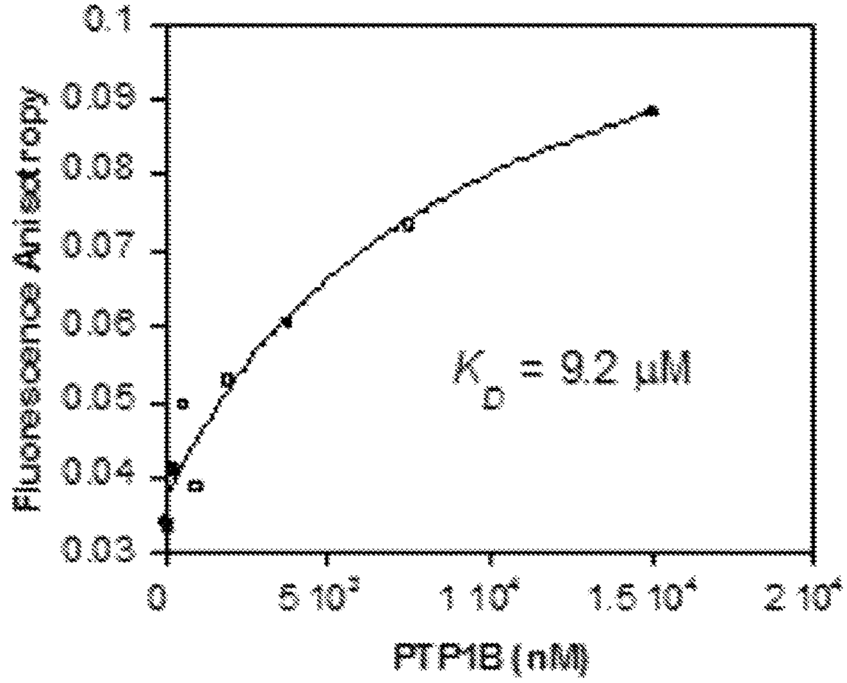
Figure 6C:
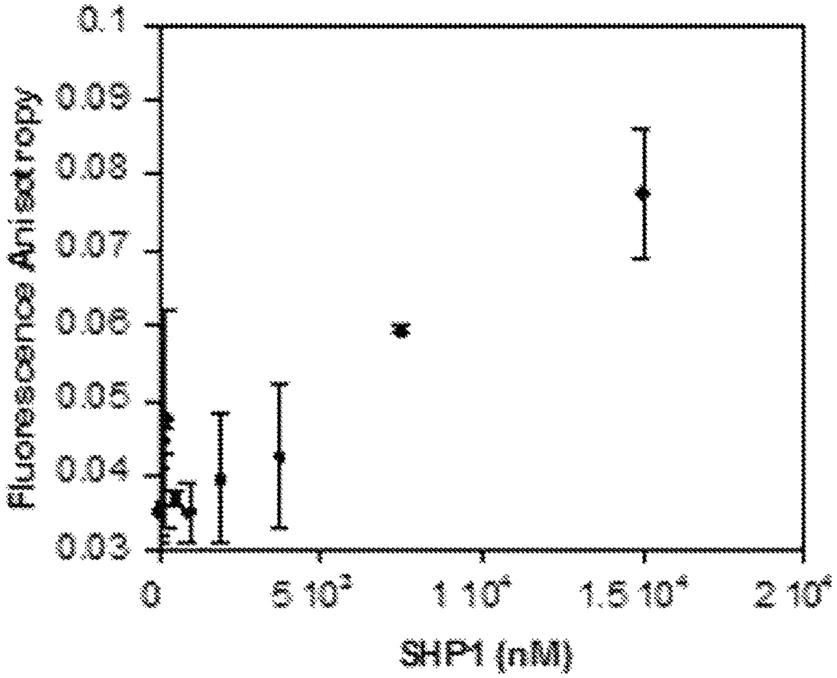
Figure 6D:
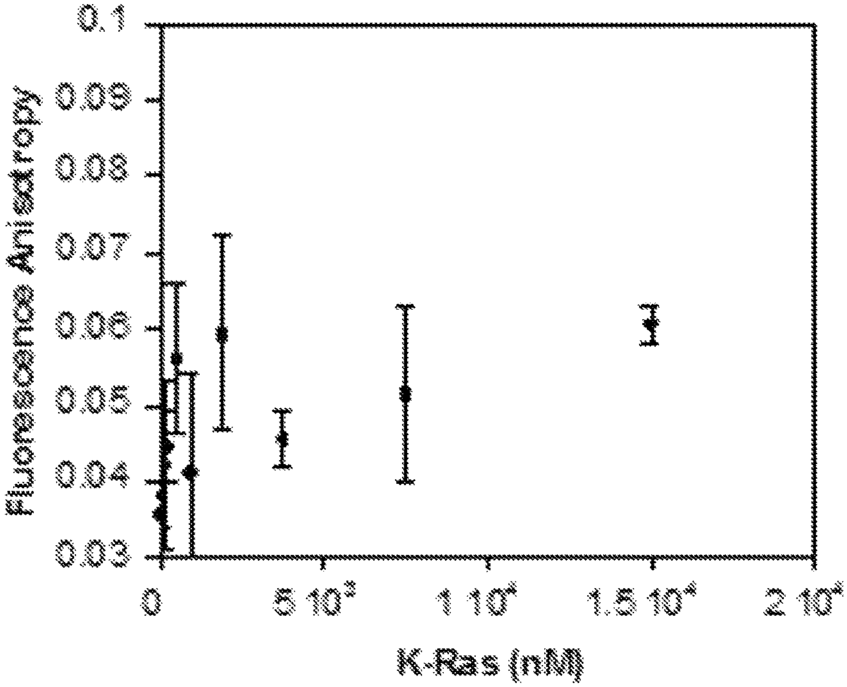
Figure 6E:
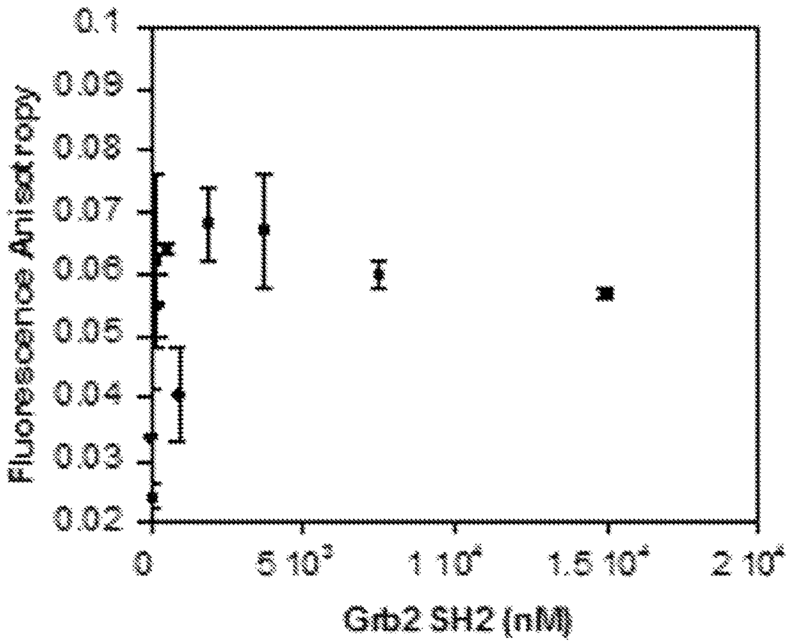

for underlined portion) (FIG. 5A), (SEQ ID NO: 4
F*-GPHPZIZITG-Cys($\Psi^{Me,Me}$Pro)-HEEG-Propyl
("F*-ZIZIT-cis")

for underlined portion) (FIG. 5B), (SEQ ID NO: 6
F*-GPHAVAVAAGPHEE-$NH_2$ ("F*-VAVAA")

for underlined portion) (FIG. 5C), (SEQ ID NO: 4
Ac-*RRRRRRRRRRRC*-SPDP-GPHPZIZITG-
Cys($\Psi^{Me,Me}$Pro)-HEEG-Propyl ("$R_{11}$-ZIZIT-cisPro")

for underlined portion; SEQ ID NO:7 for italicized portion) (FIG. 5D), (SEQ ID NO: 47
Ac-*RRRRRRRRRRRC*-SPDP-GPHPVIVITGPHEE-$NH_2$
("$R_{11}$-VIVIT")

for underlined portion; SEQ ID NO:7 for italicized portion) (FIG. 5E), and (SEQ ID NO: 6
Ac-*RRRRRRRRRRRC*-SPDP-GPHAVAVAAGPHEE-$NH_2$
("$R_{11}$-VAVAA")

for underlined portion; SEQ ID NO:7 for italicized portion) (FIG. 5F). The purity of the product (>98%) was assessed by reversed-phase HPLC equipped with an analytical $C_{18}$ column. The purities and authenticities of the peptides were also confirmed by MALDI-TOF MS analysis. F*, 5(6)-SFX.

FIGS. 6A to 6E show binding (or lack of binding) of FITC-labeled ZIZIT-cisPro (100 nM) to bovine serum albumin (BSA) (FIG. 6A), protein-tyrosine phosphatases 1B (PTP1B) (FIG. 6B) and SHP1 (FIG. 6C), small GTPase K-Ras G12V (FIG. 6D), and Grb2 $SH_2$ domain (FIG. 6E) as assayed by fluorescence anisotropy.

Figure 7:
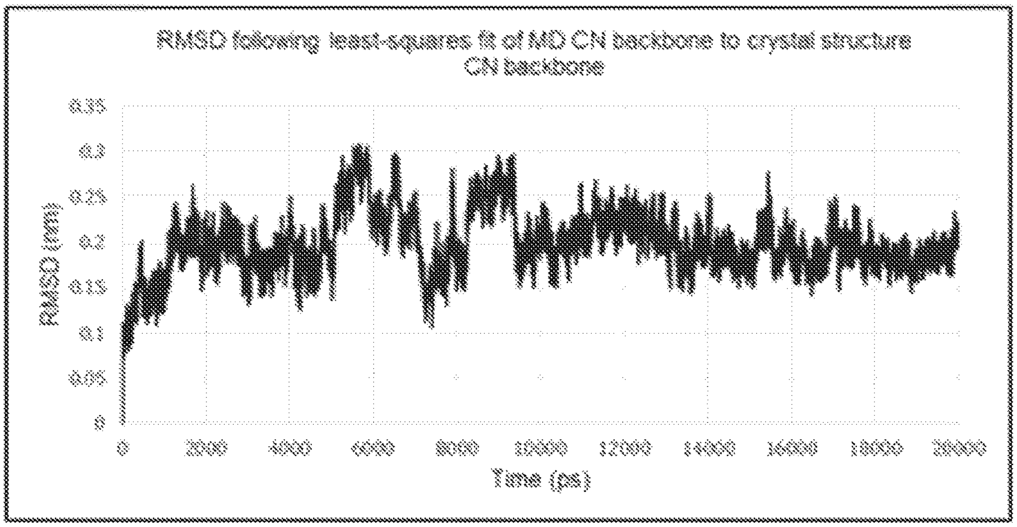

FIG. 7 shows RMSD values generated by the GROMACS program "g—rms" following a least-squares fit of calcineurin bound with ZIZIT-cisPro structure over the 20 ns MD trajectory to the crystal structure of a calineurin-VIVIT complex (pdbID: 2P6B).

Figure 8:
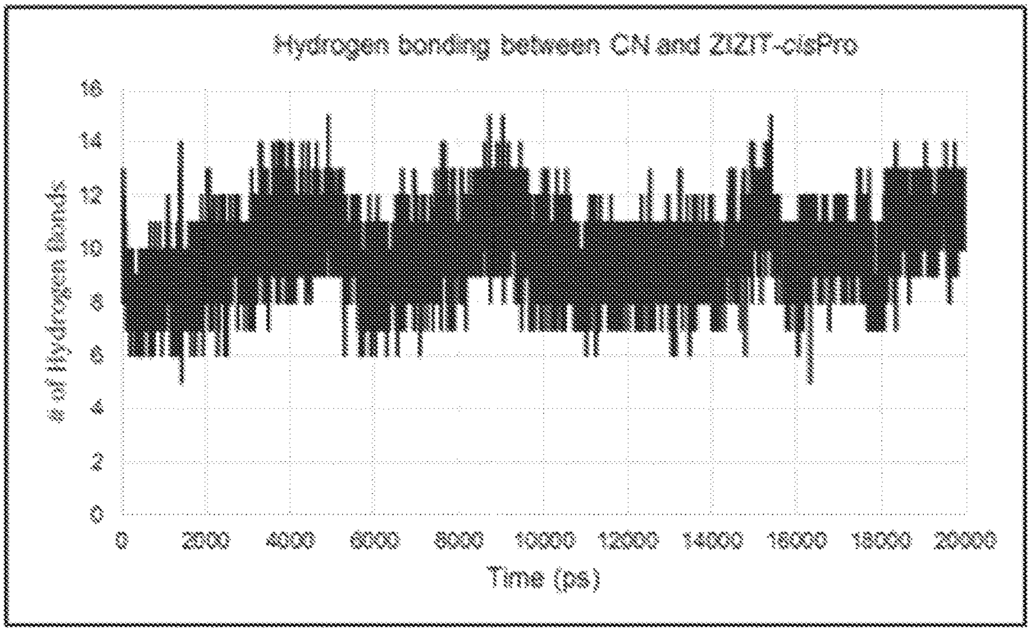

FIG. 8 shows hydrogen bonding interactions between CN and ZIZIT-cisPro, calculating in GROMACS using g_hbond with the standard cutoff distances and angle requirements.

Figure 9:
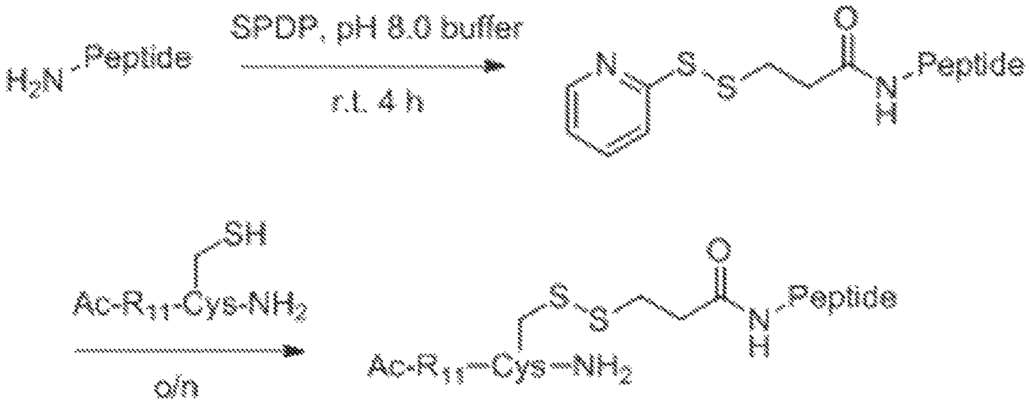

FIG. 9 shows preparation of $R_{11}$ conjugated CN inhibitors.

Figure 10A:
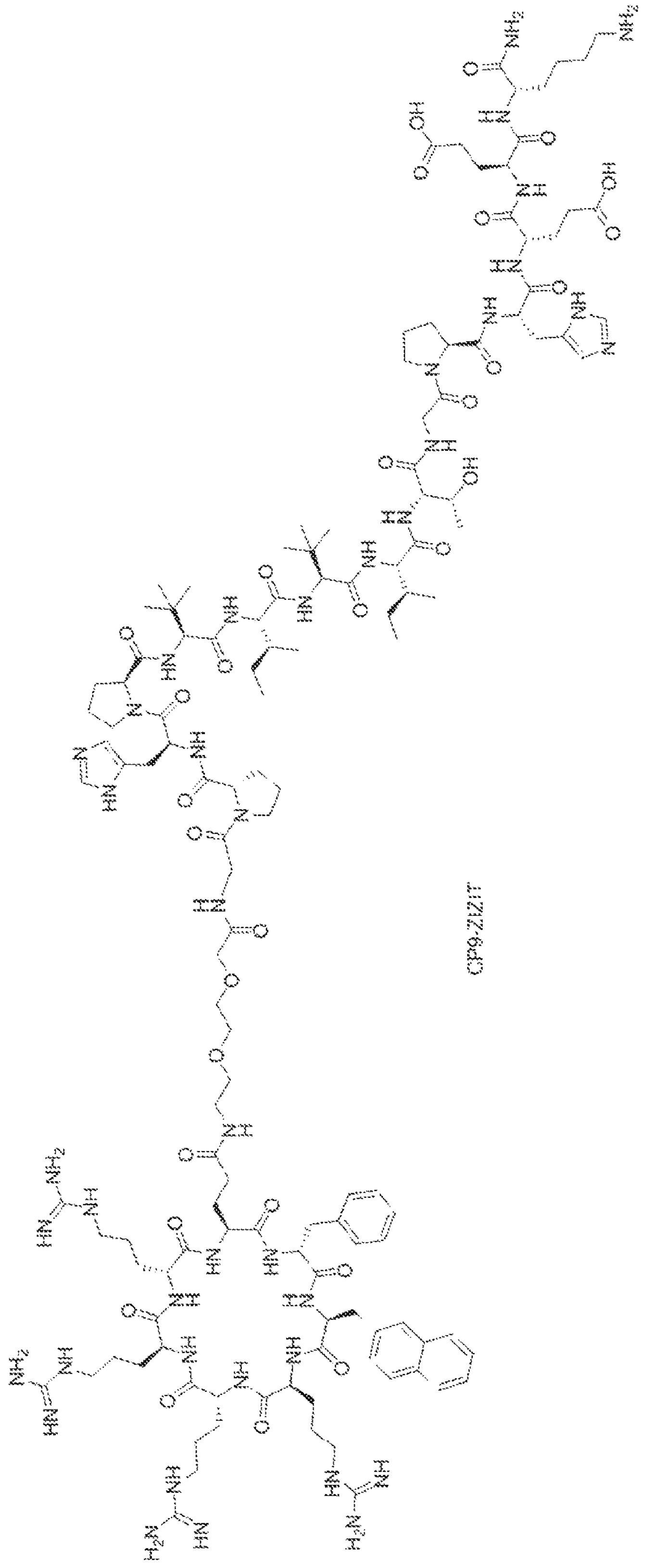
Figure 10B:
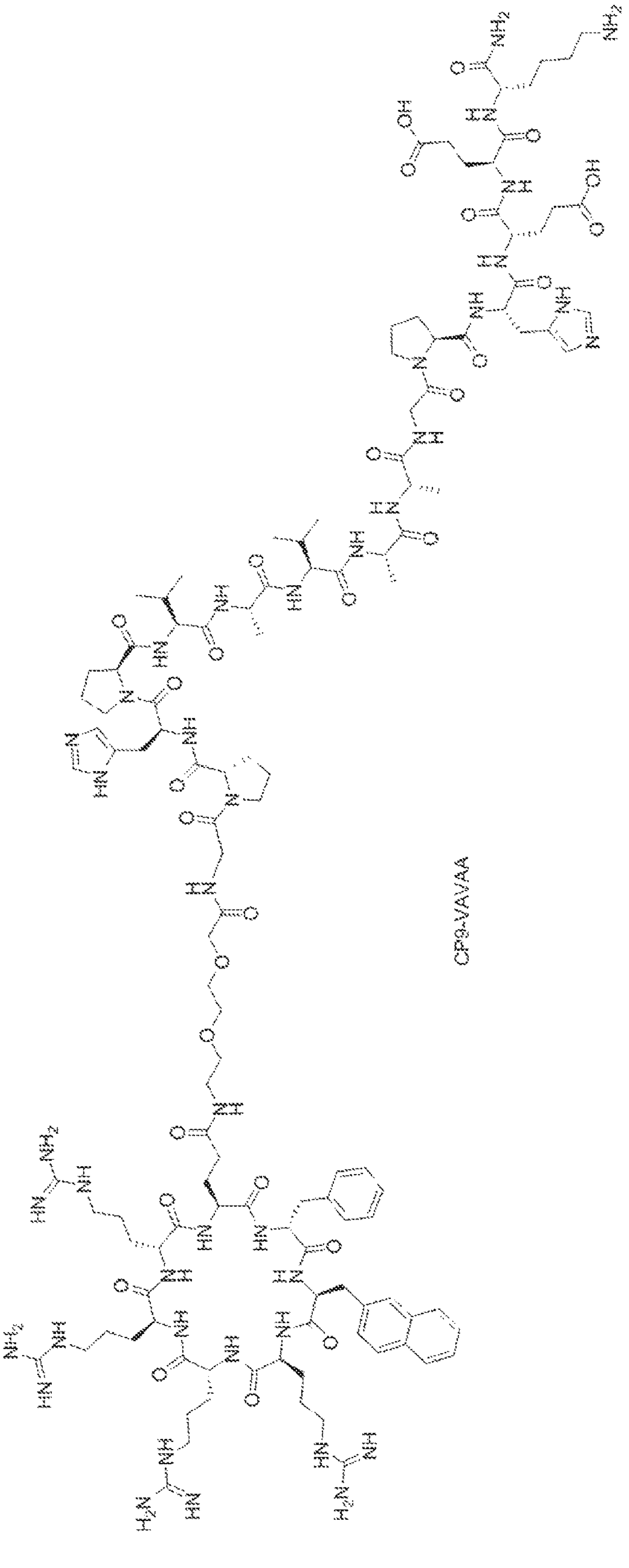
Figure 10C:
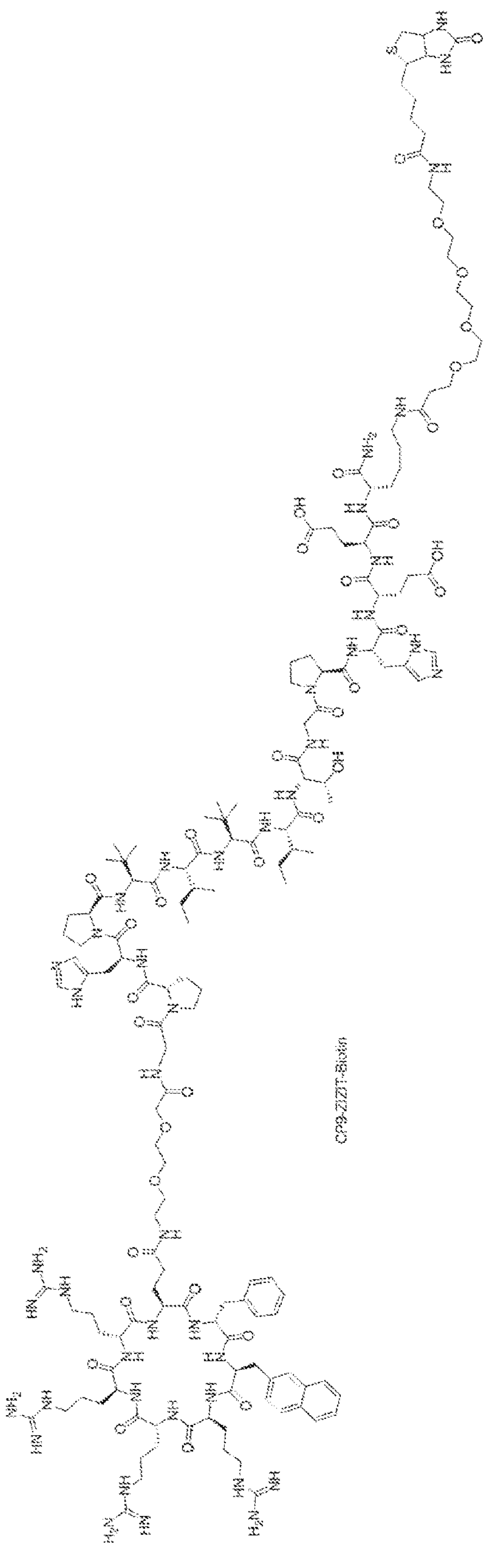
Figure 10D:
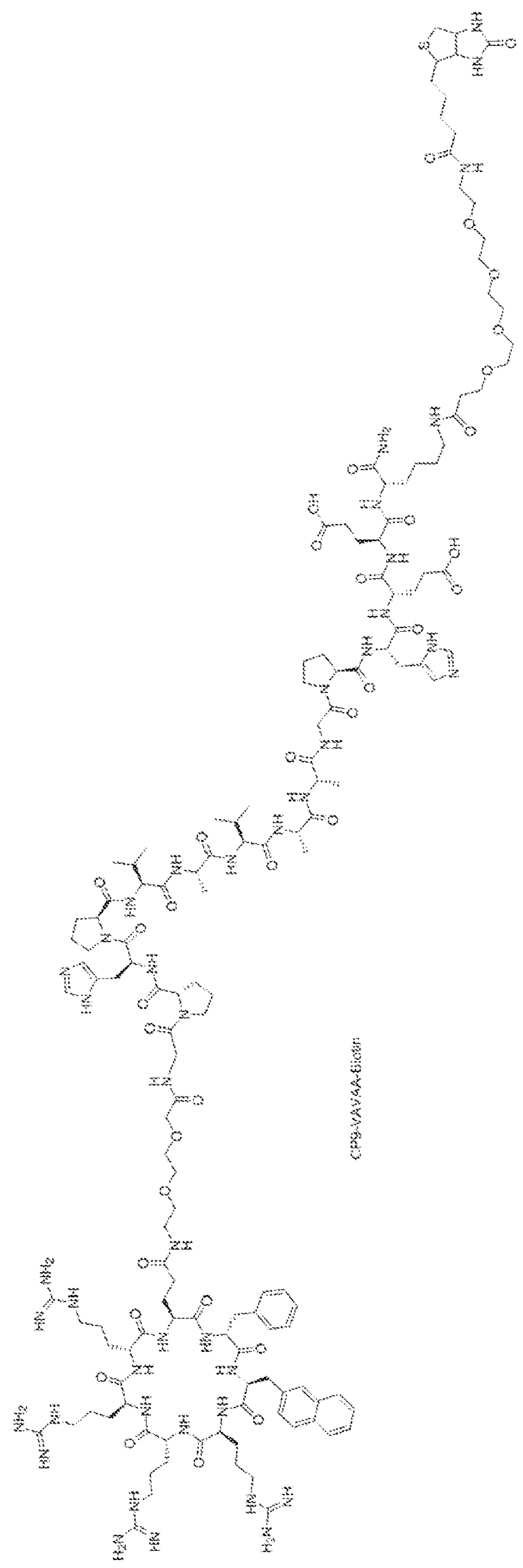
Figure 11A:
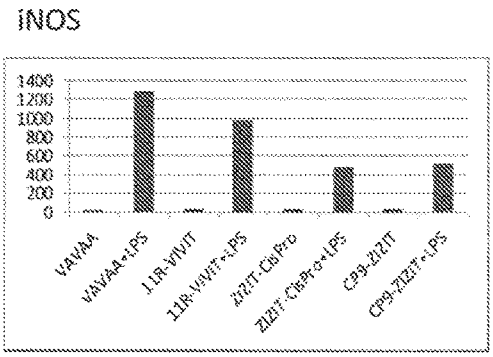
Figure 11B:
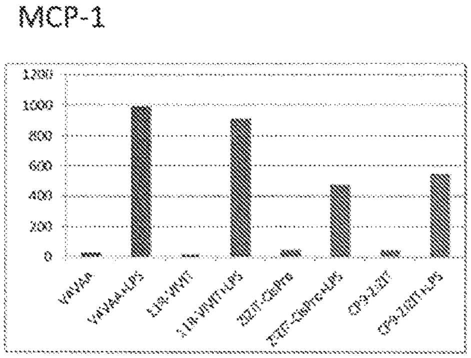
Figure 11C:
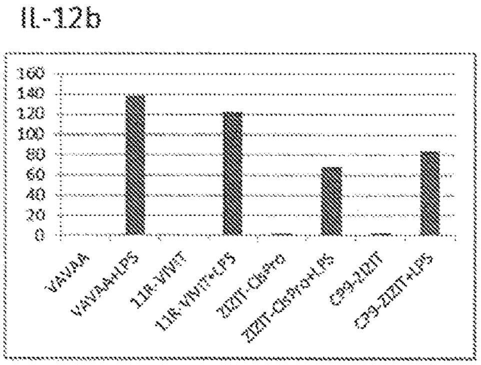
Figure 11D:
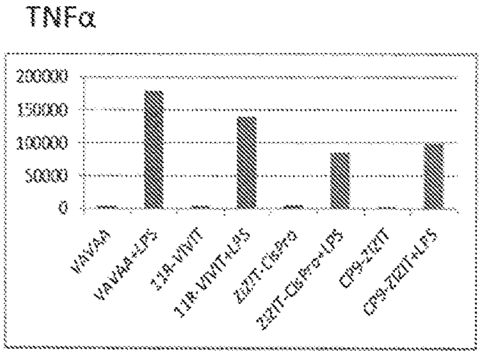

FIGS. 10A to 10D are chemical structures of the CP9-ZIZIT (FIG. 10A). CP9-VAVAA (FIG. 10B), CP9-ZIZIT-Biotin (FIG. 10C), and CP9-VAVAA-Biotin (FIG. 10D) compounds.

FIGS. 11A to 11D are bar graphs showing iNOS (FIG. 11A), MCP-1 (FIG. 11B), IL-12b (FIG. 11C), and TNFα (FIG. 11D) levels after treatment of macrophage cells with Calcineurin inhibitors, with and without LPS stimulation. R11-VIVIT was used at 50 μM, whereas $R_{11}$-ZIZIT-cisPro and CP9-ZIZIT were used at 1 μM (final concentration).

Figure 12:
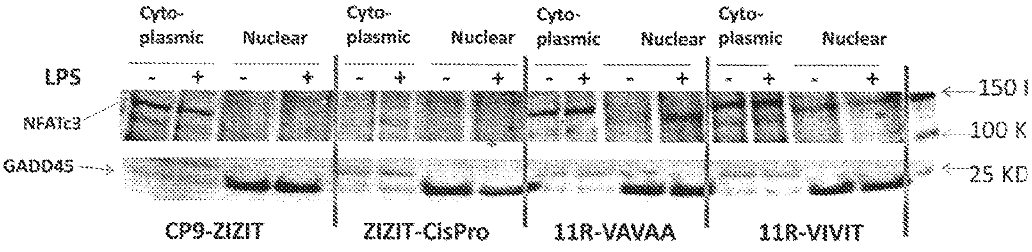

FIG. 12 shows nuclear translocation of NFATc3 is inhibited by CP9-ZIZIT and $R_{11}$-VIVIT.

Figure 13A:
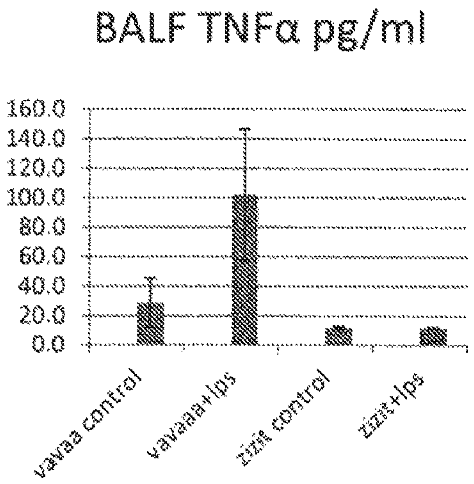
Figure 13B:
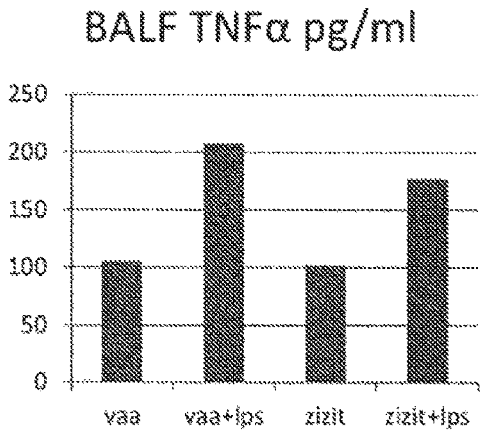
Figure 13C:
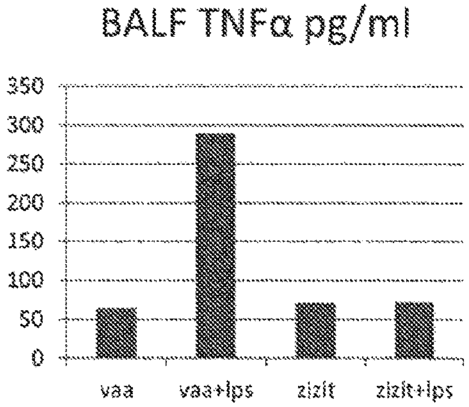
Figure 13D:
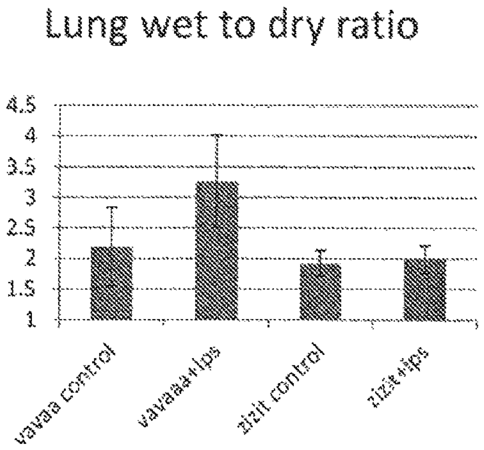
Figure 13E:
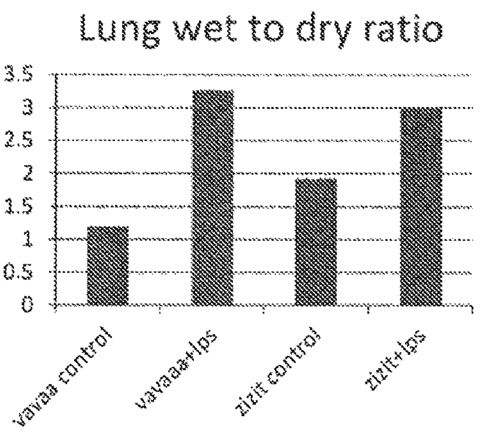

FIGS. 13A to 13E are bar graphs showing BALF TNFα (pg/ml) (FIGS. 13A to 13C) and lung wet to dry ratio (FIGS. 13D and 13E) 1 hour pre-challenge intranasal (FIGS. 13A and 13D), 1 hr post-challenge intranasal (FIGS. 13B and 13E), and 1 hr pre-challenge, 16 hr LPS intra peritoneal (FIG. 13C).

Figure 14A:
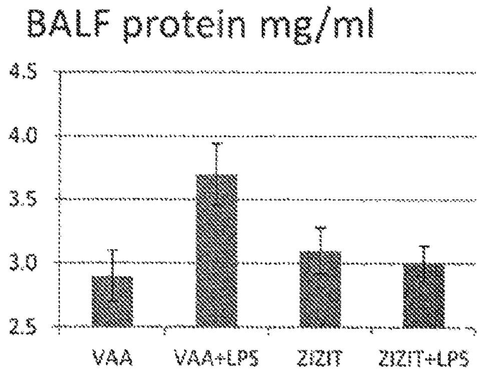
Figure 14B:
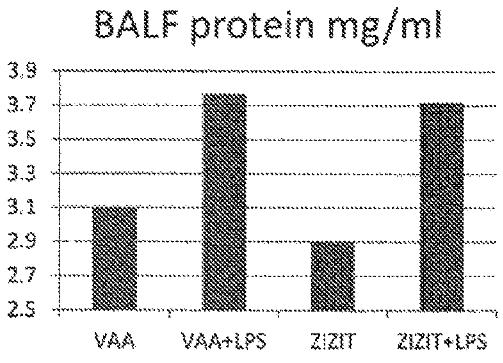
Figure 14C:
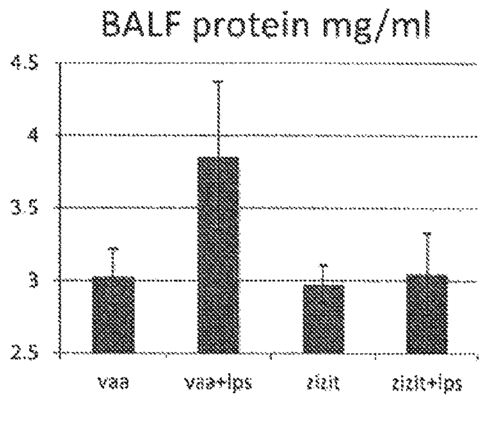
Figure 14D:
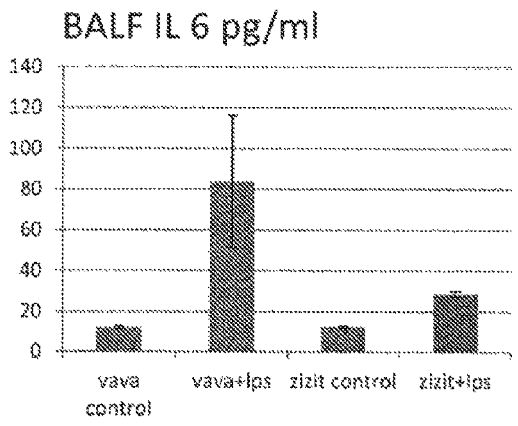
Figure 14E:
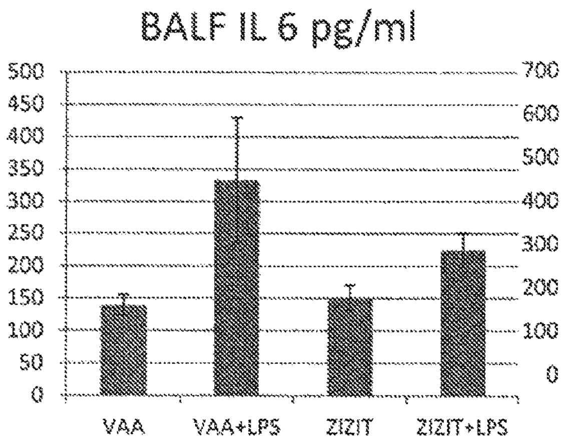
Figure 14F:
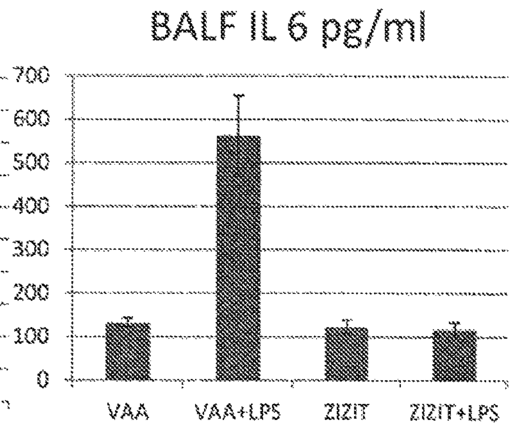

FIGS. 14A to 14F are bar graphs showing BALF protein (mg/ml) (FIGS. 14A to 14C) and BALF IL6 (pg/ml) (FIGS. 14D to 14F) 1 hour pre-challenge intranasal (FIGS. 14A and 14D), 1 hr post-challenge intranasal (FIGS. 14B and 14E), and 1 hr pre-challenge, 16 hr LPS intra peritoneal (FIGS. 14C and 14F).

DETAILED DESCRIPTION

The materials, compounds, compositions, articles, and methods described herein may be understood more readily by reference to the following detailed description of specific aspects of the disclosed subject matter and the Examples and Figures included therein.

Before the present materials, compounds, compositions, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

The term "inhibit" refers to a decrease in an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder, preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "prevent" refers to a treatment that forestalls or slows the onset of a disease or condition or reduced the severity of the disease or condition. Thus, if a treatment can treat a disease in a subject having symptoms of the disease, it can also prevent that disease in a subject who has yet to suffer some or all of the symptoms.

The terms "peptide," "protein," and "polypeptide" are used interchangeably to refer to a natural or synthetic molecule comprising two or more amino acids linked by the carboxyl group of one amino acid to the alpha amino group of another. In addition, the term "polypeptide" refers to amino acids joined to each other by peptide bonds or modified peptide bonds, e.g., peptide isosteres, etc. and may contain modified amino acids other than the 20 gene-encoded amino acids. The polypeptides can be modified by either natural processes, such as post-translational processing, or by chemical modification techniques which are well known in the art. Modifications can occur anywhere in the polypeptide, including the peptide backbone, the amino acid side-chains and the amino or carboxyl termini. The same type of modification can be present in the same or varying degrees at several sites in a given polypeptide. Also, a given polypeptide can have many types of modifications. Modifications include, without limitation, acetylation, acylation, ADP-ribosylation, amidation, covalent cross-linking or cyclization, covalent attachment of flavin, covalent attachment of a heme moiety, covalent attachment of a nucleotide or nucleotide derivative, covalent attachment of a lipid or lipid derivative, covalent attachment of a phosphytidylinositol, disulfide bond formation, demethylation, formation of cysteine or pyroglutamate, formylation, gamma-carboxylation, glycosylation. GPI anchor formation, hydroxylation, iodination, methylation, myristolyation, oxidation, pergylation, proteolytic processing, phosphorylation, prenylation, racemization, selenoylation, sulfation, and transfer-RNA mediated addition of amino acids to protein such as arginylation. (See Proteins—Structure and Molecular Properties 2nd Ed., T. E. Creighton, W.H. Freeman and Company, New York (1993); Posttranslational Covalent Modification of Proteins, B. C. Johnson, Ed., Academic Press, New York, pp. 1-12 (1983)).

As used herein. "peptidomimetic" refers to a mimetic of a peptide which includes some alteration of the normal peptide chemistry. Peptidomimetics typically enhance some property of the original peptide, such as increase stability, increased efficacy, enhanced delivery, increased half life, etc. Methods of making peptidomimetics based upon a known polypeptide sequence is described, for example, in U.S. Pat. Nos. 5,631,280; 5,612,895; and 5,579,250. Use of peptidomimetics can involve the incorporation of a non-amino acid residue with non-amide linkages at a given position. Some non-limiting examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, N-ε-Boc-N-α-CBZ-L-lysine, N-ε-Boc-N-α-Fmoc-L-lysine, L-methionine sulfone, L-norleucine, L-norvaline, N-α-Boc -N-δCBZ-L-ornithine, N-δ-Boc-N-α-CBZ-L-omithine, Boc-p-nitro-L-phenylalanine, Boc -hydroxyproline, and Boc-L-thioproline.

A "liposome" is a small vesicle composed of various types of lipids, phospholipids and/or surfactant which is useful for delivery of a drug (such as the antagonists disclosed herein and, optionally, a chemotherapeutic agent) to a mammal. The components of the liposome are commonly arranged in a bilayer formation, similar to the lipid arrangement of biological membranes.

Reference will now be made in detail to specific aspects of the disclosed materials, compounds, compositions, articles, and methods, examples of which are illustrated in the accompanying Examples and Figures.

Calcineurin Inhibitor

A calcineurin (CN) inhibitor that specifically modulates the CN-NFAT signaling pathway is disclosed. Previous structural and functional analysis of the CN-NFAT interface has identified a conserved sequence motif among NFAT proteins, PxIxIT (where x is any amino acid; SEQ ID NO:5), which specifically interacts with a substrate-docking site on CN (Aramburu, J., et al. Mol. Cell 1998 1:627-637). This interaction is critical for dephosphorylation of NFAT and a subset of other CN substrates (Li, H., et al. Trends Cell Biol. 2011 21:91-103; Roy, J., et al. Sci. Signal. 2009 2:re9; Grigoriu, S., et al. PLoS Biol. 2013 11:e1001492). Screening of an oriented peptide library identified a tetradecapeptide, GPHPVIVITGPHEE ("VIVIT", SEQ ID NO:47), which binds to the docking site on CN with 25-fold higher affinity than the naturally occurring "PxIxIT" motif (Aramburu, J., et al. Science 1999 285:2129-2133). Expression of peptide VIVIT in mammalian cells effectively blocks the CN-NFAT interaction and its downstream signaling without directly blocking CN enzymatic activity. Attachment to a cell-penetrating peptide renders the peptide cell permeable and active for immunosuppression in transplanted mice (Noguchi, H., et al. Nat. Med. 2004 10:305-309).

However, the reported VIVIT compounds have somewhat low potency in disrupting the CN-NFAT interaction. In this work, structural information derived from NMR and X-ray studies was used as a guide for structure-based optimization of the VIVIT peptide. This led to the disclosed peptides, some of which have approximately 200-fold improvement in the binding affinity and highly potent and selective inhibition against CN.

In some embodiments, the disclosed calcineurin (CN) inhibitor is a peptide or peptidomimetic ("ZIZIT") comprising the amino acid sequence:

```
ZIZITXII,         (SEQ ID NO: 1)
PZIZITXII,        (SEQ ID NO: 33)
ZIZITXIIH,        (SEQ ID NO: 34)
PZIZITXIIH,       (SEQ ID NO: 35)
ZIZITXIIHE,       (SEQ ID NO: 36)
PZIZITXIIHE,      (SEQ ID NO: 37)
ZIZITXIIHEE,      (SEQ ID NO: 38)
or
PZIZITXIIHEE,     (SEQ ID NO: 39)
```

wherein

X comprises any amino acid,

Z comprises tert-leucine, L-penicillamine, or an S-alkylated derivative of L-penicillamine, and Π comprises proline or a proline analogue.

As discussed above, Z can comprise tert-leucine, L-penicillamine, or an S-alkylated derivative of L-penicillamine. S-alkylated derivatives of L-penicillamine include penicillamine residues where the sulfhydryl group has been alkylated to afford a thioether. In some embodiments, the S-alkylated derivative of L-penicillamine can include a $C_1$-$C_{12}$ alkylated (e.g., a $C_1$-$C_8$ alkylated, a $C_1$-$C_6$ alkylated, or a $C_1$-$C_4$ alkylated) derivative of L-penicillamine, where the number of carbons refers to the number of carbon atoms present in the thioether moiety.

In some embodiments, X is Gly or an analog or conservative variant thereof.

In some embodiments, the substitution of Val in VIVIT with Z (e.g., Tle) improves the potency and bioavailability of the peptidomimetic compared to the VIVIT peptide. First, the $Val^5$ and $Val^7$ side chains of the VIVIT peptide are distant from the hydrophobic surface formed by the side chain of CN $Val^{328}$ for optimal van der Waals interaction. Replacement of the valines with bulkier Z (e.g., Tle) results in closer packing and improved van der Waals interactions between the side chains of Z/Z in the peptidomimetic and CN $Val^{328}$. Second, Z (e.g., Tle) can substantially improve the target-binding affinity, protease resistance, and bioavailability.

Figure 1A:
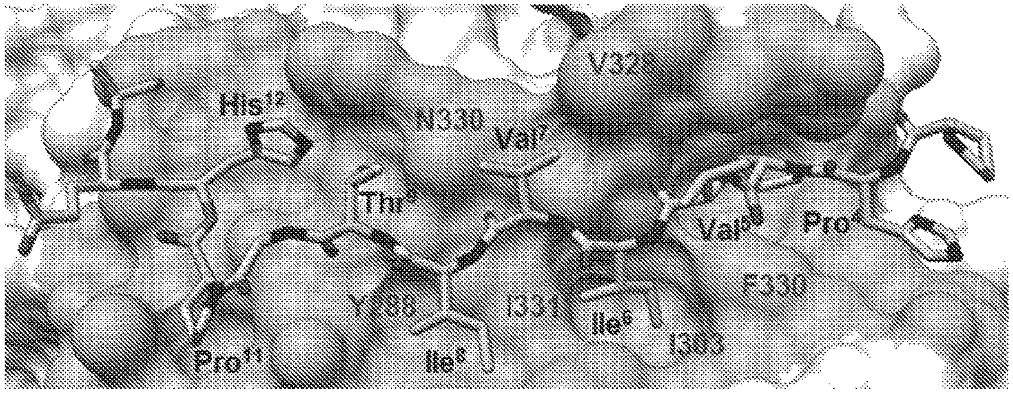
FIG. 1A shows an x-ray crystal structure of the CN-VIVIT complex.

The structure of the CN-VIVIT complex contains a cis peptide bond between $Gly^{10}$ and $Pro^{11}$ of the VIVIT peptide (FIG. 1A). The β-turn structure permits the formation of an intricate hydrogen bond network among the side chains of $Asn^{330}$ (of CN) and $His^{12}$ and $Thr^{8}$ of the VIVIT peptide. Since the trans-configuration of a peptidyl-prolyl peptide bond is energetically more stable, the disclosed peptidomimetic can be modified to preorganization the peptide bond between the X and Π residues into the cis-configuration. This can increase the binding affinity of the peptidomimetic for CN. For example, in some cases, the Π residue comprises 2,2-dimethylthiazolidine-4-carboxylic acid [Cys ($\Psi^{Me,Me}$Pro)], which is a proline analog that sterically locks the preceding peptide bond into the cis-configuration when incorporated into a peptide (Dumy, P., et al. J. Am. Chem. Soc. 1997 119:918-925; Chierici, S., et al. Org. Biomol. Chem. 2004 2:2436-2441). Other similar proline analogs are known in the art. For example, in some cases, the Π residue comprises 5,5-dimethyl-L-proline. In some cases, the Π residue comprises 2,2-dimethylthiazolidine-4-carboxylic acid.

In some embodiments, the disclosed calcineurin (CN) inhibitor is a peptide or peptidomimetic comprising the amino acid sequence:

| | |
|---|---|
| PZIZITXII, | (SEQ ID NO: 40) |
| ZIZITXIIH, | (SEQ ID NO: 41) |
| PZIZITXIIH, | (SEQ ID NO: 42) |
| ZIZITXIIHE, | (SEQ ID NO: 43) |
| PZIZITXIIHE, | (SEQ ID NO: 44) |
| ZIZITXIIHEE, | (SEQ ID NO: 45) |
| PZIZITXIIHEE, | (SEQ ID NO: 46) |

wherein

X comprises any amino acid,

Z comprises tert-leucine, L-penicillamine, or an S-alkylated derivative of L-penicillamine, and Π comprises dimethylthiazolidine-4-carboxylic acid.

In some embodiments, the CN inhibitor comprises the amino acid sequence GPHPZIZITGPHEE (SEQ ID NO:3), wherein Z comprises tert-leucine. In some embodiments, the CN inhibitor comprises the amino acid sequence GPHPZIZITGHHEE (SEQ ID NO:4), wherein Z comprises tert-leucine, and wherein Π=dimethylthiazolidine-4-carboxylic acid.

In some embodiments, the peptide or peptidomimetic CN inhibitor is 7 to 200 amino acids in length, including 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 61, 62, 64, 65, 66, 67, 68, 69, 70, 71, 72, 73, 74, 75, 76, 77, 78, 79, 80, 81, 82, 83, 84, 85, 86, 87, 88, 89, 90, 100, 110, 120, 130, 140, 150, 160, 170, 180, 190, or 200, amino acids in length. In some embodiments, the peptide or peptidomimetic CN inhibitor is linked or conjugated to a second polypeptide or protein of any size, but is conformational distinct from the second polypeptide or protein. For example, in some cases, the CN inhibitor is a domain of a fusion protein. In these embodiments, the size of the CN inhibitor corresponds to the size of the domain, not the entire protein.

Cell Penetrating Moieties

The disclosed CN inhibitor can be linked to a cell penetrating moiety capable of delivering the ZIZIT peptide or peptidomimetic into the cytosol of a cell. Non-limiting examples of cell penetrating moieties include Polyarginine (e.g., $R_9$ or $R_{11}$), Antennapedia sequences, HIV-TAT, Penetratin, Antp-3A (Antp mutant), Buforin II. Transportan, MAP (model amphipathic peptide), K-FGF, Ku70, Prion, pVEC, Pep-1, SynB1, Pep-7, HN-1, BGSC (Bis-Guanidinium-Spermidine-Cholesterol, and BGTC (Bis-Guanidinium-Tren-Cholesterol)

In some examples, the cell penetrating moiety is a cyclic peptide. For example, in some embodiments, the CN inhibitor comprises the cell penetrating peptide shown in Formula I:

I

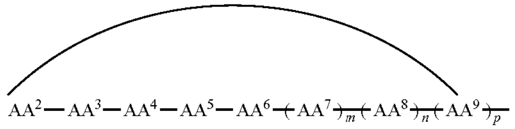

wherein $AA^1$, $AA^2$, $AA^3$, $AA^4$, $AA^5$, $AA^6$, $AA^7$, $AA^8$, and $AA^9$ (i.e., $AA^1$-$AA^9$) are each independently an amino acid; and m, n and p are independently selected from 0 and 1, with the proviso that if m is 0, n and p are not 1, and with the proviso that if n is 0, p is not 1, and wherein the curved line indicates a covalent bond. The cell penetrating peptide moiety comprises at least 6 amino acids, more specifically from 6 to 9, from 6 to 7, from 7 to 8, from 8 to 9, and more specifically 6, 7, 8 or 9 amino acids.

In some examples, at least one amino acid of the cell penetrating peptide comprises napthylalanine or an analogue or derivative thereof. In some examples, at least three of the amino acids independently comprise arginine or an analogue or derivative thereof. In some examples, at least one amino acid comprises phenylalanine or an analogue or derivative thereof. In some examples of, at least one amino acid comprises glutamine or an analogue or derivative thereof.

In some examples, the cell penetrating peptide (CPP) moiety can be a linear or cyclic form of any of the sequences listed in Table 1.

TABLE 1

CPP sequences - linear or cyclic

| CPP sequence | SEQ ID NO | #AA | #R |
|---|---|---|---|
| FΦRRRQ | 8 | 6 | 3 |
| FΦRRRC | 9 | 6 | 3 |
| FΦRRRU | 10 | 6 | 3 |
| RRRΦFQ | 11 | 6 | 3 |
| RRRRΦF | 12 | 6 | 4 |
| FΦRRRR | 13 | 6 | 4 |
| FϕrRrRq | 14 | 7 | 3 |
| FϕrRrRQ | 15 | 7 | 3 |
| FΦRRRRQ | 16 | 7 | 4 |
| fΦRrRrQ | 17 | 7 | 4 |
| RRFRΦRQ | 18 | 7 | 4 |
| FRRRRΦQ | 19 | 7 | 4 |

TABLE 1-continued

| CPP sequences - linear or cyclic | | | |
|---|---|---|---|
| CPP sequence | SEQ ID NO | #AA | #R |
| rRFRΦRQ | 20 | 7 | 4 |
| RRΦFRRQ | 21 | 7 | 4 |
| CRRRRFWQ | 22 | 7 | 4 |
| FfΦRrRrQ | 23 | 8 | 4 |
| FFΦRRRRQ | 24 | 8 | 4 |
| RFRFRΦRQ | 25 | 8 | 4 |
| URRRRFWQ | 26 | 8 | 4 |
| CRRRRFWQ | 27 | 8 | 4 |
| FΦRRRRQK | 28 | 8 | 4 |
| FΦRRRRQC | 29 | 8 | 4 |
| fΦRrRrRQ | 30 | 8 | 5 |
| FΦRRRRRQ | 31 | 8 | 5 |
| RRRRΦFDΩC | 32 | 9 | 4 |

f = D-phenylalanine,
Φ = L-naphthylalanine;
ϕ = D-naphthylalanine;
Ω = L-norleucine In some examples, the cell penetrating peptide moeity can by any of SEQ ID NO:8 to SEQ ID NO:32. In some examples, the cell penetrating peptide moiety can be a variant of any of SEQ ID NO:8 to SEQ ID NO:32.

The cell penetrating moiety can be attached to the ZIZIT peptide at the amino group, the carboxylate group, or the side chain of any of the amino acids of the ZIZIT peptide. The ZIZIT peptide can be attached to the cell penetrating peptide moiety at the amino group, the carboxylate group, or the side chain (e.g., Gin side chain) of any of the amino acids of the cell penetrating peptide moiety (e.g., at the amino group, the carboxylate group, or the side chain or any of $AA^1$-$AA^9$).

The cell penetrating moiety can be linked to the CN inhibitor peptidomimetic by a linker. In some cases, the linker is a peptide or peptide bond. In some cases, the linker comprises polyethyleneglycol.

Peptide Variants

Peptide variants are well understood to those of skill in the art and can involve amino acid sequence modifications. For example, amino acid sequence modifications typically fall into one or more of three classes: substitutional, insertional, or deletional variants. Insertions include amino and/or carboxyl terminal fusions as well as intrasequence insertions of single or multiple amino acid residues. Insertions ordinarily will be smaller insertions than those of amino or carboxyl terminal fusions, for example, on the order of 1 to 3 residues. Deletions are characterized by the removal of one or more amino acid residues from the peptide sequence. Typically, no more than from 1 to 3 residues are deleted at any one site within the peptide. Amino acid substitutions are typically of single residues, but can occur at a number of different locations at once; insertions usually will be on the order of about from 1 to 3 amino acid residues; and deletions will range about from 1 to 3 residues. Deletions or insertions preferably are made in adjacent pairs, i.e. a deletion of 2 residues or insertion of 2 residues. Substitutions, deletions, insertions or any combination thereof can be combined to arrive at a final construct. Substitutional variants are those in which at least one residue has been removed and a different residue inserted in its place. Such substitutions generally are made in accordance with the following Table 2 and are referred to as conservative substitutions.

TABLE 2

| Exemplary Amino Acid Substitutions |
|---|
| Ala replaced by ser |
| Arg replaced by lys or gln |
| Asn replaced by gln or his |
| Asp replaced by glu |
| Cys replaced by ser |
| Gln replaced by asn or lys |
| Glu replaced by asp |
| Gly replaced by pro |
| His replaced by asn or gln |
| Ile replaced by leu or val |
| Leu replaced by ile or val |
| Lys replaced by arg or gln |
| Met replaced by leu or ile |
| Phe replaced by met or leu; tyr |
| Ser replaced by thr |
| Thr replaced by ser |
| Trp replaced by tyr |
| Tyr replaced by trp or phe |
| Val replaced by ile or leu |

Substantial changes in function are made by selecting substitutions that are less conservative than those in Table 2, i.e., selecting residues that differ more significantly in their effect on maintaining (a) the structure of the peptide backbone in the area of the substitution, for example as a sheet or helical conformation, (b) the charge or hydrophobicity of the molecule at the target site or (c) the bulk of the side chain. The substitutions which in general are expected to produce the greatest changes in the protein properties will be those in which (a) a hydrophilic residue, e.g., seryl or threonyl, is substituted for (or by) a hydrophobic residue, e.g., leucyl, isoleucyl, phenylalanyl, valyl or alanyl; (b) a cysteine or proline is substituted for (or by) any other residue; (c) a residue having an electropositive side chain, e.g., lysyl, arginyl, or histidyl, is substituted for (or by) an electronegative residue, e.g., glutamyl or aspartyl; or (d) a residue having a bulky side chain, e.g., phenylalanine, is substituted for (or by) one not having a side chain, e.g., glycine, in this case, (e) by increasing the number of sites for sulfation and/or glycosylation.

For example, the replacement of one amino acid residue with another that is biologically and/or chemically similar is known to those skilled in the art as a conservative substitution. In some embodiments, a conservative amino acid substitution includes one in which the amino acid residue is replaced with an amino acid residue having a similar side chain. For example, families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Other conserved amino acid substitutions can also occur across amino acid side chain families, such as when substituting an asparagine for aspartic acid in order to modify the charge of a peptide. In some embodiments, conservative substitutions include combinations such as, for example, Gly, Ala; Val, Ile, Leu; Asp, Glu; Asn, Gln; Ser, Thr; Lys, Arg; and Phe, Tyr. Such conservatively substituted variations of each explicitly disclosed sequence are included within the peptides provided herein.

It is understood that one way to define the variants of the disclosed cell penetrating peptide moieties is through defining the variants in terms of homology/identity to specific known sequences. For example, SEQ ID NO: 1 to SEQ ID NO:32 each sets forth a particular sequence. Specifically disclosed are variants of these peptide that have at least, 85%, 90%, 95%, or 97% homology to SEQ ID NO:1 to SEQ ID NO:32. Those of skill in the art readily understand how to determine the homology of two proteins. For example, the homology can be calculated after aligning the two sequences so that the homology is at its highest level.

In addition to variants of SEQ ID NO: 1 to SEQ ID NO:32 are derivatives of these peptides which also function in the disclosed methods and compositions. Derivatives are formed by replacing one or more residues with a modified residue, where the side chain of the residue has been modified.

In some embodiments, one ore more amino acids of the disclosed CN inhibitor is a non-natural amino acid. The term "non-natural amino acid" refers to an organic compound that is a congener of a natural amino acid in that it has a structure similar to a natural amino acid so that it mimics the structure and reactivity of a natural amino acid. The non-natural amino acid can be a modified amino acid, and/or amino acid analog, that is not one of the 20 common naturally occurring amino acids or the rare natural amino acids selenocysteine or pyrrolysine.

The disclosed CN inhibitors are capable of inhibiting the calcineurin-NFAT signaling pathway. In some embodiments, the CN inhibitors are capable of inhibiting dephosphorylation of NFAT by calcineurin. In certain embodiments, the disclosed CN inhibitors are capable of inhibiting recruitment of NFAT to the nucleus in a cell. In certain embodiments, the disclosed CN inhibitors are capable of inhibiting conformational change in NFAT that results from the protein-protein interaction between NFAT and calcineurin or from the dephosphorylation of NFAT by calcineurin. In certain embodiments, the disclosed CN inhibitors are capable of inhibiting NFAT-dependent gene transcription.

In preferred embodiments, the disclosed CN inhibitors do not substantially inhibit the activity of calcineurin toward non-NFAT calcineurin substrates. Calcineurin normally is capable of interacting with many different substrates, e.g., NFAT and the microtubule-associated protein tau (Fleming and Johnson, Biochem J 309:41-47 (1995); Yamamoto et al, J Biochem 118:1224-1231 (1995)), the regulatory subunit RII of cAMP-dependent protein kinase (Blumenthal and Krebs, Biophys J 41:409a (1983)), inhibitor-1 (Hemmings et al, Nature 310:503-505 (1984); Mulkey et al, Nature 369: 486-488 (1994)), dopamine- and cAMP-regulated phosphoprotein DARPP-32 (Hemmings et al, Nature 310:503-505 (1984)), a dihydropyridine-sensitive voltage-dependent Ca2+ channel (Hosey et al, Proc Natl Acad Sci USA 83:3733-3737 (1986)), nitric oxide synthase (Dawson et al, Proc Natl Acad Sci USA 90:9808-9812 (1993)), dynamin (Liu et al, Science 265:970-973 (1994); Nichols et al, J Biol Chem 269:23817-23823 (1994)), the inositol 1,4,5-trisphosphate receptor-FKBP12 complex (Cameron et al, Cell 83:463-472 (1995)), and the ryanodine receptor-FKBP12 complex (Cameron et al, Cell 83:463-472 (1995)). A key advantage of the disclosed CN inhibitors is that they are specific for the interaction between calcineurin and NFAT. Such specific inhibitors can be used for therapeutic purposes with reduced toxic effects, as compared to general immuno suppressants.

Peptide and peptidomimetic variants capable of inhibiting the calcineurin-NFAT signaling pathway can be identified by any method known in the art for measuring calcineurin-induced activation of NFAT using a stimulant, e.g., calcium ionophore, a neurotransmitter, or a biologically active peptide, known to trigger activation of NFAT via the calcium/calcineurin pathway. Such methods include, without limitation, determination of the expression levels of a reporter gene operatively linked to N FAT operator sequences in cells after induction of calcineurin activity by stimulation with ionomycin, PMA and $CaCl_2$, methods based in the determination of the ability of the peptide to prevent translocation of NFAT to the nucleus in cells expressing the peptide after induction of calcineurin activity by stimulation with ionomycin, PMA and $CaCl_2$ (Aubareda et al. Cellular Signaling, 2006, 18: 1430-1438), methods based on the determination of NFAT-dependent cytokines in T cells, including one or more of GM-CSF, IFNy, TNFa, IL-2, IL-3 and IL-13 after stimulation of the cells using ionomycin and PMA (Aubareda et al. Cellular Signaling, 2006, 18: 1430-1438), and methods based on the determination of the ability of the peptide to prevent calcineurin-induced NFAT dephosphorylation (Martinez et al. Proc. Natl. Acad. Sci. USA, 2009, 106: 6117-6122). Peptide and peptidomimetic variants for use as CN inhibitors include those capable of achieving at least 5%, at least 10%, at least 20%, at least 30%, at least 40%, at least 50%, at least 60%, at least 70%, at least 80%, at least 90% or 100% of the calcineurin-NFAT signalling pathway.

The terminal amino group or carboxyl group of the CN inhibitor peptide or peptidomimetic may be modified by alkylation, amidation, or acylation to provide esters, amides or substituted amino groups, where the alkyl or acyl group may be of from about 1 to 30, usually 1 to 24, preferably either 1 to 3 or 8 to 24, particularly 12 to 18 carbon atoms. The peptide or peptidomimetic may also be modified by acetylation or methylation to alter the chemical properties, for example lipophilicity. Other modifications include deamination of glutamyl and asparaginyl residues to the corresponding glutamyl and aspartyl residues, respectively; hydroxylation of proline and lysine; phosphorylation of hydroxyl groups of serine or threonine; and methylation of amino groups of lysine, arginine, and histidine side chains (see T. E. Creighton, Proteins: Structure and Molecular Properties, W.H. Freeman & Co. San Francisco, Calif. 1983).

Depending upon their intended use, particularly for administration to mammalian hosts, the subject peptide or peptidomimetic may be modified or attached to other compounds for the purposes of incorporation into carrier molecules, changing peptide bioavailability, extend or shorten half-life, control distribution to various tissues or the blood stream, diminish or enhance binding to blood components, and the like. The subject peptide or peptidomimetic may be bound to these other components by linkers which are cleavable or non-cleavable in the physiological environment such as blood, cerebrospinal fluid, digestive fluids, etc. The peptides may be joined at any point of the peptide or peptidomimetic where a functional group is present, such as hydroxyl, thiol, carboxyl, amino, or the like. Desirably, modification will be at either the N-terminus or the C-terminus. For these purposes, the subject peptide or peptidomimetic may be modified by covalently attaching polymers, such as polyethylene glycol, polypropylene glycol, carboxymethyl cellulose, dextran, polyvinyl alcohol, polyvinylpyrrolidine, polyproline, poly(divinyl-ether-co-maleic anhydride), poly(styrene-c-maleic anhydride), etc. Water soluble polymers, such a polyethylene glycol and polyvinylpyrrolidine are known to decrease clearance of attached compounds from the blood stream as compared to unmodified compounds. The modifications can also increase solubility in aqueous media and reduce aggregation of the peptides.

Cell Delivery Vehicles

In some embodiments, the disclosed CN inhibitor does not contain a cell penetrating moeity and must be delivered to the cell cytosol by a separate vehicle. Therefore, in some embodiments, the disclosed CN inhibitor is conjugated to, or encapsulated in, a cell delivery vehicle.

Small molecules that target the conjugate to specific cells or tissues may also be used. It is known that presence of a biotin-avidin complex increases uptake of such modified peptides across endothelial cells. Linkage of peptides to carbohydrate moieties, for example to a β-glycoside through a serine residue on the peptide to form a β-0 linked glycoside, enhances transport of the glycoside derivative via glucose. Both of these types of modifications are encompassed within the scope of the disclosed compositions.

In some embodiments, cellular uptake is facilitated by the attachment of a lipid, such as stearate or myristilate, to the polypeptide. Lipidation has been shown to enhance the passage of peptides into cells.

Additionally, the peptide or peptidomimetic may also be introduced or encapsulated into the lumen of liposomes for delivery and for extending life time of the peptide or peptidomimetic formulations. As known in the art, liposomes can be categorized into various types: multilamellar (MLV), stable plurilamellar (SPLV), small unilamellar (SUV) or large unilamellar (LUV) vesicles. Liposomes can be prepared from various lipid compounds, which may be synthetic or naturally occurring, including phosphatidyl ethers and esters, such as phosphotidylserine, phosphotidylcholine, phosphatidyl ethanolamine, phosphatidylinositol, dimyristoylphosphatidylcholine; steroids such as cholesterol; cerebrosides; sphingomyelin; glycerolipids; and other lipids.

Cationic lipids are also suitable for forming liposomes. Generally, the cationic lipids have an net positive charge and have a lipophilic portion, such as a sterol or an acyl or diacyl side chain. Preferably, the head group is positively charged. Typical cationic lipids include 1,2-dioleyloxy-3-(trimethylamino)propane; N-[1-(2,3,-ditetradecycloxy)propyl]-N,N-dimethyl-N-N-hydroxyethylammonium bromide; N-[1-(2,3-dioleyloxy)propyl]-N,N-dimethyl-N-hydroxy ethylammonium bromide; N-[1-(2,3-dioleyloxy) propyl]-N,N,N-trimethylammonium chloride; 3-[N-(N'.N'-dimethylaminoethane) carbamoyl] cholesterol; and dimethyldioctadecylammonium.

Of particular interest are fusogenic liposomes, which are characterized by their ability to fuse with a cell membrane upon appropriate change in physiological condition or by presence of fusogenic component, particularly a fusogenic peptide or protein. In one aspect, the fusogenic liposomes are pH and temperature sensitive in that fusion with a cell membrane is affected by change in temperature and/or pH. Generally, pH sensitive liposomes are acid sensitive. Thus, fusion is enhanced in physiological environments where the pH is mildly acidic, for example the environment of a lysosome, endosome and inflammatory tissues. This property allows direct release of the liposome contents into the intracellular environment following endocytosis of liposomes.

Another form of fusogenic liposomes comprise liposomes that contain a fusion enhancing agent. That is, when incorporated into the liposome or attached to the lipids, the agents enhance fusion of the liposome with other cellular membranes, thus resulting in delivery of the liposome contents into the cell. The agents may be fusion enhancing peptides or proteins, including hemagglutinin HA2 of influenza virus; Sendai virus envelope glycoproteins; vesicular stomatitis virus envelope glycoproteins (VSV-G) glycoprotein; peptide segments or mimics of fusion enhancing proteins; and synthetic fusion enhancing peptides.

Liposomes also include vesicles derivatized with a hydrophilic polymer to extend the circulation lifetime in vivo. Hydrophilic polymers for coating or derivation of the liposomes include polyethylene glycol, polyvinylpyrrolidone, polyvinylmethyl ether, polyaspartamide, hydroxymethyl cellulose, hydroxyethyl cellulose, and the like. In addition, as described above, attaching proteins that bind a cell surface protein which is endocytosed, e.g., capsid proteins or fragments thereof tropic for a particular cell types and antibodies for cell surface proteins which undergo internalization may be used for targeting and/or facilitating uptake of the liposomes to specific cells or tissues.

Liposomes are prepared by ways well known in the art. One typical method is the lipid film hydration technique in which lipid components are mixed in an organic solvent followed by evaporation of the solvent to generate a lipid film. Hydration of the film in aqueous buffer solution, preferably containing the subject peptide or peptidomimetic, results in an emulsion, which is sonicated or extruded to reduce the size and polydispersity. Other methods include reverse-phase evaporation, freezing and thawing of phospholipid mixtures, and ether infusion.

In some embodiments, the carriers are in the form of microparticles, microcapsules, microspheres and nanoparticles, which may be biodegradable or non-biodegradable. As used herein, microparticles, microspheres, microcapsules and nanoparticles mean a particle, which is typically a solid, containing the substance to be delivered. The substance is within the core of the particle or attached to the particle's polymer network. Generally, the difference between microparticles (or microcapsules or microspheres) and nanoparticles is one of size. As used herein, microparticles have a particle size range of about 1 to about >1000 microns. Nanoparticles have a particle size range of about 10 to about 1000 nm.

A variety of materials are useful for making microparticles. Non-biodegradable microcapsules and microparticles include, but not limited to, those made of polysulfones, poly(acrylonitrile-co-vinyl chloride), ethylene-vinyl acetate, hydroxyethylmethacrylate-methyl-methacrylate copolymers. These are useful for implantation purposes where the encapsulated peptide diffuses out from the capsules. In another aspect, the microcapsules and microparticles are based on biodegradable polymers, preferably those that display low toxicity and are well tolerated by the immune system. These include protein based microcapsulates and microparticles made from fibrin, casein, serum albumin, collagen, gelatin, lecithin, chitosan, alginate or poly-amino acids such as poly-lysine. Biodegradable synthetic polymers for encapsulating may comprise polymers such as polylactide (PLA), polyglycolide (PGA), poly(lactide-co-glycolide) (PLGA), poly(caprolactone), polydioxanone trimethylene carbonate, polyhybroxyalkonates (e.g., poly(β-hydroxybutyrate)), poly(γ-ethyl glutamate), poly(DTH iminocarbony (bisphenol A iminocarbonate), poly (ortho ester), and polycyanoacrylate. Various methods for making microparticles containing the subject compositions are well known in the art, including solvent removal process (see for example, U.S. Pat. No. 4,389,330); emulsification and evaporation (Maysinger, D. et al. Exp. Neuro. 141: 47-56 (1996); Jeffrey. H. et al. Pharm. Res. 10: 362-68 (1993)), spray drying, and extrusion methods.

Another type of carrier is nanoparticles, which are generally suitable for intravenous administrations. Submicron and nanoparticles are generally made from amphiphilic diblock, triblock, or multiblock copolymers as is known in the art. Polymers useful in forming nanoparticles include, but are limited to, poly(lactic acid) (PLA), poly(lactide-co-glycolide), blends of poly(lactide-co-glycolide) and polycarprolactone, diblock polymer poly(l-leucine-block-l-glutamate), diblock and triblock poly(lactic acid) (PLA) and poly(ethylene oxide) (PEO), acrylates, arylamides, polystyrene, and the like. As described for microparticles, nanoparticles may be non-biodegradable or biodegradable. Nanoparticles may be also be made from poly (alkylcyanoacrylate), for example poly(butylcyanoacrylate), in which the peptide is absorbed onto the nanoparticles and coated with surfactants (e.g., polysorbate 80). Methods for making nanoparticles are similar to those for making microparticles and include, among others, emulsion polymerization in continuous aqueous phase, emulsification-evaporation, solvent displacement, and emulsification-diffusion techniques.

Methods of Treatment

Disclosed is a method of inhibiting CN-NFAT signaling in a cell, comprising contacting the cell with a CN inhibitor disclosed herein. Also disclosed is a method of treating a disease in a subject that involves administering to the subject a CN inhibitor disclosed herein.

The disclosed CN inhibitors are useful in the treatment of a number of diseases wherein it is desired to decrease the activity of CN-NFAT signaling. Examples of diseases conditions associated with CN-NFAT signaling include inflammatory diseases, autoimmune disorders, cardiovascular diseases, neurodegenerative diseases, cancer, alopecia, diseases occurring with unwanted angiogenesis, and a diseases occurring with unwanted polimorphonuclear (PMN) infiltration.

The term “immune disorder” or “immune disease” refers to a condition in a subject characterized by cellular, tissue and/or organ injury caused by an immunological reaction of the subject. The term “autoimmune disorder” or “autoimmune disease” refers to a condition in a subject characterized by cellular, tissue and/or organ injury caused by an immunological reaction of the subject to its own cells, tissues and/or organs. Illustrative, non-limiting examples of autoimmune diseases which can be treated with the disclosed CN inhibitor include alopecia areata, ankylosing spondylitis, antiphospho lipid syndrome, autoimmune Addison’s disease, autoimmune diseases of the adrenal gland, autoimmune hemolytic anemia, autoimmune hepatitis, autoimmune oophoritis and orchitis, autoimmune thrombocytopenia, Behcet’s disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, discoid lupus, essential mixed cryoglobulinemia, fibromyalgia-fibro myositis, glomerulonephritis, Graves’ disease, Guillain-Barre, Hashimoto’s thyroiditis, idiopathic pulmonary fibrosis, idiopathic thrombocytopenia purpura (ITP), IgA neuropathy, juvenile arthritis, lichen planus, Meniere’s disease, mixed connective tissue disease, multiple sclerosis, type 1 or immune-mediated diabetes mellitus, myasthenia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynauld’s phenomenon, Reiter’s syndrome, sarcoidosis, scleroderma, progressive systemic sclerosis, Sjogren’s syndrome, Good pasture’s syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, Wegener’s granulomatosis, Anti-Glomerular Basement Membrane Disease, Antiphospho lipid Syndrome, Autoimmune Diseases of the Nervous System, Familial Mediterranean Fever, Lambert-Eaton Myasthenic Syndrome, Sympathetic Ophthalmia, polyendocrinopathies, psoriasis, etc.

The term “immune mediated inflammatory disease” shall be taken to mean any disease mediated by the immune system and characterized by chronic or acute inflammation, resulting from, associated with or triggered by, a dysregulation of the normal immune response e.g. Crohn’s disease, type 1 diabetes mellitus, rheumatoid arthritis, inflammatory bowel disease, psoriasis, psoriatic arthritis, ankylosing spondylitis, systemic lupus erythematosus, Hashimoto’s disease, graft-versus-hostdisease. Sjogren’s syndrome, pernicious anemia, Addison disease, scleroderma, Goodpasture’s syndrome, ulcerative colitis, autoimmune hemolytic anemia, sterility, myasthenia gravis, multiple sclerosis, Basedow’s disease, thrombopenia purpura, Guillain-Barre syndrome, allergy, asthma, atopic disease, arteriosclerosis, myocarditis, cardiomyopathy, glomerular nephritis, hypoplastic anemia, and rejection after organ transplantation.

For the purposes of the methods described herein, “immune disorders” include autoimmune diseases and immunologically mediated diseases. The term “inflammatory disease” refers to a condition in a subject characterized by inflammation, e.g., chronic inflammation. Illustrative, non-limiting examples of inflammatory disorders include, but are not limited to, Celiac Disease, rheumatoid arthritis (RA), Inflammatory Bowel Disease (IBD), asthma, encephalitis, chronic obstructive pulmonary disease (COPD), inflammatory osteolysis, allergic disorders, septic shock, pulmonary fibrosis (e.g., idiopathic pulmonary fibrosis), inflammatory vacultides (e.g., polyarteritis nodosa, Wegner’s granulomatosis, Takayasu’s arteritis, temporal arteritis, and lymphomatoid granulomatosus), post-traumatic vascular angioplasty (e.g., restenosis after angioplasty), undifferentiated spondyloarthropathy, undifferentiated arthropathy, arthritis, inflammatory osteolysis, chronic hepatitis, and chronic inflammation resulting from chronic viral or bacteria infections.

The term “cardiovascular disease or disorder”, as used herein, relates to diseases affecting the heart or blood vessels or both or associated with the cardiopulmonary and circulatory systems including but not limited to ischemia, angina, edematous conditions, artherosclerosis, Coronary Heart Disease, LDL oxidation, adhesion of monocytes to endothelial cells, foam-cell formation, fatty-streak development, platelet adherence, and aggregation, smooth muscle cell proliferation, reperfusion injury, high blood pressure, thrombotic disease, arrhythmia (atrial or ventricular or both); cardiac rhythm disturbances; myocardial ischemia; myocardial infarction; cardiac or vascular aneurysm; vasculitis, stroke; peripheral obstructive arteriopathy of a limb, an organ, or a tissue; reperfusion injury following ischemia of the brain, heart or other organ or tissue, endotoxic, surgical, or traumatic shock; hypertension, valvular heart disease, heart failure, abnormal blood pressure; shock; vasoconstriction (including that associated with migraines); vascular abnormality, inflammation, insufficiency limited to a single organ or tissue.

The term "neurodegenerative disease", as it is used herein, refers to diseases which result from the degeneration or deterioration of nervous tissue, particularly of neurons, leading over time to a dysfunction or to a disability; the term degeneration includes loss of cell viability, loss of cell function and/or loss of the number of cells (neurons or others). Illustrative, non-limiting, examples of neurodegenerative diseases include Alzheimer's disease, Huntington's disease, Parkinson's disease, amyotrophic lateral sclerosis (ALS), multiple sclerosis, etc. In a particular embodiment, said neurodegenerative disease is a disease related to neuronal death caused by a substance which, for example, causes oxidative stress or endoplasmic reticulum stress or apoptosis or excitotoxicity or neuronal death in general.

The term "cancer" refers to a disease characterized by uncontrolled cell division (or by an increase of survival or apoptosis resistance) and by the ability of said cells to invade other neighboring tissues (invasion) and spread to other areas of the body where the cells are not normally located (metastasis) through the lymphatic and blood vessels, circulate through the bloodstream, and then invade normal tissues elsewhere in the body. Depending on whether or not they can spread by invasion and metastasis, tumors are classified as being either benign or malignant: benign tumors are tumors that cannot spread by invasion or metastasis, i.e., they only grow locally; whereas malignant tumors are tumors that are capable of spreading by invasion and metastasis. Biological processes known to be related to cancer include angiogenesis, immune cell infiltration, cell migration and metastasis. As used herein, the term cancer includes, but is not limited to, the following types of cancer: breast cancer; biliary tract cancer; bladder cancer; brain cancer including glioblastomas and medulloblastomas; cervical cancer; choriocarcinoma; colon cancer; endometrial cancer; esophageal cancer; gastric cancer; hematological neoplasms including acute lymphocytic and myelogenous leukemia; T-cell acute lymphoblastic leukemia/lymphoma; hairy cell leukemia; chronic myelogenous leukemia, multiple myeloma; AIDS-associated leukemias and adult T-cell leukemia/lymphoma; intraepithelial neoplasms including Bowen's disease and Paget's disease; liver cancer; lung cancer; lymphomas including Hodglun's disease and lymphocytic lymphomas; neuroblastomas; oral cancer including squamous cell carcinoma; ovarian cancer including those arising from epithelial cells, stromal cells, germ cells and mesenchymal cells; pancreatic cancer; prostate cancer, rectal cancer; sarcomas including leiomyosarcoma, rhabdomyosarcoma, liposarcoma, fibrosarcoma, and osteosarcoma; slun cancer including melanoma, Merkel cell carcinoma, Kaposi's sarcoma, basal cell carcinoma, and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullar carcinoma; and renal cancer including adenocarcinoma and Wilms tumor. Other cancers will-be known to one of ordinary skill in the art.

The term "angiogenesis", also known as vascularisation, refers to the process of formation of new blood vessels from other pre-existing ones. The role of the angiogenesis switch is not limited to the neoplasic diseases pathogenesis, but it has also been related to other non-neoplasic diseases including wet macular degeneration, diabetic retinopathies, diabetes, psoriasis and rheumatoid arthritis.

The term "alopecia" includes the involuntary complete or partial hair loss from the head or body of an individual and includes alopecia areata (AA), alopecia totalis (AT), alopecia universalis (AU), androgenetic alopecia (alopecia androgenetica, or male baldness) or post-chemotherapy alopecia (PCA) or chemotherapy-induced alopecia (CIA). Alopecia areata may include diffuse alopecia areata, alopecia areata monolocularis, alopecia areata multilocularis, and alopecia areata barbae.

The term "polimorfonuclear (PMN) infiltration" relates to the process of infiltration of polymorphonuclear neutrophils into tissues during inflammation. Upon pathogen infection or irritant infliction, local macrophages and other cells sense the insult and produce a panel of inflammatory mediators such as cytokines and chemokines that stimulate the nearby microvasculature and attract large numbers of PMN to migrate across the vascular wall and infiltrate into tissues. After arrival at the inflammatory site. PMN perform phagocytosis and also release powerful anti-pathogen and tissue-damaging reagents to kill pathogens and aberrant cells. Thus, the activity of PMN cells is extremely important for host defense. However, PMN activity can also induce adverse effects. The term "diseases occurring with unwanted polimorphonuclear (PMN) infiltration" relates to diseases due to the adverse effect of PMN infiltration including, without being limited to, inflammatory bowel diseases (IBD), arthritis, some cardiovascular conditions, inflammatory pulmonary and renal diseases, viral/bacterial infection-associated damage, graft versus host disease, transplantation therapy and diseases occurring with unwanted inflammatory diseases. Screening method of the invention.

In some cases, the disclosed compositions can be used in the prevention or treatment of the Acute Respiratory Distress Syndrome (ARDS) or milder forms of Acute Lung Injury (ALI) and Hypoxemic Respiratory Failure. In some cases, the disclosed compositions can be used for preserving or protecting or improving the quality of donor lungs for transplantation either in situ or ex vivo.

Blocking NFAT with $R_{11}$-VIVIT, which is less potent than the disclosed peptides, was shown to protect against experimental colitis in mice (Elloumi H Z, et al. PLoS One 2012 7:e34172), improve immunosuppression during fully mismatched islet allografts between B6 and C3H/HeN mouse strains (Noguchi H, et al. Nat Med 2004 10:305-309), and attenuate both microgliosis and Amyloid β peptide (Aβ) plaque load in treated mice compared to controls in models of Alzheimers disease (Rojanathammanee L. et al. J Neuroinflammation. 2015 12(1):42). Also, $R_{11}$-VIVIT treatment markedly attenuates albuminuria in diabetic db/db mice and alleviates mesangial matrix expansion and podocyte injury (Zhang L, et al. Br J Pharmacol. 2013 170(2):426-39). Studies indicate that NFATc3 and NFATc4 are involved in TLR2 and TLR4 activated TNFα induction. Furthermore, blocking the NFAT function was found to be beneficial in inflammatory bowel disease and pulmonary arterial hypertension (Bonnet S, et al. Proc Natl Acad Sci USA 2007 104:11418-11423; Elloumi H Z, et al. PLoS One 2012 7:e34172).

Pharmaceutical Formulations

Provided are pharmaceutical formulations including the compounds described herein. Pharmaceutical formulations can include a therapeutically effective amount of a compound described herein in combination with one or more pharmaceutically acceptable excipients. Representative excipients include solvents, diluents, pH modifying agents, preservatives, antioxidants, suspending agents, wetting agents, viscosity modifiers, tonicity agents, stabilizing agents, and combinations thereof. Suitable pharmaceutically acceptable excipients are preferably selected from materials that are generally recognized as safe (GRAS) by the FDA, and can be administered to an individual without causing undesirable biological side effects or unwanted interactions.

In certain examples, the pharmaceutical formulation can be a liposomal formulation. For example, provided herein are pharmaceutical formulations that include liposomes formed from a vesicle-forming lipid, and a compound described herein entrapped in the liposomes. A compound entrapped in a liposome can be sequestered in the central aqueous compartment of the liposome, in the aqueous space between liposome lipid bilayers, or within a bilayer of the liposome itself.

Once formed, the liposomal suspension can be lyophilized using methods known in the art. The resulting composition can be in the form of a lyophilized powder. The term "lyophilized powder" refers to any solid material obtained by lyophilization of an aqueous mixture. In some examples, a lyoprotectant, such as sucrose or trehalose, can be added to the liposomal formulation prior lyophilization.

Stability of the lyophilized formulation can be assessed by visual inspection for appearance of cake, the time of reconstitution, and the property of the reconstituted liposomes after various lengths of storage time. In terms of quantitative standard, a liposomal formulation can be assessed for appearance of particulates or turbidity by visual inspection, change in color, mean particle size and polydispersity index by dynamic light scattering on a NICOMP370, zeta potential measurement by Malvern Instrument Zetasizer, percentage of drug encapsulation by Sepharose CL-4B size-exclusion chromatography, chemical integrity of the drug substance and of excipients and appearance of decomposition products by HPLC and by LC-MS. The preferred stability range for the BTZ liposome formulation is less than 20% change in mean particle size and drug encapsulation percentage after 6 months storage at 4 degree compared to immediately reconstituted sample; less than 5% chemical decomposition of the drug product.

Lyophilized formulations can be readily reconstituted prior to administration by adding an aqueous solvent. The reconstitution solvent can be suitable for pharmaceutical administration (e.g., for parenteral administration to a subject). Examples of suitable reconstitution solvents include, without limitation, water, saline, and phosphate buffered saline (PBS).

The compounds and formulations described herein can be administered parenterally (e.g., by intravenous administration or subcutaneous administration). It will be appreciated that the formulation can include any necessary or desirable pharmaceutical excipients to facilitate delivery. The compounds and formulation disclosed herein can also be administered via oral route, by i.p. injection, by intramuscular injection, intratumoral injection, and by airway administration as a micronized solid or liquid aerosol.

The term "administration" and variants thereof (e.g., "administering" a compound) in reference to a compound as described herein means introducing the compound or a formulation thereof into the system of a subject in need of treatment. When a compound as described herein or a formulation thereof is provided in combination with one or more other active agents (e.g., a cytotoxic agent, etc.), "administration" and its variants are each understood to include concurrent and sequential introduction of the compound or formulation thereof and other agents.

In vivo application of the disclosed compounds, and formulations containing them, can be accomplished by any suitable method and technique presently or prospectively known to those skilled in the art. For example, the disclosed compounds can be formulated in a physiologically- or pharmaceutically-acceptable form and administered by any suitable route known in the art including, for example, oral, nasal, rectal, topical, and parenteral routes of administration. As used herein, the term parenteral includes subcutaneous, intradermal, intravenous, intramuscular, intraperitoneal, and intrasternal administration, such as by injection. Administration of the disclosed compounds or formulations can be a single administration, or at continuous or distinct intervals as can be readily determined by a person skilled in the art.

The compounds disclosed herein, and formulations comprising them, can also be administered utilizing liposome technology, slow release capsules, implantable pumps, and biodegradable containers. These delivery methods can, advantageously, provide a uniform dosage over an extended period of time. The compounds can also be administered in their salt derivative forms or crystalline forms.

The compounds disclosed herein can be formulated according to known methods for preparing pharmaceutically acceptable compositions. Formulations are described in detail in a number of sources which are well known and readily available to those skilled in the art. For example, *Remington's Pharmaceutical Science* by E. W. Martin (1995) describes formulations that can be used in connection with the disclosed methods. In general, the compounds disclosed herein can be formulated such that an effective amount of the compound is combined with a suitable carrier in order to facilitate effective administration of the compound. The formulations used can also be in a variety of forms. These include, for example, solid, semi-solid, and liquid dosage forms, such as tablets, pills, powders, liquid solutions or suspension, suppositories, injectable and infusible solutions, and sprays. The preferred form depends on the intended mode of administration and therapeutic application. The formulations also preferably include conventional pharmaceutically-acceptable carriers and diluents which are known to those skilled in the art. Examples of carriers or diluents for use with the compounds include ethanol, dimethyl sulfoxide, glycerol, alumina, starch, saline, and equivalent carriers and diluents. To provide for the administration of such dosages for the desired therapeutic treatment, compositions disclosed herein can advantageously comprise between about 0.1% and 99%, and especially, 1 and 15% by weight of the total of one or more of the subject compounds based on the weight of the total formulation including carrier or diluent.

Formulations suitable for administration include, for example, aqueous sterile injection solutions, which can contain antioxidants, buffers, bacteriostats, and solutes that render the formulation isotonic with the blood of the intended recipient; and aqueous and nonaqueous sterile suspensions, which can include suspending agents and thickening agents. The formulations can be presented in unit-dose or multi-dose containers, for example sealed ampoules and vials, and can be stored in a freeze dried (lyophilized) condition requiring only the condition of the sterile liquid carrier, for example, water for injections, prior to use. Extemporaneous injection solutions and suspensions can be prepared from sterile powder, granules, tablets, etc. It should be understood that in addition to the ingredients particularly mentioned above, the compositions disclosed herein can include other agents conventional in the art having regard to the type of formulation in question.

Therapeutic application of compounds and/or formulations containing them can be accomplished by any suitable therapeutic method and technique presently or prospectively known to those skilled in the art. Further, compounds and compositions disclosed herein have use as starting materials or intermediates for the preparation of other useful compounds and compositions.

Compounds and formulations disclosed herein can be locally administered at one or more anatomical sites, such as sites of unwanted cell growth (such as a tumor site or benign skin growth, e.g., injected or topically applied to the tumor or skin growth), optionally in combination with a pharmaceutically acceptable carrier such as an inert diluent. Compounds and formulations disclosed herein can be systemically administered, such as intravenously or orally, optionally in combination with a pharmaceutically acceptable carrier such as an inert diluent, or an assimilable edible carrier for oral delivery. They can be enclosed in hard or soft shell gelatin capsules, can be compressed into tablets, or can be incorporated directly with the food of the patient's diet. For oral therapeutic administration, the active compound can be combined with one or more excipients and used in the form of ingestible tablets, buccal tablets, troches, capsules, elixirs, suspensions, syrups, wafers, aerosol sprays, and the like.

The tablets, troches, pills, capsules, and the like can also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring can be added. When the unit dosage form is a capsule, it can contain, in addition to materials of the above type, a liquid carrier, such as a vegetable oil or a polyethylene glycol. Various other materials can be present as coatings or to otherwise modify the physical form of the solid unit dosage form. For instance, tablets, pills, or capsules can be coated with gelatin, wax, shellac, or sugar and the like. A syrup or elixir can contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound can be incorporated into sustained-release preparations and devices.

Compounds and formulations disclosed herein, including pharmaceutically acceptable salts, hydrates, or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient, which are adapted for the extemporaneous preparation of sterile injectable or infusible solutions or dispersions, optionally encapsulated in liposomes. The ultimate dosage form should be sterile, fluid, and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent disclosed herein in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents disclosed herein can be applied in as a liquid or solid. However, it will generally be desirable to administer them topically to the skin as formulations, in combination with a dermatologically acceptable carrier, which can be a solid or a liquid. Compounds and agents and formulations disclosed herein can be applied topically to a subject's skin to reduce the size (and can include complete removal) of malignant or benign growths, or to treat an infection site. Compounds and agents disclosed herein can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. Nos. 4,608,392; 4,992,478; 4,559,157; and 4,820,508.

Useful dosages of the compounds and agents and pharmaceutical formulations disclosed herein can be determined by comparing their in vitro activity, and in vivo activity in animal models. Methods for the extrapolation of effective dosages in mice, and other animals, to humans are known to the art; for example, see U.S. Pat. No. 4,938,949.

Also disclosed are pharmaceutical compositions that comprise a compound disclosed herein in combination with a pharmaceutically acceptable carrier. Pharmaceutical compositions adapted for oral, topical or parenteral administration, comprising an amount of a compound constitute a preferred aspect. The dose administered to a patient, particularly a human, should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

By way of non-limiting illustration, examples of certain examples of the present disclosure are given below.

EXAMPLES

The following examples are set forth below to illustrate the methods, compositions, and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

Example 1

Structure-based Optimization of a Peptidyl Inhibitor Against Calcineurin-NFAT Interaction Introduction Calcineurin (CN) is a protein serine/threonine phosphatase involved in T cell signaling. Engagement of T cell-surface receptors with ligands (e.g., an antigen-presenting cell) causes an increase in the cytoplasmic level of calcium, which activates many calmodulin (CaM)-dependent enzymes including CN. CN dephosphorylates multiple phosphoserines on nuclear factor of activated T cell (NFAT), a transcription factor, leading to its nuclear translocation and activation (Crabtree, G. R. Cell 1999 96:611-614; Rao, A, et al. Annu. Rev. Immunol. 1997 15:707-747). The activated NFAT up-regulates the expression of interleukin 2 (IL-2), which in turn activates T-helper lymphocytes, induces the production of other cytokines, and stimulates the immune response. CN is the target of several naturally-occurring macrocycles such as cyclosporine A (CsA) and FK506. These compounds bind to cellular proteins cyclophilin and FKBP12, respectively, and the resulting binary complexes bind to CN and sterically block the access of NFAT and other protein substrates to the CN active site (Liu, J., et al. Cell 1991 66:807-815). CsA and FK506 are clinically used as immunosuppressants in postallogenic organ transplant (Kiani, A., et al. Immunity 2000 12:359-372). Nevertheless, treatment with these drugs is associated with severe side effects including nephrotoxicity and hepatotoxicity (Chapman, J. R. Am. J. Transplant 2011 11:693-697), likely because of their indiscriminate inhibition of CN activity toward all substrates (Sigal, N. H., et al. J. Exp. Med. 1991 173:619-628; Platz, K. P., et al. Transplantation 1994 58:170-178; Hojo, M., et al. Nature 1999 397:530-534). Inhibitors that selectively block the CN-NFAT interaction provide less toxic immunosuppressants.

Previous structural and functional analysis of the CN-NFAT interface has identified a conserved sequence motif among NFAT proteins, PxIxIT (where x is any amino acid), which specifically interacts with a substrate-docking site on CN (Aramburu, J., et al. Mol. Cell 1998 1:627-637). This interaction is critical for dephosphorylation of NFAT and a subset of other CN substrates (Li, H., et al. Trends Cell Biol. 2011 21:91-103; Roy, J., et al. Sci. Signal. 2009 2:re9; Grigoriu, S., et al. PLoS Biol. 2013 11:e1001492). Screening of an oriented peptide library identified a tetradecapeptide, GPHPVIVITGPHEE (VIVIT, SEQ ID NO:47, Table 1), which binds to the docking site on CN with 25-fold higher affinity than the naturally occurring PxIxIT motif (Aramburu, J., et al. Science 1999 285:2129-2133). Expression of peptide VIVIT in mammalian cells effectively blocks the CN-NFAT interaction and its downstream signaling without directly blocking CN enzymatic activity. Attachment to a cell-penetrating peptide renders the peptide cell permeable and active for immunosuppression in transplanted mice (Noguchi, H., et al. Nat. Med. 2004 10:305-309). This observation has inspired investigators to develop peptides and small molecules as selective CN inhibitors (Sieber, M., et al. Cell Commun. Signal. 2009 7:25). However, the reported compounds have somewhat low potency in disrupting the CN-NFAT interaction. In this work, the structural information derived from previous NMR and X-ray studies (Li, H., et al. J. Mol. Biol. 2007 369:1296-1306; Takeuchi, K., et al. Structure 2007 15:587-597; Li, H., et al. J. Mol. Biol. 2004 342:1659-1674) was used as a guide and a structure-based optimization of the VIVIT peptide carried out, which led to ~200-fold improvement in the binding affinity and a highly potent and selective inhibitor against CN ($K_D$=2.6 nM).

Results and Discussion

Figure 2A:
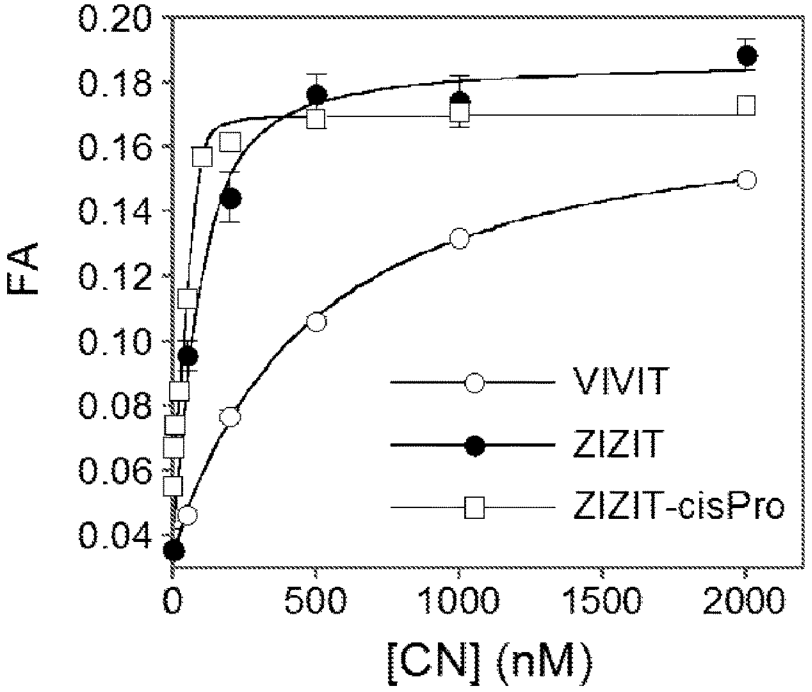
FIGS. 2A and 2B show comparison of the binding affinities of peptides VIVIT, ZIZIT, and ZIZIT-cisPro to CN.

Substitution of tert-Leucine (Tle) for Valine. The structure of the CN-VIVIT complex (Li, H., et al. J. Mol. Biol. 2007 369:1296-1306; Takeuchi, K., et al. Structure 2007 15:587-597) reveals that the PVIVIT core is in an extended conformation and engages in hydrophobic, van der Waals, and hydrogen bonding interactions with CN. The side-chains of three highly-conserved residues, $Pro^4$, $Ile^6$ and $Ile^8$, fit snugly into three well-defined hydrophobic pockets, while the side chains of $Val^5$ and $Val^7$ are largely solvent exposed (FIG. 1A). The PVIVIT core also forms multiple hydrogen bonds between its backbone amides and CN β-strand 14 residues (Li, H., et al. J. Mol. Biol. 2007 369:1296-1306; Li, H., et al. J. Mol. Biol. 2004 342:1659-1674). We suspected that substitution of Tle for $Val^5$ and $Val^7$ of the peptide ligand might improve its the potency and/or bioavailability, based on several considerations. First, the $Val^5$ and $Val^7$ side chains are distant from the hydrophobic surface formed by the side chain of CN $Val^{328}$ for optimal van der Waals interaction. Replacement of the valines with bulkier Tle should result in closer packing between $Tle^5$/$Tle^7$ and $Val^{328}$ side chains and improved van der Waals interactions between them. Second. Tle is frequently used as building blocks for peptidomimetic drugs (Davies, S. J., et al. Bioorg. Med. Chem. Lett. 2003 13:2715-2718; Llinas-Brunet, M., et al. J. Med. Chem. 2004 47:6584-6594) and organocatalysts (Sigman, M. S., et al. J. Am. Chem. Soc. 1998 120:4901-4902), because incorporation of Tle has been shown to substantially improve the target-binding affinity, protease resistance, and/or bioavailability (Bold, G., et al. J. Med. Chem. 1998 41:3387-3401; Perni, R. B., et al. Antimicrob. Agents Chemother. 2006 50:899-909). While the increased stability against proteolysis (and nonenzymatic hydrolysis of the peptide bond) can be attributed to the steric hindrance exerted by the t-butyl side chain, the origin of the increased binding affinity and membrane permeability is less clear. It has been speculated that the bulky t-butyl group may interfere with solvation of the adjacent peptide bonds and therefore decrease the amount of desolvation energy associated with target binding and membrane transport. Both $Val^5$ and $Val^7$ were therefore replaced with Tle and the resulting peptide named "ZIZIT" (where Z=Tle). Peptide ZIZIT was synthesized using standard solid-phase peptide chemistry and 2-(7-aza-1H-benzotriazole-1-yl)-1, 1,3,3-tetramethyluronium hexafluorophosphate (HATU) as the coupling reagent. Peptide ZIZIT bound to CN with a 10-fold higher affinity than VIVIT ($K_D$ values of 43±12 and 477±26 nM, respectively) (Table 3 and FIG. 2A).

TABLE 3

Sequences and dissociation constants of peptidyl ligands

| Peptide | Sequence[a] | SEQ ID NO | $K_D$ (nM)[b] |
|---|---|---|---|
| VIVIT | GPHPVIVITGPHEE | SEQ ID NO: 47 | 477 ± 26 |
| ZIZIT | GPHPZIZITGPHEE | SEQ ID NO: 3 | 43 ± 12 |
| ZIZIT-cisPro | GPHPZIZITGP*HEE | SEQ ID NO: 4 | 2.6 ± 0.8 |
| VAVAA | GPHAVAVAAGPHEE | SEQ ID NO: 6 | >20,000 |

[a]Z, tert-leucine; P*, Cys($\Psi^{Me,Me}$Pro).
[b]$K_D$ values against CN were obtained from FA assay using N-terminal 5(6)-SFX labeled peptides.

Incorporation of Cys($\Psi^{Me,Me}$Pro) as cis-Pro Analog. The structure of the CN-VIVIT complex (Li, H., et al. J. Mol. Biol. 2007 369:1296-1306; Takeuchi, K., et al. Structure 2007 15:587-597), contained a cis peptide bond between $Gly^{10}$ and $Pro^{11}$ of VIVIT (FIG. 1A). The β-turn structure permits the formation of an intricate hydrogen bond network among the side chains of $Asn^{330}$ (of CN) and $His^{12}$ and $Thr^8$ of the VIVIT peptide (Li, H., et al. J. Mol. Biol. 2007 369:1296-1306). Since the trans-configuration of a peptidyl-prolyl peptide bond is energetically more stable (Wedemeyer, W. J., et al. Biochemistry 2002 41:14637-14644), it was envisioned that preorganization of the $Gly^{10}$-$Pro^{11}$ peptide bond into the cis-configuration should increase the binding affinity. 2,2-Dimethylthiazolidine [Cys($\Psi^{Me,Me}$Pro)] has previously been used as a proline analog; when it is incorporated into a peptide, the preceding peptide bond is sterically locked into the cis-configuration (Dumy, P., et al. J. Am. Chem. Soc. 1997 119:918-925; Chierici, S., et al. Org. Biomol. Chem. 2004 2:2436-2441). We thus designed peptide ZIZIT-cisPro (Table 3 and FIG. 1B) by replacing $Pro^{11}$ of ZIZIT with Cys($\Psi^{Me,Me}$Pro).

Scheme 1. Synthesis of peptide ZIZIT-cisPro

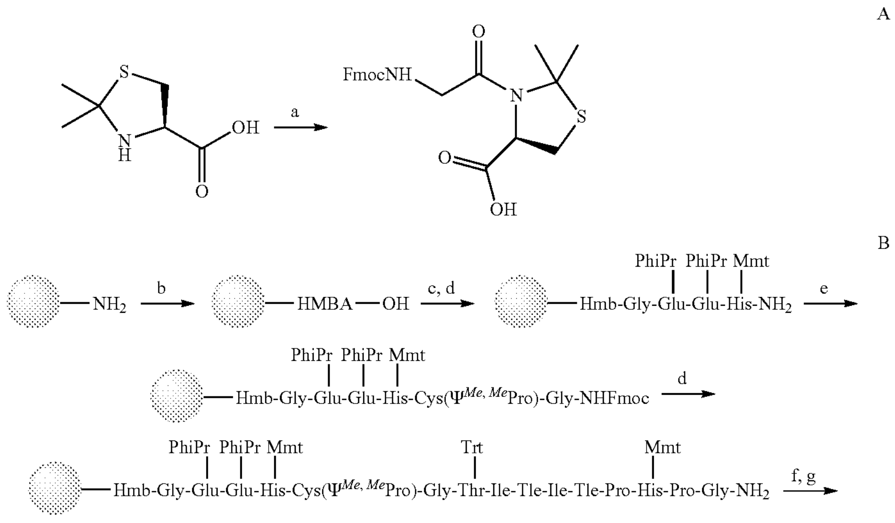

H-Gly-Pro-His-Pro-Tle-Ile-Tle-Ile-Thr-Gly-Cys($\Psi^{Me,Me}$Pro)-His-Glu-Glu-Gly-Propyl ZIZIT-cisPro Reagents and Conditions: (a) Fmoc-Gly-F/DIPEA; (b) 4-hydroxymethylbenzoic acid (HMBA)/HATU; (c) Fmoc-Gly-OH/DIC; (d) solid-phase Fmoc/HATU chemistry; (e) Fmoc-Gly-Cys($\Psi^{Me,Me}$Pro)-OH/PyBop; (f) 1% TFA; and (g) propylamine/DMF.

Synthesis of peptide ZIZIT-cisPro is outlined in Scheme 1 above. The sterically hindered secondary amine of 2,2-dimethyl-1,3-thiazolidine-4-carboxylic acid [H-Cys($\Psi^{Me,Me}$Pro)-OH] is poorly reactive and cannot be directly incorporated into peptides through solid-phase synthesis. Thus, the pseudo-proline was first prepared as the Fmoc-protected dipeptide, which was readily introduced into peptides using benzotriazol-1-yl-oxytripyrrolidinophosphonium hexafluorophosphate (PyBop) as the coupling reagent.[27] The dipeptide, Fmoc-Gly-Cys($\Psi^{Me,Me}$Pro)-OH, was prepared in 69% yield by condensing Fmoc-protected glycyl fluoride and H-Cys($\Psi^{Me,Me}$Pro)-OH.[27] Because Cys ($\Psi^{Me,Me}$Pro) is unstable under strongly acidic conditions (e.g. 100% TFA), acid-labile side-chain protecting groups 4-methyltrityl (Mmt), 2-phenylisopropyl (PhiPr), and trityl (Trt) were employed for His, Glu, and Thr residues, respectively. After the fully protected peptide was synthesized on solid phase, these side-chain protecting groups were removed by treatment with a mildly acidic condition (1% TFA, 5% triisopropylsilane in DCM, 2 h), which did not significantly damage the Cys($\Psi^{Me,Me}$Pro) moiety. The deprotected peptide was released from the solid support by aminolysis with 1:1 (v/v) propylamine/DMF and purified to near homogeneity by reversed-phase HPLC (FIG. 5).

The binding affinity of ZIZIT-cisPro for CN was determined by fluorescence anisotropy (FA). Incorporation of the cis-proline analog further increased the binding affinity of ZIZIT for CN by ~20-fold, producing a highly potent peptidyl inhibitor against CN ($K_D$=2.6 nM, FIG. 2A). The magnitude of affinity improvement is consistent with increasing the cis peptidyl-prolyl bond population from its normal abundance (5-10%) to ~100% in ZIZIT-cisPro (Dumy, P., et al. J. Am. Chem. Soc. 1997 119:918-925; Chierici, S., et al. Org. Biomol. Chem. 2004 2:2436-2441; Wohr, T., et al. J. Am. Chem. Soc. 1996 118:9218-9227).

Figure 2B:
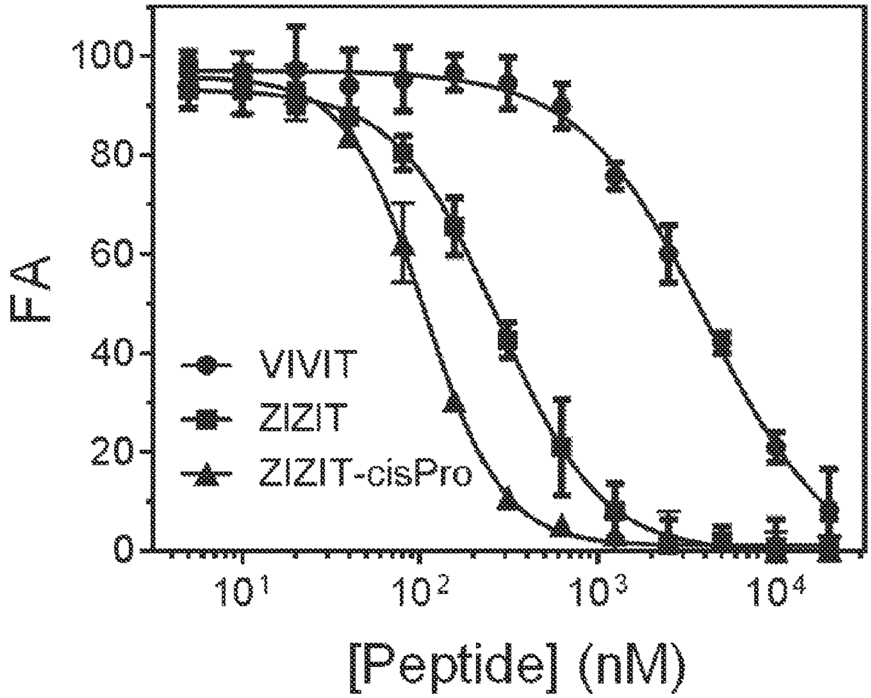

Binding Site, Selectivity, and Serum Stability of ZIZIT-cisPro. To determine whether ZIZIT and ZIZIT-cisPro bind to the same site as VIVIT on CN, the FA assay was modified to test the competition among the three peptides for binding to CN. Briefly, peptide ZIZIT, which has an intermediate binding affinity ($K_D$=43 nM), was labeled with fluorescein isothiocyanate (FITC) and tested for binding to CN in the presence of increasing concentrations of unlabeled VIVIT, ZIZIT, or ZIZIT-cisPro. All three peptides inhibited the binding of FITC-ZIZIT to CN in concentration-dependent manners, with $IC_{50}$ values of 4100±100, 280±90, and 110±90 nM, respectively (FIG. 2B). These data suggest that all three peptides bind to the same site (or overlapping sites) on CN. Further, the ability of ZIZIT-cisPro to largely eliminate FITC-ZIZIT binding at stoichiometric amounts (~150 nM, which was also the CN concentration used) suggests that ZIZIT-cisPro binds to a single site on CN.

To determine whether ZIZIT-cisPro is a specific ligand of CN, it was tested for binding to five arbitrarily selected proteins by FA, including bovine serum albumin (BSA), protein-tyrosine phosphatases 1B (PTP1B) and SHP1, K-Ras G12V, and the $SH_2$ domain of Grb2. ZIZIT-cisPro bound weakly to PTP1B ($K_D$~9 μM) and SHP1 ($K_D$>15 μM) but not to the other three proteins up to 15 μM protein concentration (FIG. 6), indicating that it is a selective ligand of CN.

Figure 3:
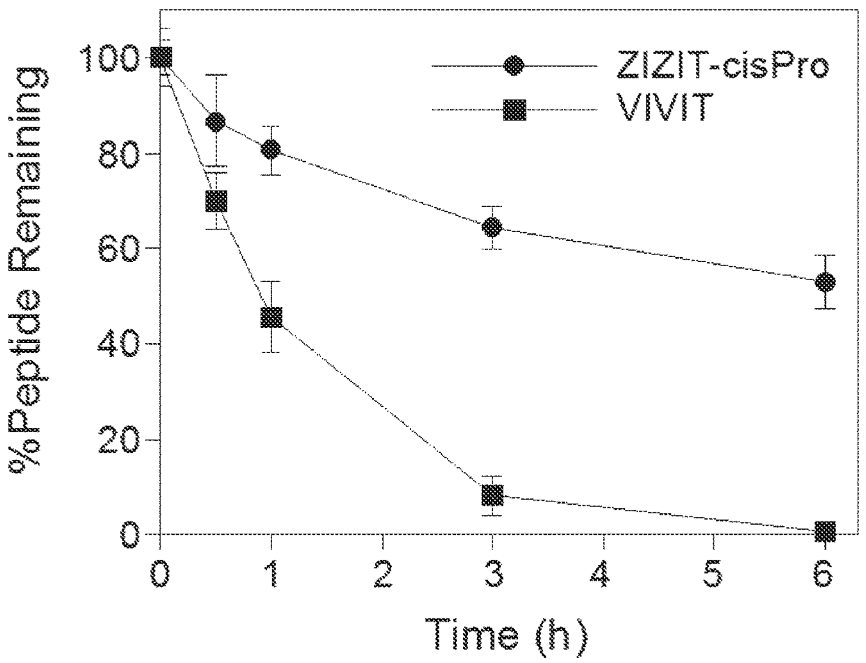
FIG. 3 is a graph comparing the serum stability of peptides VIVIT and ZIZIT-cisPro at 37° C.

The proteolytic stability of peptides VIVIT and ZIZIT-cisPro was assessed by incubating the peptides in diluted human serum (25%) at 37° C. and monitoring the amounts of remaining peptides by HPLC. The VIVIT peptide was degraded with a half-life of ~1 h and to completion in 6 h (FIG. 3). In contrast, ~60% of ZIZIT-cisPro remained intact after 6 h of incubation. Thus, incorporation of the Tle and/or cis-Pro residues substantially improved the proteolytic stability of the CN ligand.

Molecular Modeling. To gain some mechanistic insight into the observed affinity enhancement, molecular dynamic (MD) simulations were carried out on the CN-ZIZIT-cisPro complex. To provide some information about how the new ligand would interact with the CN surface, a molecular docking study was conducted; this began using the available crystal structure of the CN-VIVIT complex (pdbID: 2p6b) (Li, H., et al. J. Mol. Biol. 2007 369:1296-1306) and replacing the ligand with ZIZIT-cisPro. Following the construction of ZIZIT-cisPro ligand and energy minimization as detailed in the Experimental Section, MD simulations were performed to obtain the docked conformation (Luechapanichkul, R., et al. J. Biol. Chem. 2013 288:6498-6510). Analysis of the root mean square deviation (RMSD) between the crystal structure and MD protein showed no deviation indicative of sudden, chaotic structural fluctuations (FIG. 7). Further, ZIZIT-cisPro remained associated with the binding site on the CN surface throughout the simulation, as indicated by the number of hydrogen bonds between the ligand and the protein (FIG. 8).

Figure 1B:
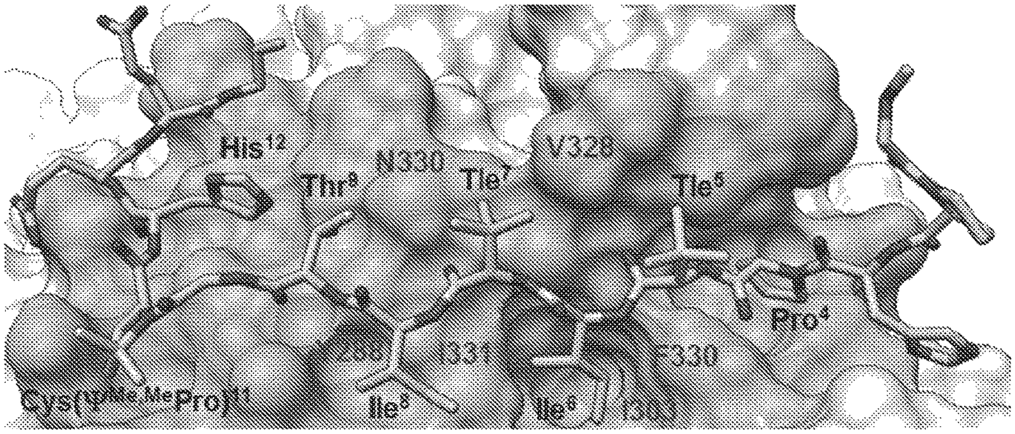
FIG. 1B shows simulated binding of peptide ZIZIT-cisPro to CN as derived from MD simulations. CN is displayed as the van der Waals surface with the binding surface shaded darker. Key ligand residues are labeled in three-letter codes, while CN residues are labeled in single-letter codes. Tle=tert-leucine.
Figure 1C:
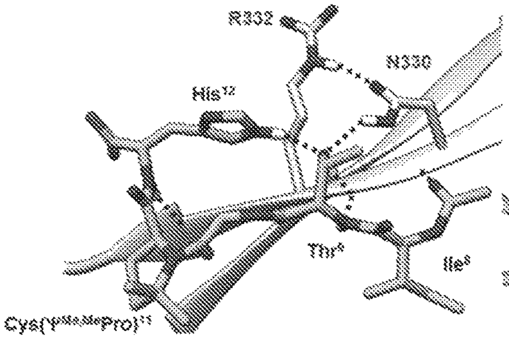
FIG. 1C is a close-up view of the hydrogen-bond network between CN and ligand residues adjacent to the cis-proline analog.
Figure 1D:
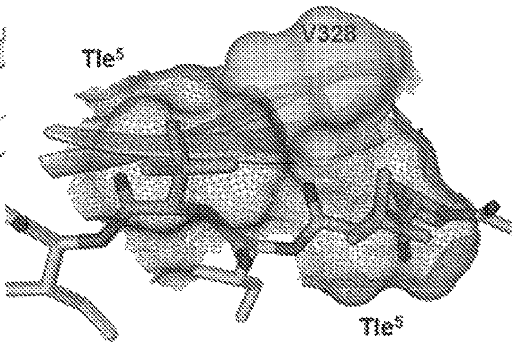
FIG. 1D shows van der Waals surface contours of $Val^{328}$ of CN and $Tle^5$ and $Tle^7$ of the peptide ligand.

ZIZIT-cisPro adopts a virtually identical conformation to that of VIVIT in the crystal structure (FIG. 1A, 1B). The side chains of $Ile^6$ and $Ile^8$ are clearly accommodated in hydrophobic pockets formed by $Met^{329}$/$Met^{290}$/$Ile^{303}$ and $Tyr^{288}$/$Met^{290}$/$Ile^{331}$, respectively. ZIZIT-cisPro engages in the same set of hydrogen bonds with CN as VIVIT. The $Gly^{10}$-Cys($\Psi^{Me,Me}$Pro)$^{11}$ peptide bond is indeed in its cis-configuration, thus permitting the formation of the hydrogen bond network between ligand side chains of $His^{12}$ and $Thr^9$ and CN residues $Arg^{332}$ and $Asn^{330}$ (FIG. 1C). The geminal dimethyl groups of the proline analog are oriented away from the protein surface and do not appear to experience any steric clashes with any protein residue. In contrast to the CN-VIVIT structure, in which $Val^5$ and $Val^7$ side chains are solvent exposed,[16] the additional side chain methyl groups in the CN-ZIZIT-cisPro complex result in close packing of the $Tle^5$ and $Tle^7$ side chains against the side chain of $Val^{328}$ (FIG. 1D). In fact, the Tle side chains are ~1 Å closer to the $Val^{328}$ side chain than those of $Val^5$ and $Val^7$. These results suggest that enhanced van der Waals interactions and/or hydrophobic effects between the Tle side chains and $Val^{328}$ contribute significantly to the observed high potency of the ZIZIT-cisPro ligand. We also calculated the solvent accessible surface area (SASA) of both VIVIT and ZIZIT-cisPro peptides when they are bound to the CN protein using the trajectories derived from the 20 ns MD simulations. The calculated SASA values for VIVIT (2123±29 Å$^2$) and ZIZIT-cisPro (1970±30 Å$^2$) indicate that ZIZIT-cisPro peptide is less solvated than VIVIT peptide in CN-bound states, providing further support that ZIZIT-cisPro engages in greater van der Waals and/or hydrophobic interactions with the CN protein than the parent peptide.

Figure 4A:
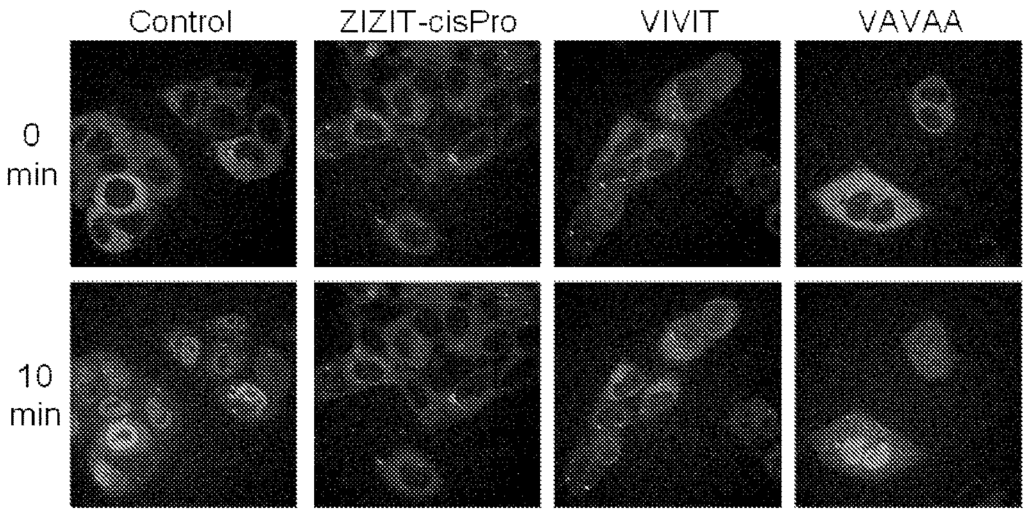
FIG. 4A shows time-lapse live cell confocal microscopic imaging of HeLa cells stably transfected with GFP-NFAT after stimulation with ionomycin and in the absence or presence of different CN inhibitors (500 nM).
Figure 4B:
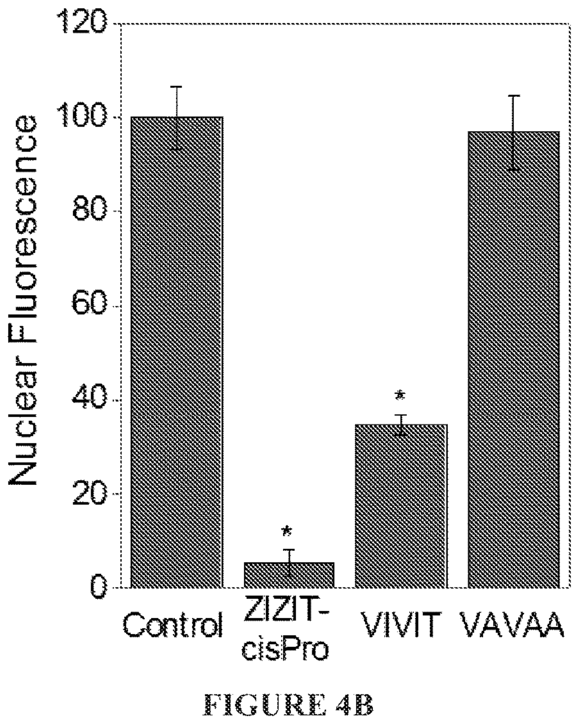
FIG. 4B is a bar graph showing relative potencies of the CN inhibitors in blocking the nuclear translocation of GFP-NFAT. The increase in fluorescence intensity in the nuclear region after 10 min of stimulation with ionomycin was measured and compared to that of control cells (untreated with CN inhibitor; 100%). *, P<0.001 compared with control; two tailed t-test. Data reported represent the mean±SD from at least 30 cells. All CN inhibitors contained $R_{11}$ on their N-termini.

Inhibition of Nuclear Translocation of NFAT. To test whether the increased binding affinity of ZIZIT-cisPro translates into improved efficacy in cellular assays, it was conjugated to a polybasic cell-penetrating peptide, $R_{11}$ (SEQ ID NO:7). First, peptide ZIZIT-cisPro was modified at its N-terminus with a bifunctional linker succinimidyl 3-(2-pyridyldithio)propionate (SPDP) (FIG. 9). The resulting peptide was conjugated to $R_{11}$, which was synthesized with a C-terminal cysteine, via a disulfide exchange reaction. Also prepared were a $R_{11}$-VIVIT and a negative control peptide, $R_{11}$-VAVAA, which contains replacement of three key CN-binding residues ($Ile^6$, $Ile^8$, and $Thr^9$) with alanine and has no detectable binding to CN as judged by FA analysis (Table 3). HeLa cells stably transfected with a green fluorescent protein-NFAT1 fusion (GFP-NFAT) (Gwack, Y., et al. Nature 2006 441:646-650) were treated with the peptides in the absence and presence of ionomycin and the intracellular distribution of green fluorescence was monitored by live-cell confocal microscopy (FIG. 4A) (Noguchi, H., et al. Nat. Med. 2004 10:305-309). In control cells (untreated with either ionomycin or peptide), GFP-NFAT was localized predominantly in the cytosol with minimal signal in the nuclear region. Treatment of cells for 10 min with ionomycin, which raises the intracellular $Ca^{2+}$ concentration and activates CN activity, caused translocation of GFP-NFAT into the nucleus, as observed by time-lapse live-cell confocal microscopic imaging. However, incubation of cells with 500 nM $R_{11}$-ZIZIT-cisPro prior to the treatment with ionomycin almost completely blocked the nuclear translocation of GFP-NFAT (~95% inhibition) (FIG. 4B). This potency of peptide $R_{11}$-ZIZIT-cisPro is similar to that of FK506 in the translocation assay (Noguchi, H., et al. Nat. Med. 2004 10:305-309). Under the same conditions, $R_{11}$-VIVIT resulted in ~65% inhibition of the nuclear translocation. As expected, peptide $R_{11}$-VAVAA had no detectable effect on the ionomycin-stimulated GFP-NFAT translocation.

Conclusion. The CN-binding affinity of peptide VIVIT was improved by ~200-fold. With a $K_D$ value of 2.6 nM, ZIZIT-cisPro ranks among some of the most potent CN inhibitors reported to date (Sieber, M., et al. Cell Commun. Signal. 2009 7:25). ZIZIT-cisPro should be less toxic than CsA and FK506, because it should only block the dephosphorylation of a subset of the CN substrates and have no effect on the peptidyl-prolyl isomerase activity of immunophilins. The steric bulk of Tle and/or the cis-Pro analog also improve the proteolytic stability of the peptide. Peptide $R_{11}$-ZIZIT-cisPro may be further developed into an efficacious but less toxic alternative to FK506 and CsA.

Materials and Methods

Materials. Reagents for peptide synthesis were purchased from NovaBiochem (La Jolla, Calif.), Anaspec (San Jose, Calif.), Peptides International (Louisville, Ky.), or Chem-Impex International Inc. (Wood Dale, Ill.). SPDP was obtained from Thermo Scientific (Rockford, Ill.). 5(6)-fluorescein-6(5)-carboxamidohexanoic acid, succinimidyl ester (5(6)-SFX, F-6129) was from Life Technologies (Carlsbad, Calif.). Glass-bottom dishes (35-mm) were purchased from MatTek (Ashland, Mass.). Cell culture media, fetal bovine serum, 0.25% trypsin-EDTA, Dulbecco's phosphate-buffered saline (DPBS) (2.67 mM potassium chloride, 1.47 mM potassium phosphate monobasic, 137 mM sodium chloride, 8.06 mM sodium phosphate dibasic.), and other chemical reagents were purchased from Sigma-Aldrich (St. Louis, Mo.).

Cell Culture. The generation of HeLa cells stably expressing GFP-NFAT has previously been described (Gwack, Y., et al. Nature 2006 441:646-650). The cells were maintained with 10% FBS supplemented Dulbecco's modified eagle medium (DMEM) in a humidified incubator at 37° C. with 5% $CO_2$.

Peptide Synthesis, Labeling, and Conjugation. Peptides were synthesized on Rink Resin LS (0.2 mmol/g) using standard Fmoc chemistry. The typical coupling reaction contained 5 equiv of Fmoc-amino acid, 5 equiv of HATU and 10 equiv of diisopropylethylamine (DIPEA) and was allowed to proceed with mixing for 1 h. The peptides were deprotected and released from the resin by treatment with 92.5:2.5:2.5:2.5 (v/v) TFA/phenol/water/triisopropylsilane for 2 h. The peptides were triturated with cold ethyl ether and purified by reversed-phase HPLC equipped with a $C_{18}$ column. The authenticity of each peptide was confirmed by MALDI-TOF mass spectrometry. Peptide labeling with 5(6)-SFX was performed by dissolving the purified peptides (1 mg) in 300 μL of 1:1 (v/v) DMF/150 mM sodium bicarbonate (pH 8.5) followed by the addition of 10 μL of 5(6)-SFX in DMSO (100 mg/mL). After 1 h reaction, the reaction was quenched and purified by HPLC.

The dipeptide Fmoc-Gly-Cys($\Psi^{Me,Me}$Pro)-OH was prepared by mixing Fmoc-Gly-F (420 mg, 1.4 mmol) (Kaduk, C., et al. Lett. Pep. Sci. 1995 2:285-288) with 1 equiv 2,2-dimethyl-L-thiazolidine-4-carboxylic acid hydrochloride (277 mg, 1.4 mmol) and 2 equiv of DIPEA (0.49 mL, 2.8 mmol) in anhydrous DCM (20 mL). After 1 h reaction under argon atmosphere, the mixture was washed with 20 mL of aqueous solution of 10% (w/v) citric acid, dried, and concentrated in vacuo. The crude product was purified by silica gel column chromatography to give 425 mg of Fmoc-Gly-Cys($\Psi^{Me,Me}$Pro)-OH (69% yield). $^1$H NMR (250 MHz, $CDCl_3$): δ 7.76-7.73 (m, 2H), 7.59-7.56 (m, 2H), 7.42-7.26 (m, 4H), 5.76 (br, 1H), 4.77-4.75 (m, 1H), 4.36-4.17 (m, 3H), 4.03-3.94 (m, 2H), 3.38-3.29 (m, 2H), 1.89 (s, 3H), 1.84 (s, 3H). ESI-MS: m/z calculated for $C_{23}H_{24}N_2O_5S$ 440.14, found 463.13 ([M+N$^+$]).

The synthesis of Cys($\Psi^{Me,Me}$Pro)-containing peptide was similarly performed on Rink Resin LS (0.2 mmol/g), which was first modified with a 4-hydroxymethylbenzoic acid (HMBA) linker. Coupling of the first residue to the HMBA linker was carried out with 5 equiv of N,N'-diisopropylcarbodiimide (DIC), 5 equiv of Fmoc-amino acid, and 5 equiv of hydroxybenzotriazole (HOBt) for 3 h. Fmoc-Gly-Cys ($\Psi^{Me,Me}$Pro)-OH was incorporated into the peptide using 2 equiv of the Fmoc-dipeptide, 2 equiv of PyBop, and 2 equiv of HOBt. Fmoc-His(Mmt)-OH, Fmoc-Thr(Trt)-OH, and Fmoc-Glu(O-2-PhiPr)-OH were coupled to the growing peptide chain using standard Fmoc chemistry. After the peptide synthesis was complete, the resin was treated with 1% TFA and 5% triisopropylsilane in DCM for 2 h. The peptide was then released from the solid support with 1:1 (v/v) propylamine/DMF for 3 h, purified, and labeled as described above.

To conjugate a peptide to $R_{11}$, the peptide containing a free N-terminal amine (~10 μmol) was dissolved in 200 μL of 50 mM phosphate buffer (pH 8.0) and mixed with 1 equiv of SPDP dissolved in 100 μL of DM F. After incubation for 4 h at room temperature, 1 equiv of Ac-$R_{11}$-Cys-$NH_2$ (dissolved in water) was added to the mixture (FIG. 9). After incubation for an additional 12 h, the crude product was purified by reversed-phase HPLC and the peptide identity was confirmed by MALDI-TOF MS analysis.

Fluorescence Anisotropy. The protein for FA experiment was purified as glutathione S-transferase fusion protein from *Escherichia coli* BL21 cells and purified on a glutathione-Sepharose column as previously described (Kang, S., et al. J. Biol. Chem. 2005 280: 37698-37706). FA experiments were performed by incubating 100 nM fluorescein-labeled peptide with varying concentrations of CN in 20 mM HEPES (pH 7.4), 150 mM NaCl, 2 mM $Mg(OAc)_2$, and 0.1% bovine serum albumin for 2 h at room temperature. The FA values were measured on a Molecular Devices Spectramax M5 spectrofluorimeter, with excitation and emission wavelengths at 485 and 525 nm, respectively. Dissociation constants ($K_D$) were determined by plotting the FA values as a function of CN concentrations. The titration curves were fitted to the following equation (Origin 9.0)

$$Y=(A_{min}+(A_{max}*Q_b/Q_f-A_{min})*((L+x+K_D)-\mathrm{sqrt}((L+x+K_D)^\wedge 2-4*L*x))/2/L)/(1+(Q_b/Q_f-1)*((L+x+K_D)-\mathrm{sqrt}((L+x+K_D)^\wedge 2-4*L*x))/2/L)$$

where Y is the FA value at a given concentration x of CN; L is the peptide concentration; $Q_b/Q_f$ is the correction factor for fluorophore-protein interaction; $A_{max}$ is the maximum FA value when all the peptide are bound to CN; while $A_{min}$ is the minimum FA value when all of the peptides are free. The competition experiments were similarly carried out, except that each reaction contained fixed concentrations of FITC-ZIZIT (100 nM) and CN (150 nM) but varying concentrations of the competing peptide (0-20 μM).

Serum Stability Test. The stability tests were carried by modifying a previously reported procedure (Nguyen, L. T., et al. PLoS One 2010 5:e12684). Diluted human serum (25%) was centrifuged at 15,000 rpm for 10 min in a microcentrifuge and the supernatant was collected. A peptide stock solution was diluted into the supernatant to a final concentration of 50 μM and incubated at 37° C. At various time points (0-6 h), 200-μL aliquots were withdrawn and mixed with 100 μL of 15% trichloroacetic acid and incubated at 4° C. overnight. The final mixture was centrifuged at 15,000 rpm for 10 min in a microcentrifuge, and the supernatant was analyzed by reversed-phase HPLC equipped with a $C_{18}$ column (Waters). The amount of remaining peptide (%) was determined by integrating the area underneath the peptide peak (monitored at 214 nm) and compared with that of the control reaction (no serum).

Molecular Modeling. Simulation was first prepared by editing the crystal structure of VIVIT/CN (pdbID: 2p6b) in UCSF Chimera software suite (Pettersen, E. F., et al. J. Comput. Chem. 2004 13:1605-1612) to include ZIZIT-cisPro structural modifications. As the GROMACS implemented ffAMBER03 (Sorin, E. J., et al. Biophys. J. 2005 88:2472-2493; DePaul, A. J., et al. Nucleic Acids Res. 2010 38:4856-4867) force field did not include the proper sulfur topology, it was generated using ANTECHAMBER (DePaul, A. J., et al. Nucleic Acids Res. 2010 38:4856-4867; Wang, J., et al. J. Comput. Chem. 2004 25:1157-1174) from AmberTools13 via acpype (Sousa da Silva, A. W., et al. BMC Res. Notes 2012 5:367). Hydrogen types, C—H bond lengths, bond length, bond angle (θ), GROMACS bond angle force ($c_\theta$), dihedral partners (i, k, l), phase angle (φ) and GROMACS dihedral force constant ($k_d$) were calculated and imported from the topology generated by ANTECHAMBER/GAFF (Jójárt, B., et al. J. Comput. Chem. 2007 28:2051-2058). All charges and protonation sites were calculated at pH 7.4. A complete topology and the requisite GROMACS files for the protein-ligand system were generated using pdb2gmx with parameters specified to use the AMBER03 force field. The system was placed within a dodecahedral periodic box, each dimension 9.091 nm long, filled with copies of 216 equilibrated TIP3P (Jorgensen, W. L., et al. J. Am. Chem. Soc. 1983 105:1407-1413) water molecules and sufficient counter-ions for system neutralization. The system underwent two steps of energy minimization using steepest decent, first with only solvent relaxing, then the entire system followed by a heating process for which the temperature is increased from 0 to 300K. The system then underwent two more phases of equilibration via MD, first using NVT (isothermal) conditions for 200 ps and then NPT (isothermal-isobaric with pressure control via the Parrinello-Rahman algorithm) conditions for 200 ps. The production MD simulations were performed under NPT conditions for 20 ns, and the final trajectory was used to determine the bound ligand conformation, hydrogen bond patterns, average distance, and RMSD. The solvent accessible surface area (SASA) of VIVIT and ZIZIT-cisPro peptides was calculated using the vmd sasa plugin (Humphrey, W., et al. J. Mol. Graphics 1996 14:33-38) and averaged over the 20 ns CN-bound MD simulation; the resulting value is reported as the SASA value.

GFP-NFAT Translocation Assay. HeLa cells ($7\times10^4$) that stably transfected with GFP-NFAT were seeded in 35-mm glass-bottom dishes. On the day of the experiment, the cells were first incubated for 2 h with 500 nM of $R_{11}$-ZIZIT-cisPro, $R_{11}$-VIVIT, or $R_{11}$-VAVAA in the presence of full growth media. Afterwards, the cells were incubated with 1 μM ionomycin containing phenol-red free DMEM supplemented with 2% FBS. Time-lapse live-cell confocal microscopic imaging of cells was performed using Visitech Infinity 3 HAWK confocal microscopy with 60× oil objective. The same imaging parameters were used for nuclear fluorescence intensity quantifications (MetaMorph).

Example 2

Structure-based Optimization of a Peptidyl Inhibitor Against Calcineurin-NFAT Interaction Detailed Procedure for Molecular Modeling. The initial CN/ZIZIT-cisPro complex was prepared through editing an existing crystal structure of CN bound to VIVIT (pdbID: 2P6B) by using the "Build Structure" functionality in UCSF Chimera. The additional atoms of the modified residues, 2,2-dimethylthiazolidine and tert-glycine, were incorporated using the bond lengths and angles specified in amber99 for the initial spatial coordinates. Parameterization of the modified residues was performed via antechamber with parameters from the General Amber Force Field (GAFF) in AmberTools13 to generate a set of values that would be consistent with the Amber03 force field used for the rest of the simulation. The resulting topology files were verified using the parmchk utility in AmberTools13 to ensure there were no incomplete entries. The topologies generated using AmberTools13 were converted to GROMACS-compatible *.top files using the utility acpype, yielding a final topology for the modified residues with the requisite structural information: hydrogen types, C—H bond lengths, heavy atom bond lengths, bond angle (θ), GROMACS bond angle force ($c_\theta$), dihedral partners (i, j, k, l), phase angle (φ), GROMACS dihedral force constant ($k_d$) and charges at pH 7.4. Topologies for standard residues and the protein were obtained through the GROMACS command pdb2gmx -f *.pdb -o *.gro -p *.top -water tip3p and interactive selection of the Amber03 force field, converting the PDB files output by Chimera into *.gro structure files for GROMACS. Incorporation of the modified residue topology was accomplished by using an #include flag in the whole-system topology file. The system was prepared with the command editconf-f *.gro -o *.gro -bt dodecahedron -d 1| specifying a dodecahedral periodic box (-bt) with a distance (-d) of 1 nm between solvent molecules and box, yielding a periodic box with x, y and z vectors length 9.091 nm. This system was solvated using the command genbox -cp *.gro -cs tip3p.gro -o *.gro -p *.top, filling the box with 6386 pre-equilibrated TIP3P water molecules from tip3p.gro included with GROMACS, followed by automatic removal of any solvent molecules intruding into the protein/vdW radius of constituent atoms. System was neutralized using genion -s *.tpr -o *.gro -p *.top -neutral, replacing solvent molecules with sufficient $Cl^-$ or $Na^+$ ions for system neutralization. All molecular dynamics runs were performed using mdrun and GROMACS binary runtime *.rtp files generated by grompp. First, steepest descent energy minimization was performed, keeping all protein and ligand atoms restrained using the restraints generated by GROMACS in posre.itp files, then only the protein backbone was restrained for an additional steepest decent minimization run; both runs were performed until the next force step was too small to be calculated using single-precision floating point values. Constant pressure (NVT) equilibration was then performed for 200 ps with a timestep of 2 fs. Charge was described using the particle-mesh Ewald (PME) method, with an interaction cutoff of 0.9, grid spacing of 0.12 and order 6; van der Waals interactions had a cut-off distance of 0.9. Temperature control was provided by a modified Berendsen thermostat (option tcoupl=v_rescale) with a reference temperature of 300 K and 0.1 ps timestep; the system was divided into coupling groups for solvent/non-solvent for improved temperature accuracy. Backbone was restrained using posre.itp and initial velocities were assigned from a Maxwell distribution. 200 ps of NPT equilibration with a 2 fs time step followed, using the same PME/vdW cutoffs. Pressure control was provided via the Parrinello-Rahman algorithm (pcoupl=parrinello-rahman) with tau_p=2.0, compressibility=4.5e-5, and ref_p=1.0. The velocities from the proceeding NVT equilibration run were maintained. Production MD was performed under NPT conditions for 20 ns with a 2 fs time step, maintaining the velocities generated from NPT equilibration and LINCS constraints. The resulting MD trajectory file was used for the remaining calculations. The trajectory was corrected for periodic boundary conditions using trjconv -pbc mol -center, with all protein+ligand selected for centering. Conformation was obtained by extracting timesteps from the full trajectory with trjconv corresponding to energy minima as found using the MD *.edr energy file and g_energy. Hydrogen bonding was analyzed over the complete trajectory using g_hbond, to ensure only interchain hydrogen bonds were being analyzed, two groups were provided as command-line options to g_hbond corresponding to the atom number ranges for the ligand and protein and the program was restricted to only to calculating interactions between these two groups, precluding any intrachain hydrogen bonding from being calculated. RMSD values were calculated using g_rms following a least-squares fit of the system at each 2 fs timestep to the original CN/VIVIT crystal structure PDB file. Atomic distances were calculated by specifying the atom identifiers of interest in an index file and then using g_dist to calculate.

The SASA values were calculated using sasa plugin of vmd software with a probe radius of 1.4 Å. The sasa plugin uses the Shrake-Rupley algorithm (J. Mol. Biol. 1973, 79, 351-371) which returns the solvent-accessible surface area of atoms in the selection using the assigned radius for each atom, extending each radius by probe radius to find the points on a sphere that are exposed to solvent. The SASA values were calculated for each step in the trajectory from which the mean and standard deviation were computed.

Example 3

Cyclic Cell Penetrating Peptide-ZIZIT Conjugates

In the Examples above, the ZIZIT peptide was delivered into cells by conjugating it to the canonical cell penetrating peptide R11. The efficacy of cellular delivery is limited. A significantly more potent Calcineurin inhibitor was prepared by conjugating the ZIZIT peptide with a cyclic cell penetrating peptide, CP9. Table 4 provides a list of compound prepared, and Figures

TABLE 4

Cyclic cell penetrating peptides

| Sample ID | Sequence | SEQ ID NO:* |
|---|---|---|
| CP9-ZIZIT | cyclo(fΦRrRrQ)-$PEG_2$-GPHPZIZITGPHEEK-$NH_2$ | SEQ ID NO: 3 |
| CP9-VAVAA | cyclo(fΦRrRrQ)-$PEG_2$-GPHPVAVAAGPHEEK-$NH_2$ | SEQ ID NO: 6 |
| CP9-ZIZIT-Biotin | cyclo(fΦRrRrQ)-$PEG_2$-GPHPZIZITGPHEEK($PEG_4$-Biotin)-$NH_2$ | SEQ ID NO: 3 |
| CP9-VAVAA-Biotin | cyclo(fΦRrRrQ)-$PEG_2$-GPHPVAVAAGPHEEK($PEG_4$-Biotin)-$NH_2$ | SEQ ID NO: 6 |

f = D-phenylalanine,
Φ = L-2-naphthylalanine,
Z = L-tert-leucine,
*for underlined sequence The peptides were synthesized following standard Fmoc chemistry on Rink Resin. The typical coupling reaction contained 5 equiv of Fmoc-amino acid, 5 equiv of HATU, and 10 equiv of DIPEA and was allowed to proceed with mixing for 1 h. The peptides were deprotected and released from resin by treatment with 92.5:2.5:2.5:2.5 (v/v) TFA/phenol/water/triisopropylsilane for 2 h. The peptides were triturated with cold ethyl ether and purified by reversed-phase HPLC equipped with a $C_{18}$ column. Peptide labeling with biotin was performed by dissolving the HPLC purified peptide (~5 mg) in 500 μL of 1:1 (v/v) DMF/150 mM sodium bicarbonate (pH 8.5) followed by the addition of 3 equiv of NHS-$PEG_4$-Biotin (cat no. 21442, Thermo Fisher Scientific). After 1 h, the reaction was quenched and the peptide was again purified by RP-HPLC. The authenticity of each peptide was confirmed by MALDI-TOF mass spectrometry analysis. The purity of each peptide (>95%) was assessed by reverse-phase HPLC equipped with an analytical $C_{18}$ column.

CP9-ZIZIT (1 mg/kg) was delivered by intranasal inhalation 1 hour prior to LPS (5 mg/kg) intranasal inhalation. 4 hours after LPS treatment mice were anaesthetized, blood, lung, liver, spleen, kidney and Broncho alveolar lavage fluid was collected from left lung lobe after ligating the right lung lobes. Collected broncho alveolar lavage fluid was analyzed for total protein content, TNFα and IL6. Right lung lobes were excised and weighed to record wet weight and part of it frozen for biochemical analysis.

LPS (5 mg/kg) was delivered in to mice by intra nasal inhalation and 1 hour after CP9-ZIZIT by intranasal inhalation. Mice were anaesthetized and blood, tissue, bronchioalveolar fluids were harvested and analyzed as described above.

CP9-ZIZIT (1 mg/kg) was delivered by intranasal inhalation 1 hour prior to LPS (10 mg/kg) by intra peritoneal injection. 16 hours after LPS treatment mice were anaesthetized, and blood, tissue, bronchioalveolar fluids were harvested and analyzed as described above.

Cellular examinations showed that CP9-ZIZIT can effectively ameliorate IL12b, iNOS and TNFα level following LPS stimulation (FIGS. 11A to 11D) presumably by downregulating Calcineurin/NFAT signaling.

Although ZIZIT-cisPro is approximately 15-fold more active than ZIZIT for binding to CN in vitro, CP9 is approximately 12-fold more active than $R_{11}$ for cellular uptake. As a result, CP9-ZIZIT showed comparable cellular activity with $R_{11}$-ZIZIT-cisPro. Importantly, both CP9-ZIZIT and $R_{11}$-ZIZIT-cisPro were approximately 100-fold more potent than $R_{11}$-VIVIT in cellular assays. For example, treatment of macrophages with 1 μM CP9-ZIZIT or $R_{11}$-ZIZIT-cisPro was significantly more effective than 50 μM $R_{11}$-VIVIT in attenuating the production of inflammatory cytokines (FIGS. 11A to 11D). CP9-ZIZIT at 1 μM concentration effectively inhibited LPS induced NFATc3 translocation in macrophages (FIG. 12).

In mouse models of endotoxin challenge induced ALI/ARDS, CP9-ZIZIT pretreatment significantly reduced the pulmonary proteinaceous edema, lung wet to dry ratios, extracellular fluid leakage in to BALF and also resulted in a corresponding decrease in TNFα and IL-6.

The CP9-ZIZIT pretreated mice (1 mg/kg body weight) subjected to ALI/ARDS by intranasal LPS instillation developed attenuated pulmonary edema, decreased cytokines and this ALI/ARDS disease phenotype was similar to that of the NFATc3−/− mice that showed healthy pulmonary arterial Oxygen saturation, decreased pulmonary edema, BALF cytokines, lung wet to dry ratio's and improved survival during severe sepsis by CLP. In terms of cellular distribution, CP9-ZIZIT-Biotin was distributed equally in macrophages and neutrophils as evidenced by flow cytometry.

The materials and methods of the appended claims are not limited in scope by the specific materials and methods described herein, which are intended as illustrations of a few aspects of the claims and any materials and methods that are functionally equivalent are within the scope of this disclosure. Various modifications of the materials and methods in addition to those shown and described herein are intended to fall within the scope of the appended claims. Further, while only certain representative materials, methods, and aspects of these materials and methods are specifically described, other materials and methods and combinations of various features of the materials and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A composition, comprising a peptide 7 to 100 amino acids in length comprising the amino acid sequence SEQ ID NO:1, and wherein the composition inhibits calcineurin (CN) —nuclear factor of activated T cell (NFAT) signaling.

2. The composition of claim 1, wherein the peptide comprises the amino acid sequence SEQ ID NO:2.

3. The composition of claim 1, wherein the peptide comprises the amino acid sequence SEQ ID NO:3.

4. The composition of claim 1, wherein the peptide comprises the amino acid sequence SEQ ID NO:4.

5. The composition of claim 1, wherein the peptide comprises an amino acid sequence selected from the group consisting of SEQ NOs:33-46.

6. The composition of claim 1, wherein the composition binds to CN with at least about 10-fold higher affinity than SEQ ID NO:47.

7. The composition of claim 1, having a $K_D$ (nM) for CN of about 43±12 or less.

8. The composition of claim 1, having a $K_D$ (nM) for CN of about 2.6±0.8.

9. A method for inhibiting CN-NFAT signaling in a cell, comprising contacting the cell with the composition of claim 1.

* * * * *